(12) United States Patent
Summerton

(10) Patent No.: US 8,084,610 B2
(45) Date of Patent: Dec. 27, 2011

(54) COMPOSITIONS AND METHODS FOR DETECTING AND TREATING TUMORS CONTAINING ACIDIC AREAS

(76) Inventor: James Edward Summerton, Corvallis, OR (US)

( * ) Notice: Subject to any disclaimer, the term of this patent is extended or adjusted under 35 U.S.C. 154(b) by 959 days.

(21) Appl. No.: 11/449,495

(22) Filed: Jun. 7, 2006

(65) Prior Publication Data

US 2007/0286803 A1  Dec. 13, 2007

(51) Int. Cl.
*C07D 213/00* (2006.01)
*C07C 61/06* (2006.01)

(52) U.S. Cl. .................. 546/26; 546/1; 546/2; 546/285; 562/400; 562/503; 556/1

(58) Field of Classification Search ............... 514/2, 1.1; 546/1, 2, 26
See application file for complete search history.

(56) References Cited

U.S. PATENT DOCUMENTS

| | | | |
|---|---|---|---|
| 6,030,941 A | 2/2000 | Summerton et al. | |
| 6,878,700 B1 * | 4/2005 | Link et al. | 514/183 |
| 7,041,682 B2 * | 5/2006 | Shih et al. | 514/326 |
| 7,132,393 B2 | 11/2006 | Summerton | |
| 7,285,529 B2 | 10/2007 | Summerton | |
| 7,572,811 B2 * | 8/2009 | Pan et al. | 514/315 |

OTHER PUBLICATIONS

Mease, Ronnie C (Clinical Cancer Research : an official journal of the American Association for Cancer Research, vol. 14, No. 10, pp. 3036-3043, 2008).*
Pham, Tien Q (Journal of nuclear medicine : official publication, Society of Nuclear Medicine 48(8), 1348-56, 2007).*
Liu, Xiang (Nuclear Medicine and Biology 35(7), 769-81, 2008).*
Howman-Giles R. (Journal of nuclear medicine : official publication, Society of Nuclear Medicine 36(8), 1372-6, 1995).*
Celen Sofie (Nuclear Medicine and Biology 34(3), 283-91, 2007).*
Butler J. A. (American journal of surgery 157(1), 126-9, 1989).*
Stubbs M (Advances in enzyme regulation, (1999) vol. 39, pp. 13-30).*
Stubbs M (Molecular medicine today, (Jan. 2000) vol. 6, No. 1, pp. 15-19).*
Aktolun C (Clinical nuclear medicine, vol. 17, No. 3, pp. 171-176, 1992).*
Yuki (J Polymer Sci Polymer Chem Ed. 17, 3867-78, 1979).*
Bhowmik, Benoy B. (Spectrochimica Acta, Part A: Molecular and Biomolecular Spectroscopy 37A(2), 135-9, 1981).*
Clark, P. D. (Journal of Organic Chemistry 42(2), 359-61, 1977).*
Shen, Wang (Bioorganic & Medicinal Chemistry Letters 8(8), 891-896, 1998).*
Kozin et al., Cancer Research, vol. 61, pp. 4740-4743 (2001).
Rebec et al., J.Amer.Chem.Soc., vol. 108, pp. 6068-6069 (1986).
Zalutsky et al., Proc.Natl.Acad.Sci. USA, vol. 86, pp. 7149-7153 (1989).
Naeslund & Swenson, Acta.Obstet.Gynecol.Scand., vol. 32, pp. 359-367 (1953).
Jahde et al., Cancer Research, vol. 52, pp. 6209-6215 (1992).
Kuin et al., Cancer Research, vol. 54, pp. 3785-3792 (1994).

* cited by examiner

*Primary Examiner* — David Lukton
(74) *Attorney, Agent, or Firm* — Teri G. Andrews Attorney at Law

(57) ABSTRACT

Improved compositions have been developed which are selectively sequestered in acidic areas of tumors. When the compositions contain a radioisotope effective to report the presence of the composition, the compositions are useful for detecting tumors. When the compositions contain radioisotopes effective to kill cells, the compositions are useful for treating tumors. Methods for detecting and treating tumors with such compositions are also disclosed.

6 Claims, 34 Drawing Sheets

Figure 1. Chlorambucil

Figure 2. Distribution of Acidity in Tumors

Figure 3. Previously-Postulated Acid-Pairs in Peptides

Figure 4. Non-Acid-Pairable Peptide Sequence

Figure 5. Preferred Amino Acid Sequences for Peptide pH-Switches a. core repeating sequences

| # | % glutamic acid | core sequences | |
|---|---|---|---|
| i | 20.0% | [ELLLL]n | n = 3 to 10 |
| ii | 22.2% | [ELLLLELLL]n | n = 2 to 5 |
| iii | 25.0% | [ELLLLELL]n | n = 2 to 6 |
| iv | 28.6% | [ELLLLEL]n | n = 2 to 7 |
| v | 33.3% | [ELL]n | n = 5 to 16 |
| vi | 33.3% | [ELLLEL]n | n = 3 to 8 |
| vii | 36.4% | [ELLLELELLEL]n | n = 2 to 4 |
| viii | 36.4% | [ELLELELLLEL]n | n = 2 to 4 |

E = glutamic acid
L = lipophilic amino acids selected from leucine, isoleucine, norleucine, valine, methionine, and non-standard alpha amino acids of similar or greater side-chain lipophilicity b. Axial distribution plots Figure 6. Amino Acid Sequences
Unsuitable as pH-Switches
| # | %E | core seq. | axial dist. plot |
|---|-----|-----------|------------------|
| ix | 25% | [ELLL]$_n$ <br> n = 4 to 12 | 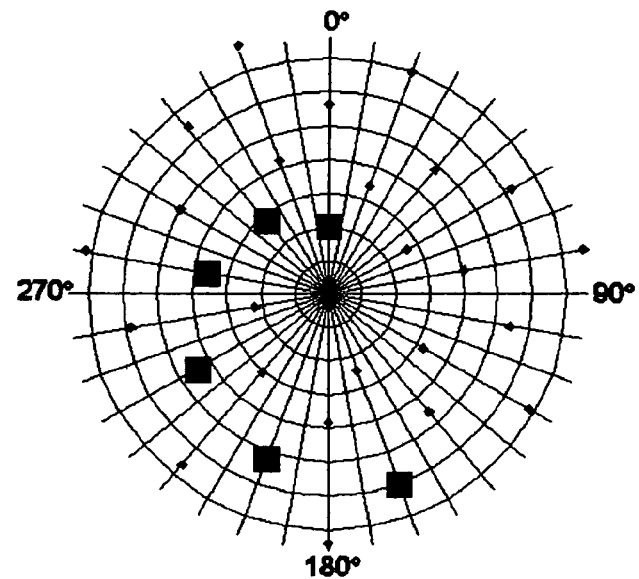 |
| x | 28.6% | [ELLLELL]$_n$ <br> n = 2 to 7 | 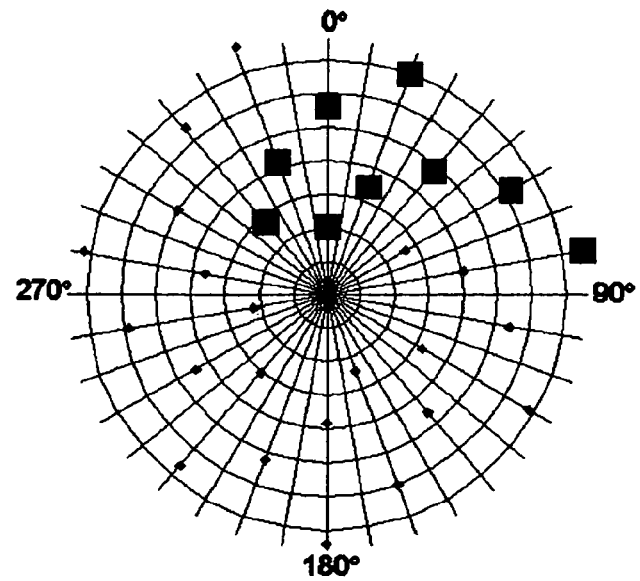 |

Figure 7. Lipophilic End Groups for pH-Switch Peptides
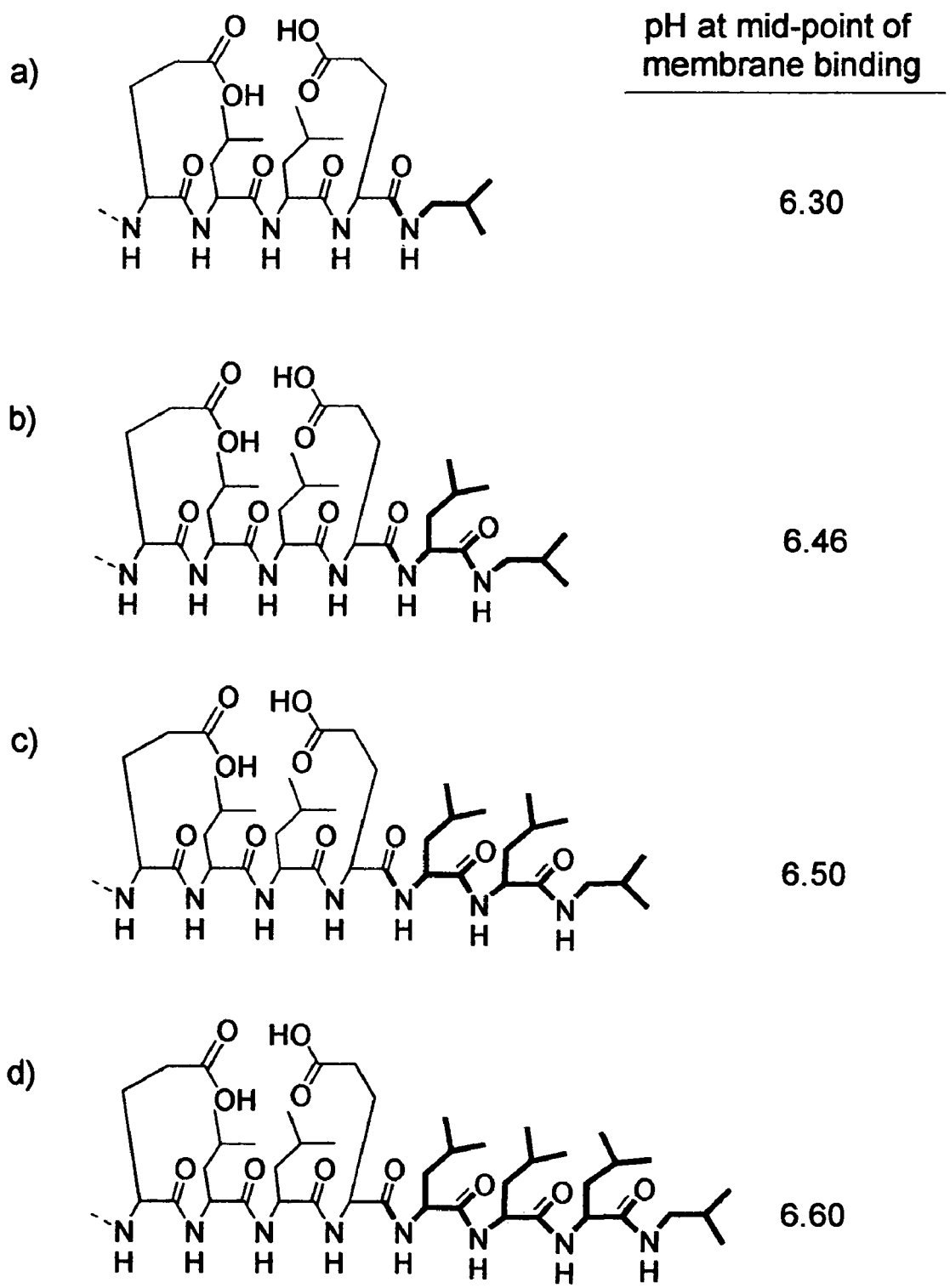
pH at mid-point of membrane binding
a) 6.30
b) 6.46
c) 6.50
d) 6.60

Figure 8. Representative End Structures for Improved pH-Discrimination
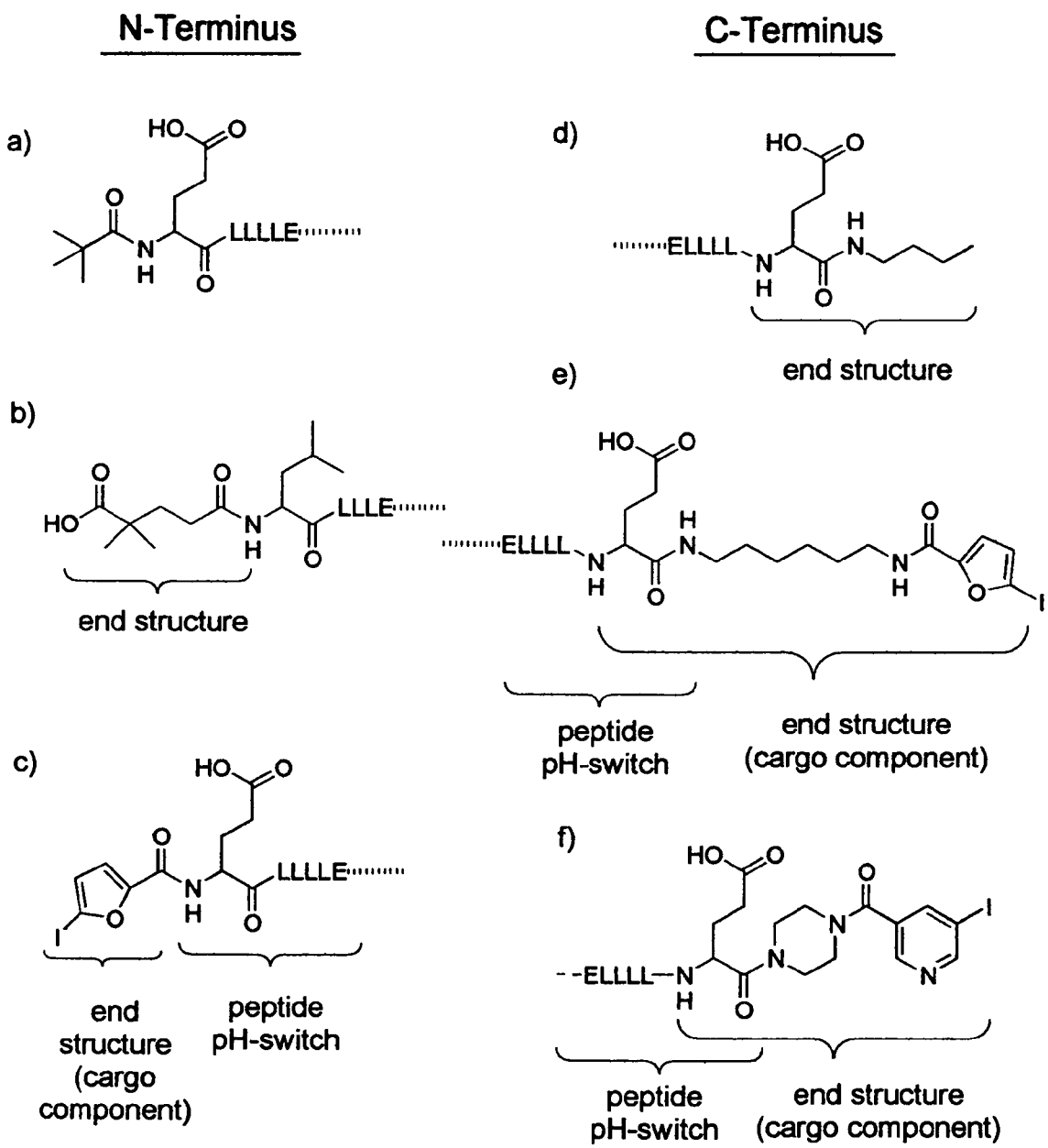

Figure 9. pH-Mediated Transition Between Forms
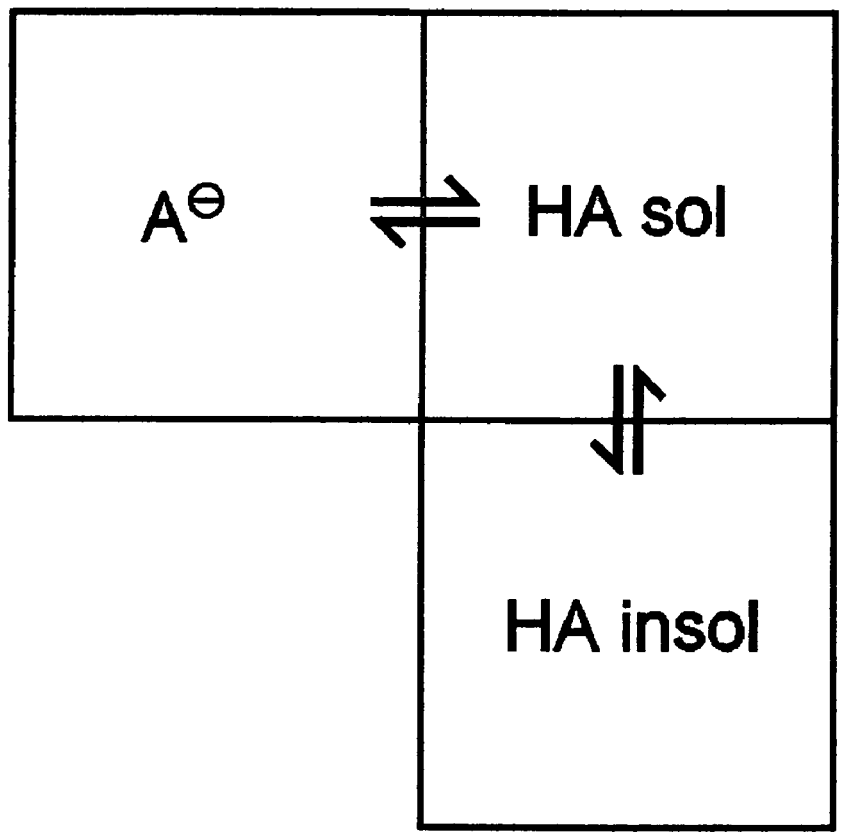
$$pH = pKa + \log \frac{[A^{\ominus}]}{[HA\ sol]}$$
$[A^{\ominus}] + [HA\ sol] + [HA\ insol] = 1$
$$P = \frac{[HA\ insol]}{[HA\ sol]}$$
P is octanol/water partitioning coefficient

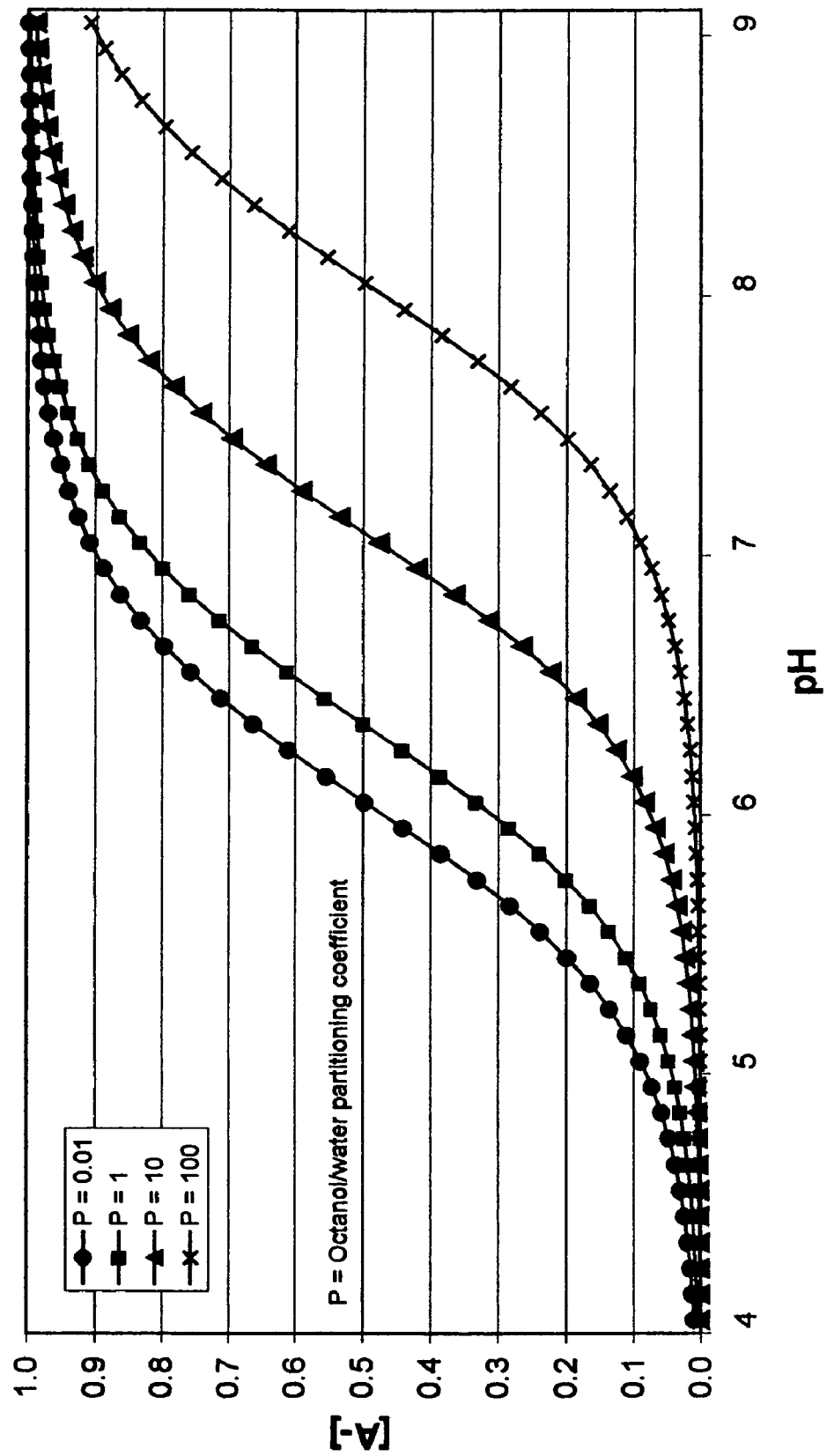
Figure 10. Calculated Titrations as Function of Lipophilicity of Acid Form

Figure 11. Expected Waters of Hydration
a) Conventional carboxylic acid
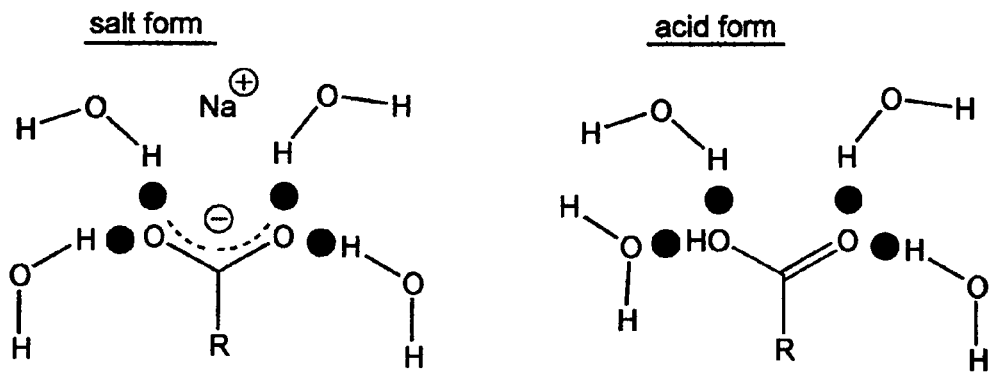
b) internally H-bonded carboxylic acid
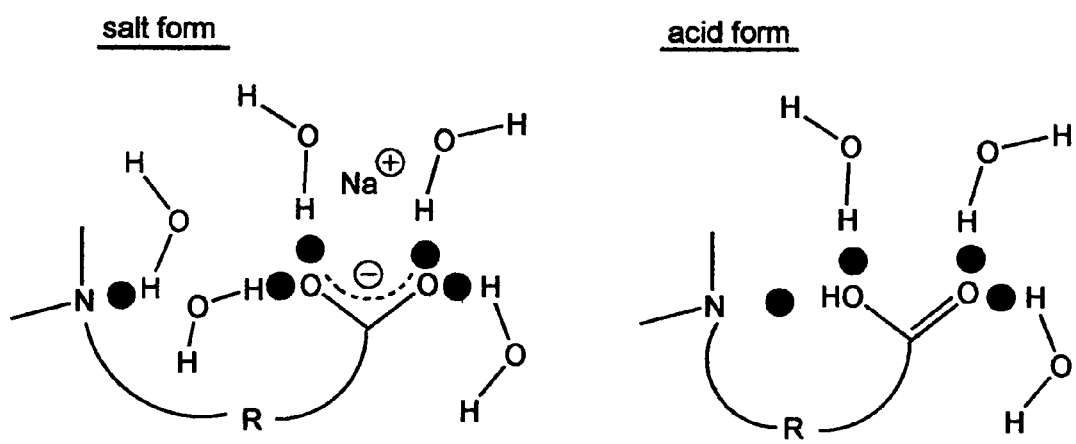

Figure 12. Acid-Specific H-Bond
a) Structure which forms acid-specific H-Bond
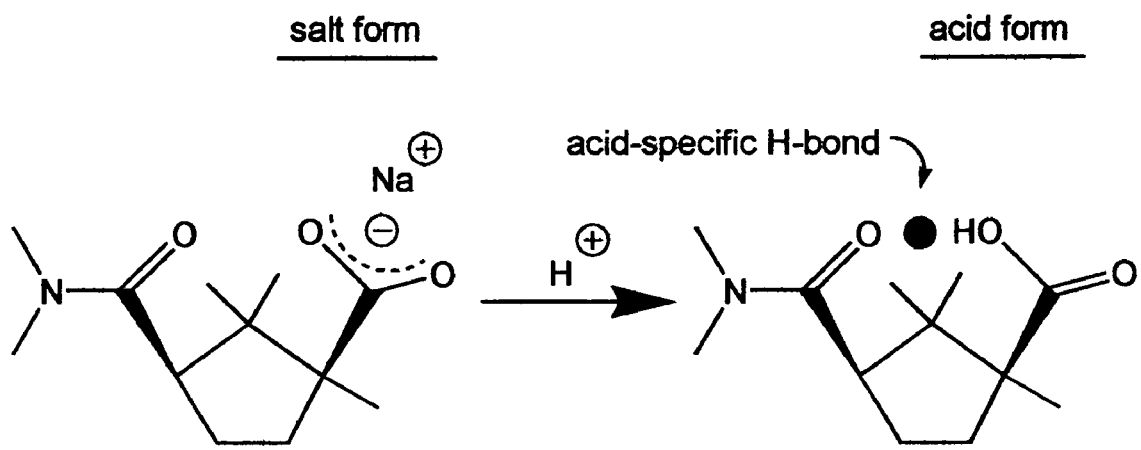
b) Structure which forms non-acid-specific H-bonds
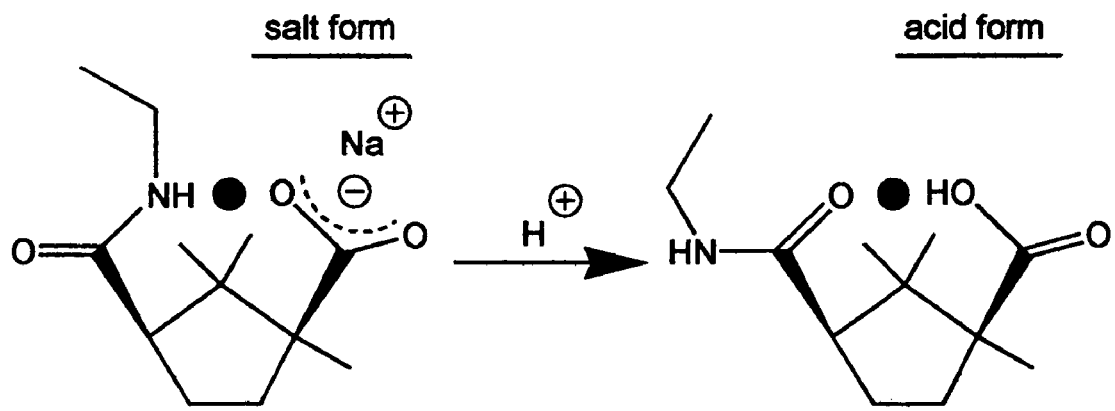

Figure 13. Representative Ring Structures Suitable for Advanced pH-Switches
a)
4-membered ring
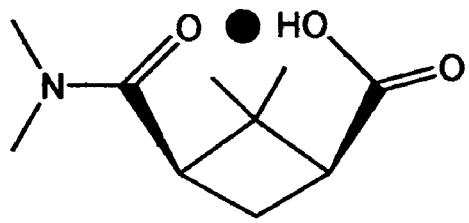
5-membered ring
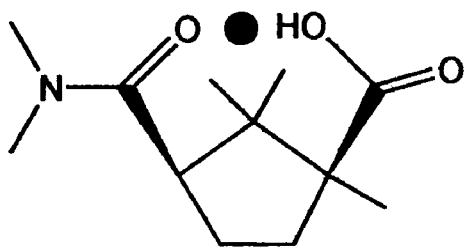
6-membered ring
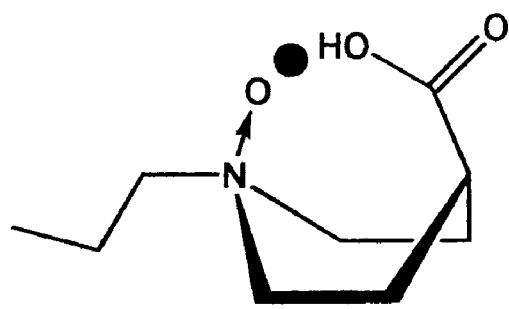
b)
unacceptable structure
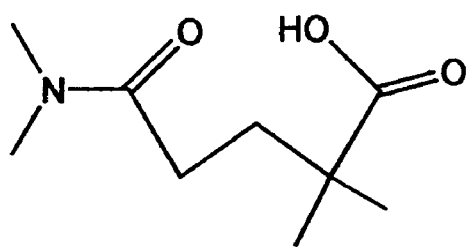

Figure 14a. Insulation of Carboxyl from Inductive Effects
| Structure | # of carbons separating carbonyl and phenyl ring | pKa |
|---|---|---|
| (benzoic acid) | 0 | 4.20 |
| (phenylacetic acid) | 1 | 4.31 |
| (3-phenylpropanoic acid) | 2 | 4.66 |
| (4-phenylbutanoic acid) | 3 | 4.75 |
| (butanoic acid) | no phenyl ring | 4.87 |
14b. Inadequate Insulation of Carboxyl from Inductive Effects
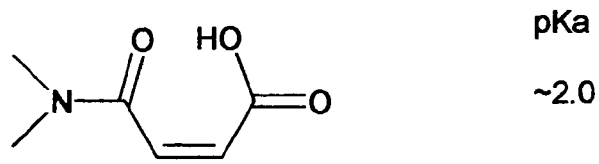
pKa
~2.0

Figure 15. Partial Shielding of H-bond Site
a) H-bond site open to solvent
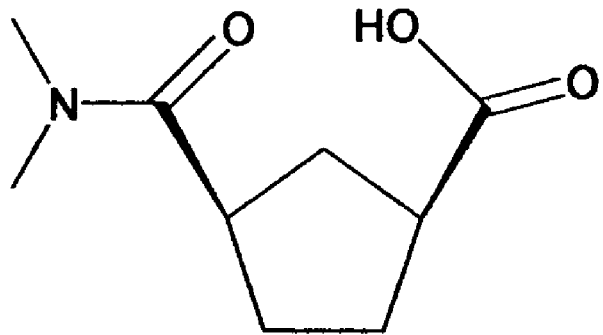
b) H-bond site partially shielded from solvent
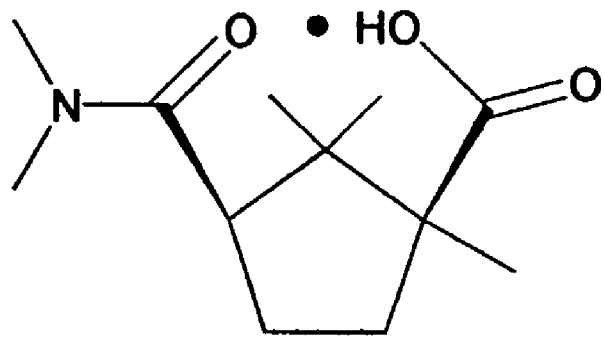

Figure 16. Low-Barrier H-bonds
a) Donor and representative acceptors
| Donor | approximate pKa | Acceptor | approximate pKa |
|---|---|---|---|
| R-C(=O)-OH | 4.8 | N≡C-CH₂-N(R₁)(R₂) | 4.60 |
| | | F₃C-CH₂-N(R₁)(R₂) | 4.75 |
| | | -O-N(R₁)(R₂) | 3.65 |
| | | R₁-N(R₂)-N-R₃ | 6.3 |
| | | R₂-N(R₁)(R₃)→O | 4.6 |
| | | R₂-C(=O)-CH₂-imidazole(R₁) | 5.5 |
b) Representative advanced pH-switches with low-barrier H-bonds
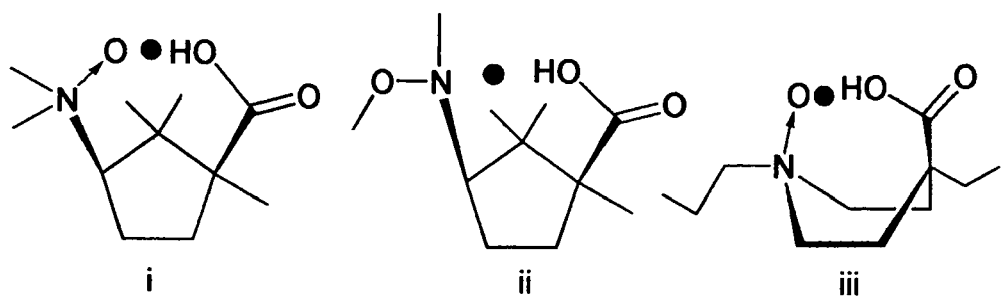
i   ii   iii

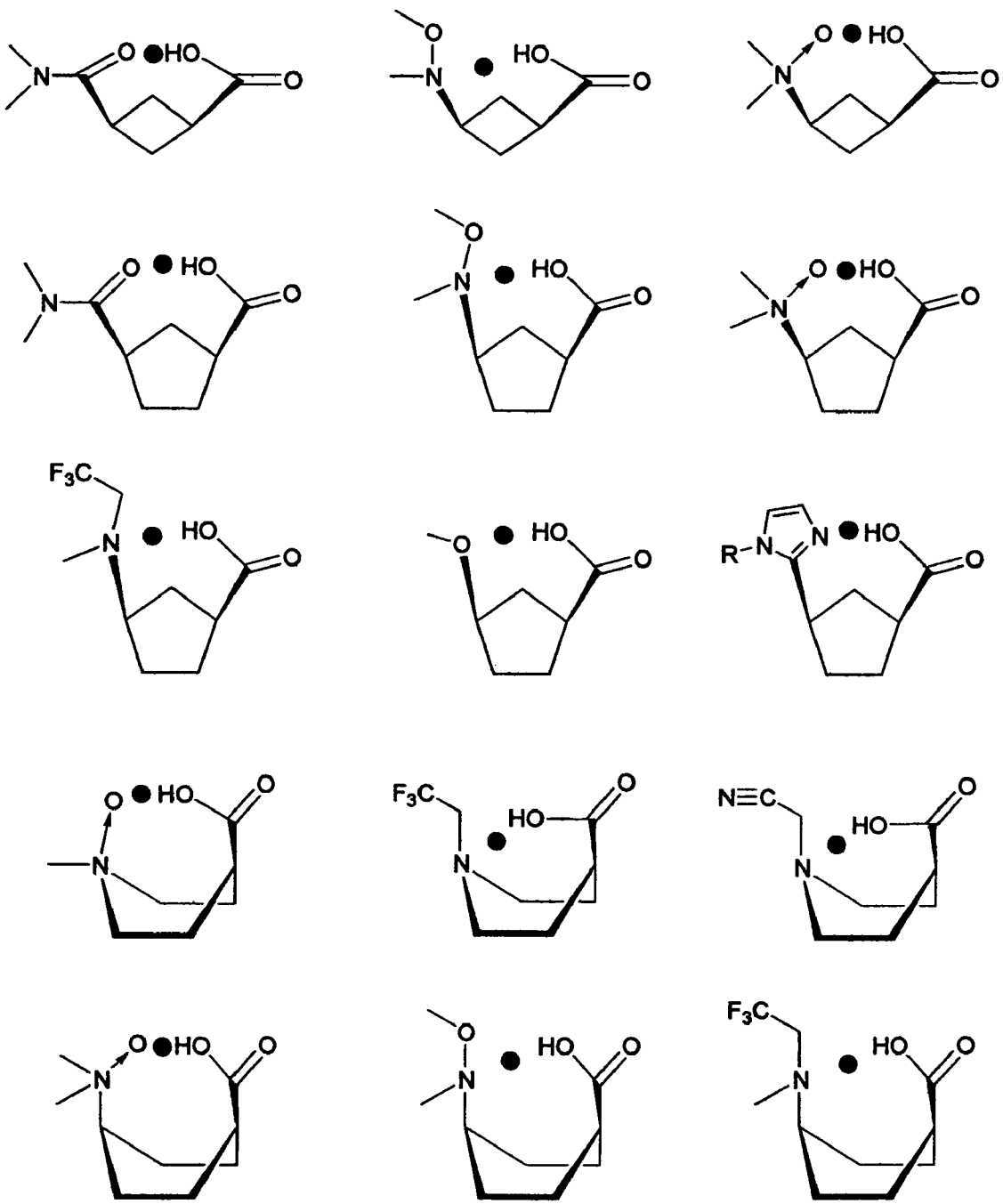
Figure 17. Representative Core Structures for Advanced pH-Switches

Figure 18. Structural Optimization
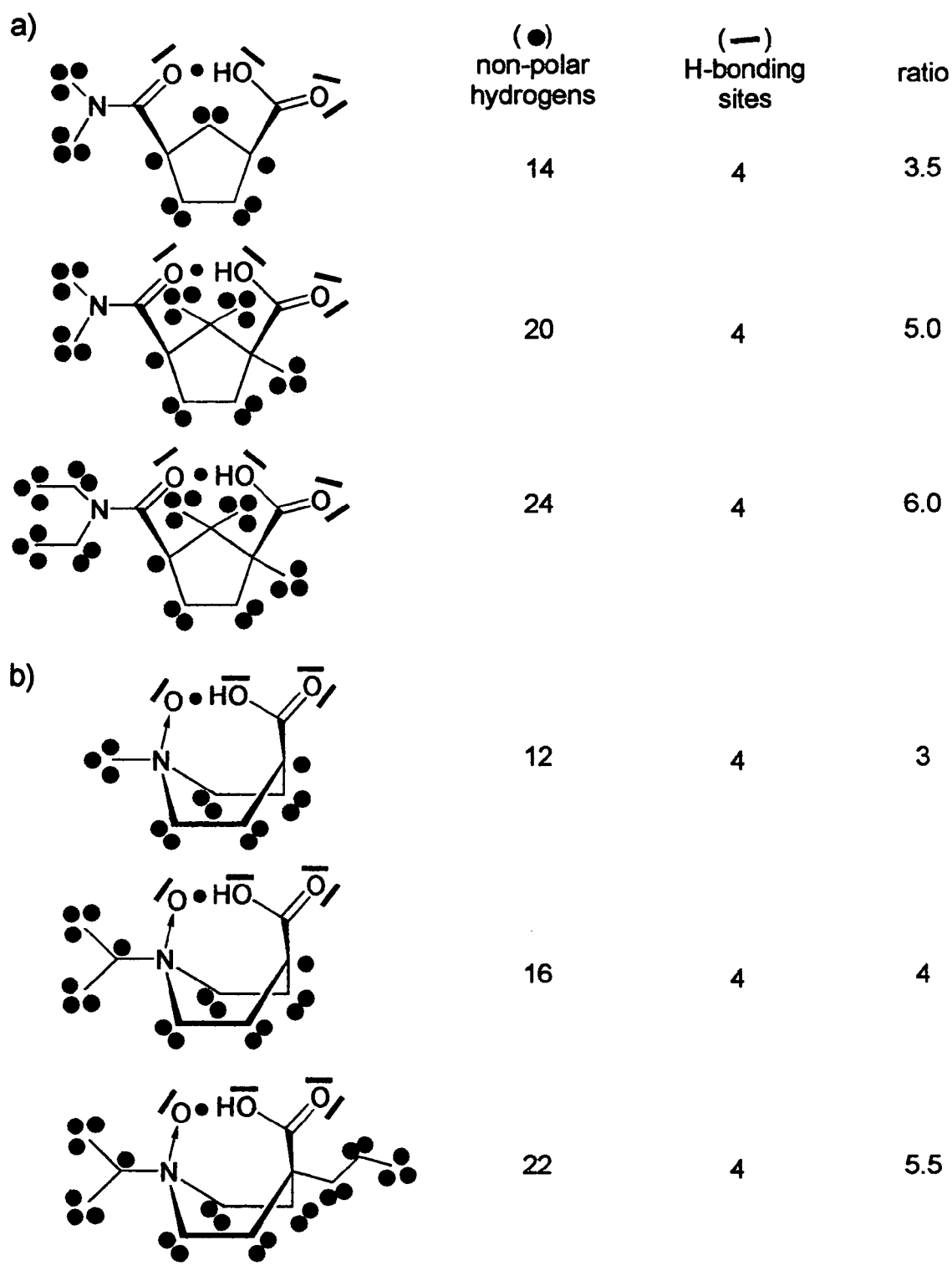

Figure 19. High-Specificity Onco-Tools
a) OncoTool with two pH-switches
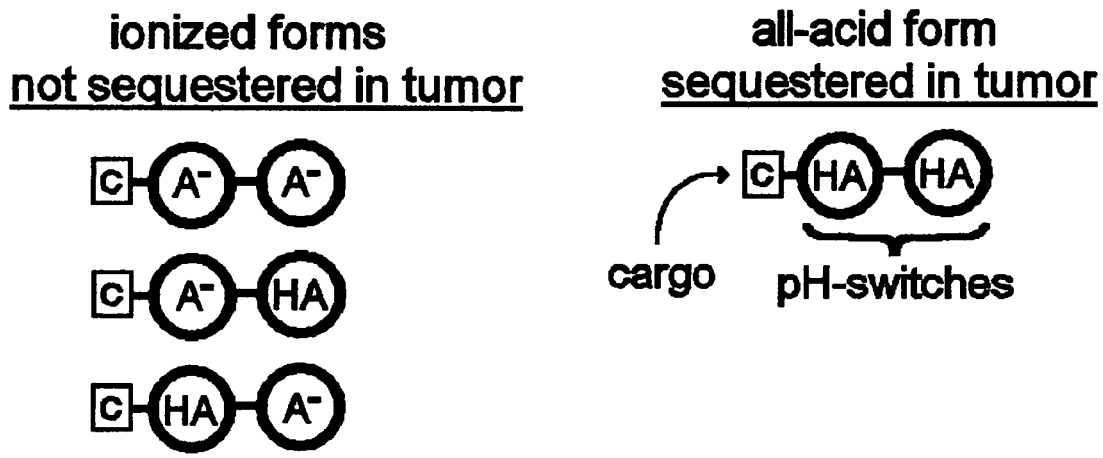
b) OncoTool with three pH-switches
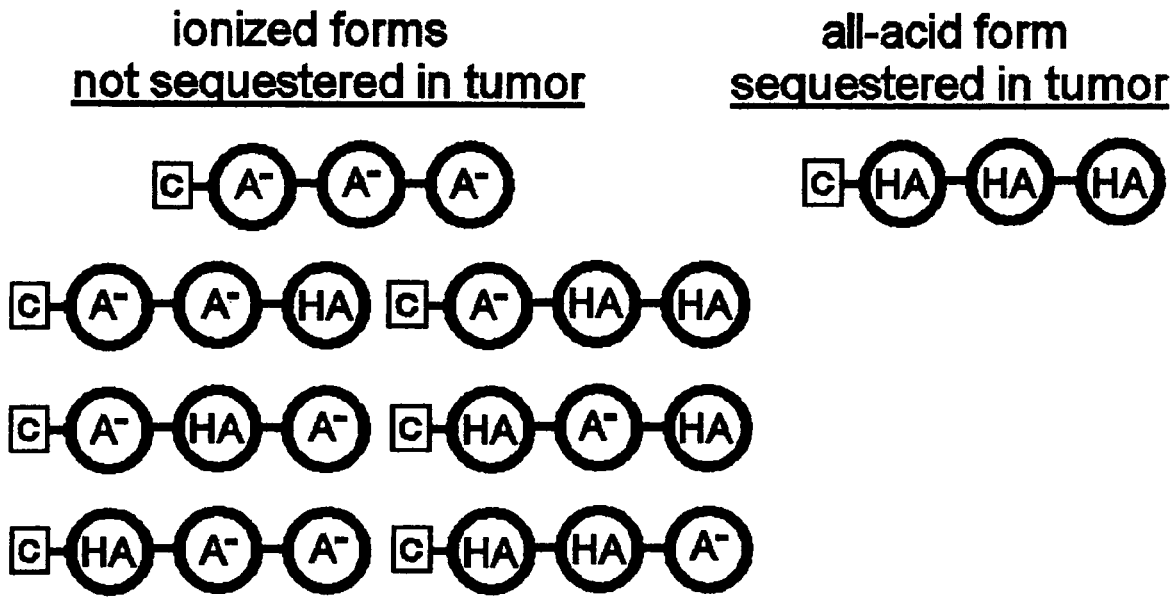

Figure 20. Oligomeric pH-Switch
a) structure
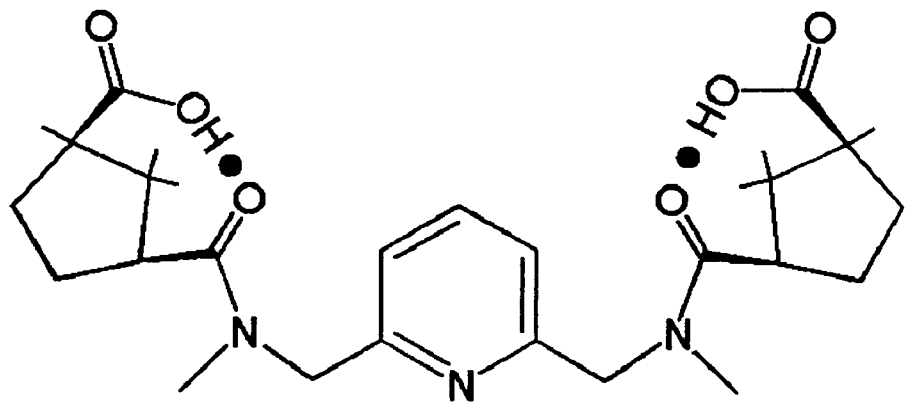
b) *n*-octanol/buffer partitioning
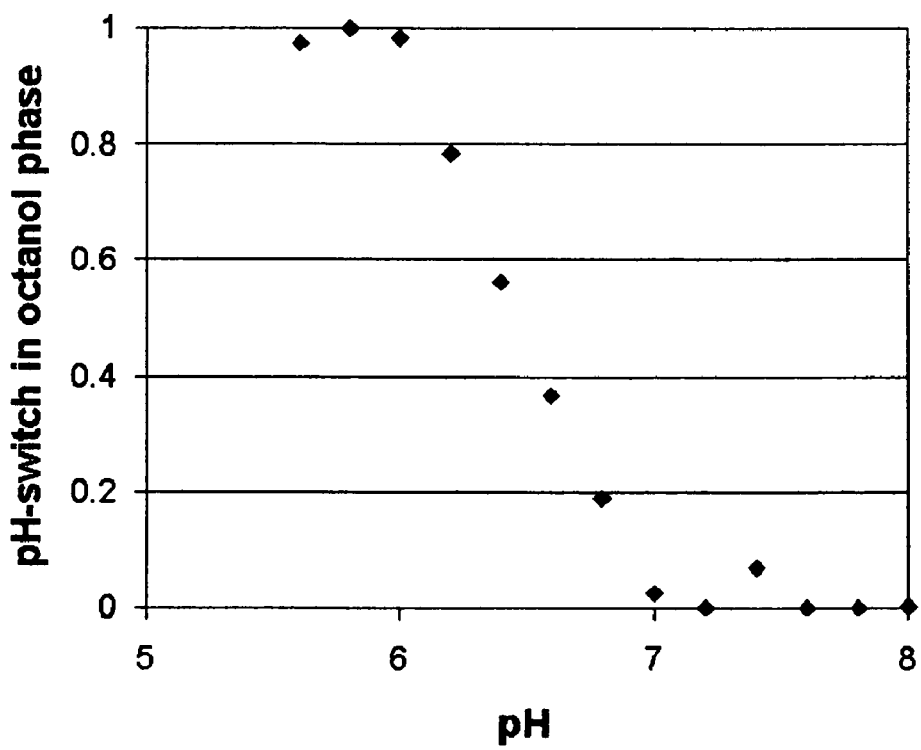

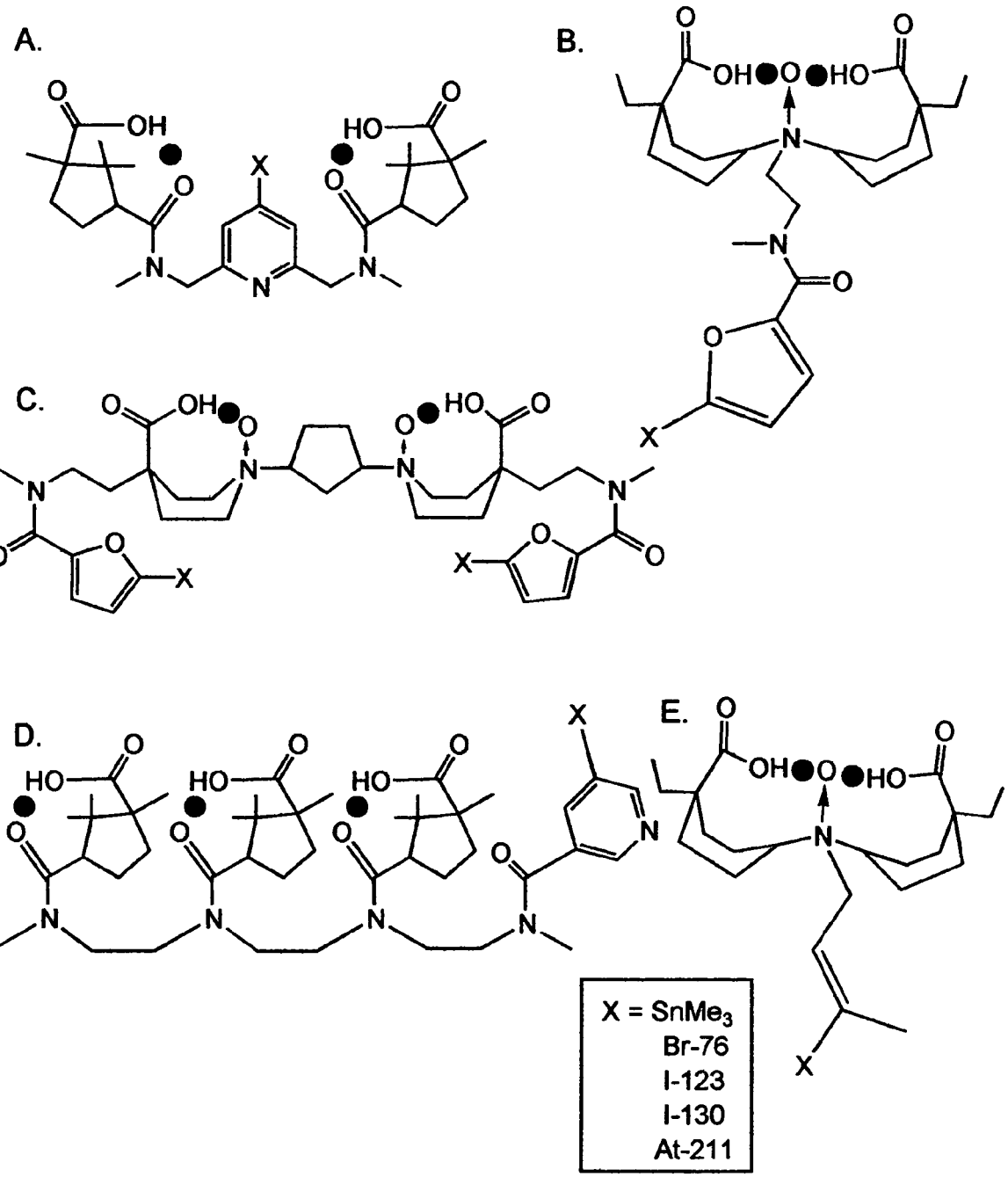
Figure 21. Onco Tools with Multiple Advanced pH-Switches

Figure 22. Conventional Cargo Component for Large Onco-Tools
a. Form which is effective to bind a radioisotope
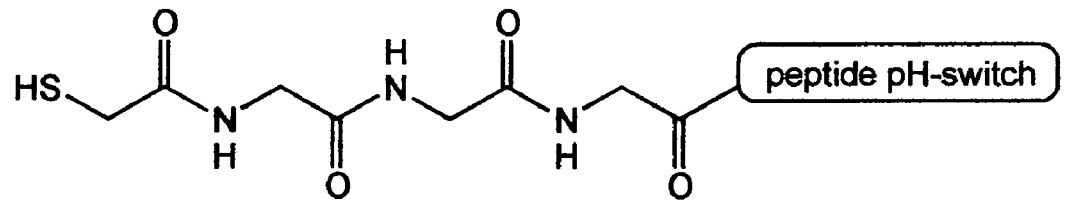
b. Form which contains a radioisotope
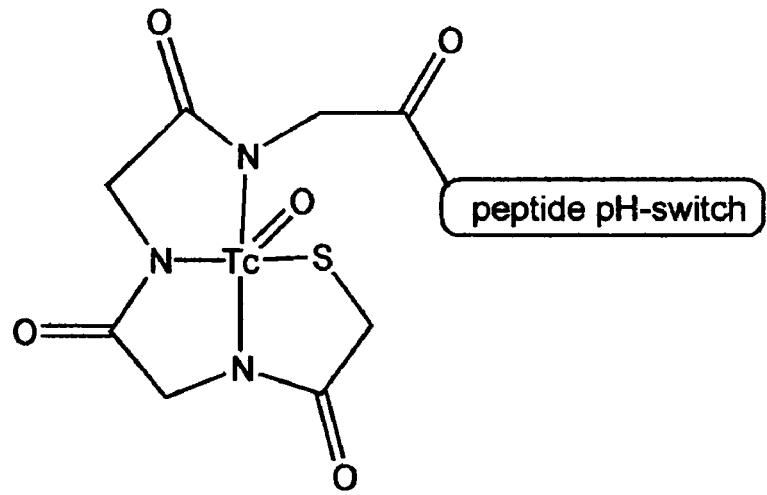

Figure 23. Advanced Cargo Components for Small Onco-Tools
a. Form which is effective to bind a radioisotope
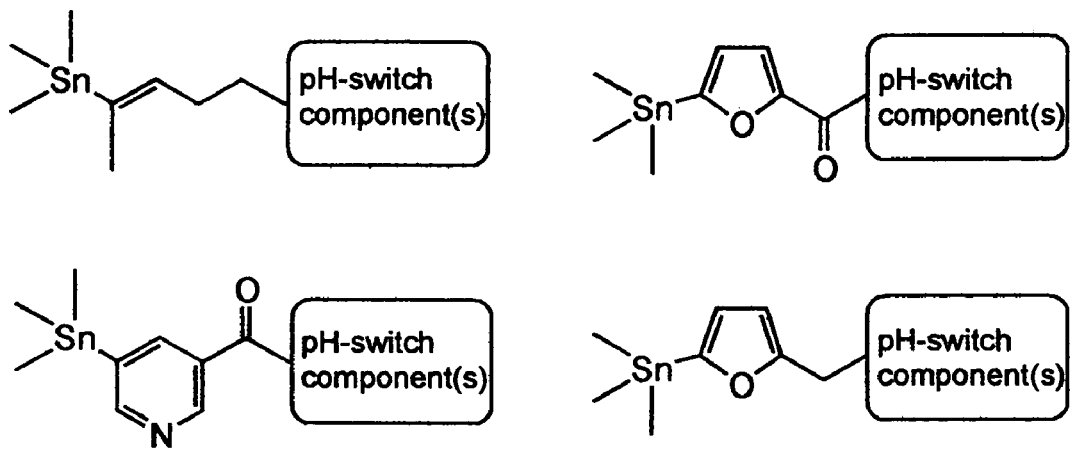
b. Form which contains a radioisotope
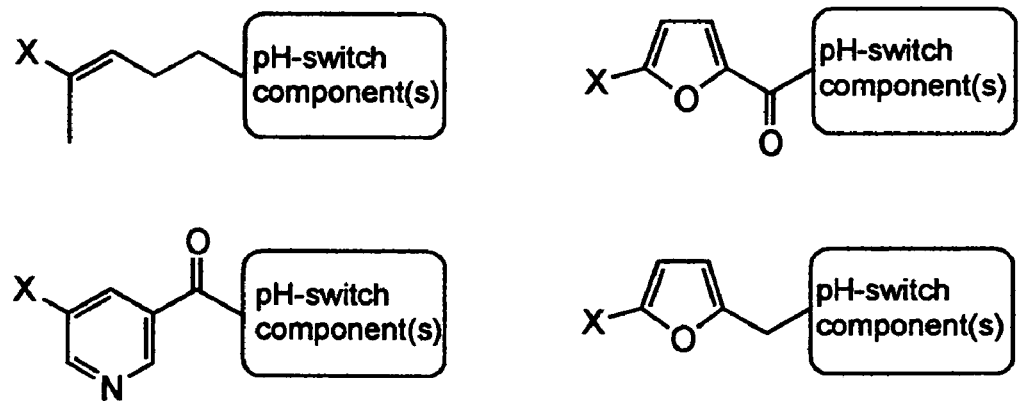
X = Halogen selected from Br, I, At c. Cargo components indistinct from pH-switch components X = Br, I, At Figure 24. Preparation of Onco Tool
Containing a New Peptide pH-Switch
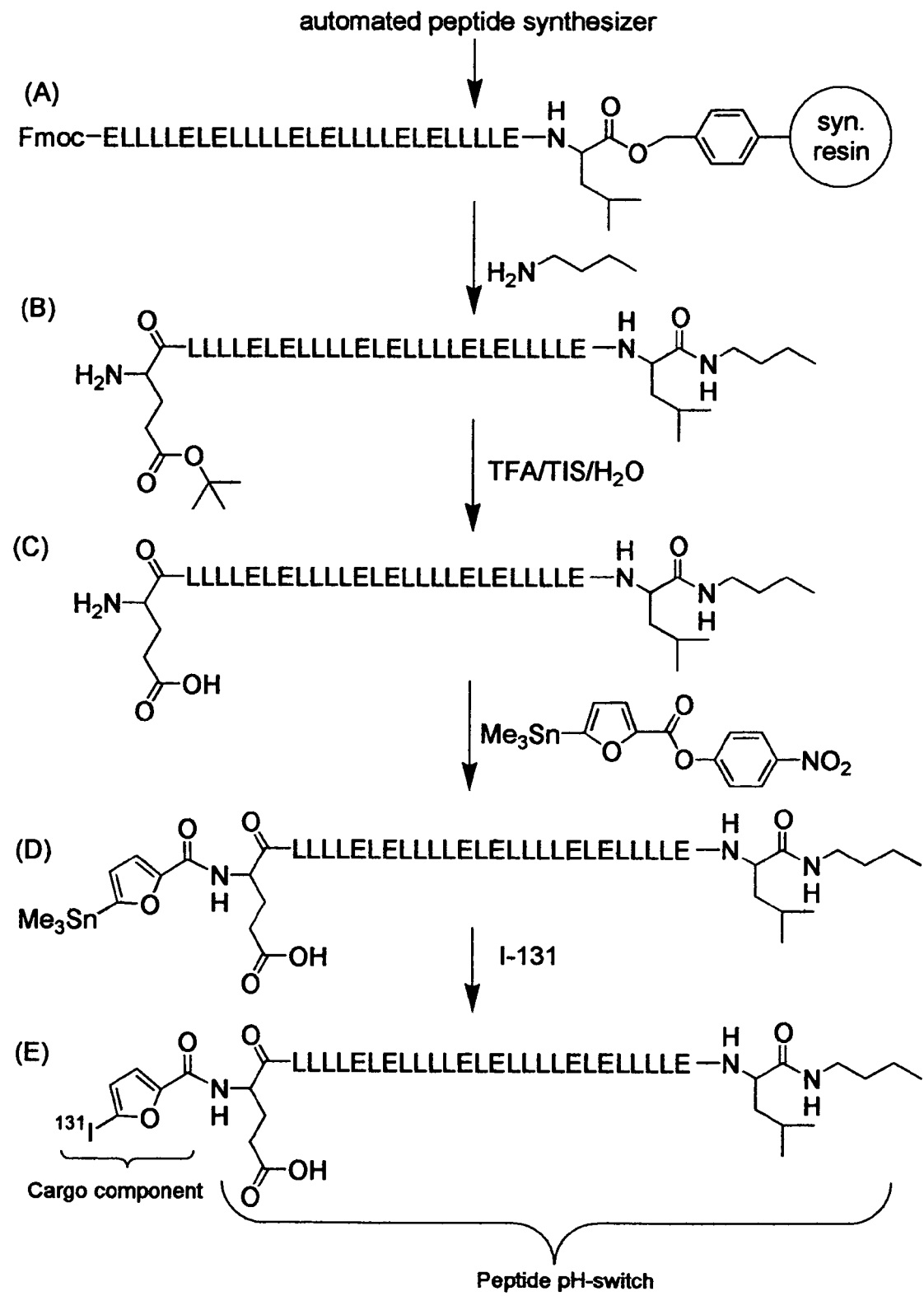

Figure 25. Preparation of Onco Tool Containing Peptide pH-Switch and Advanced pH-Switch
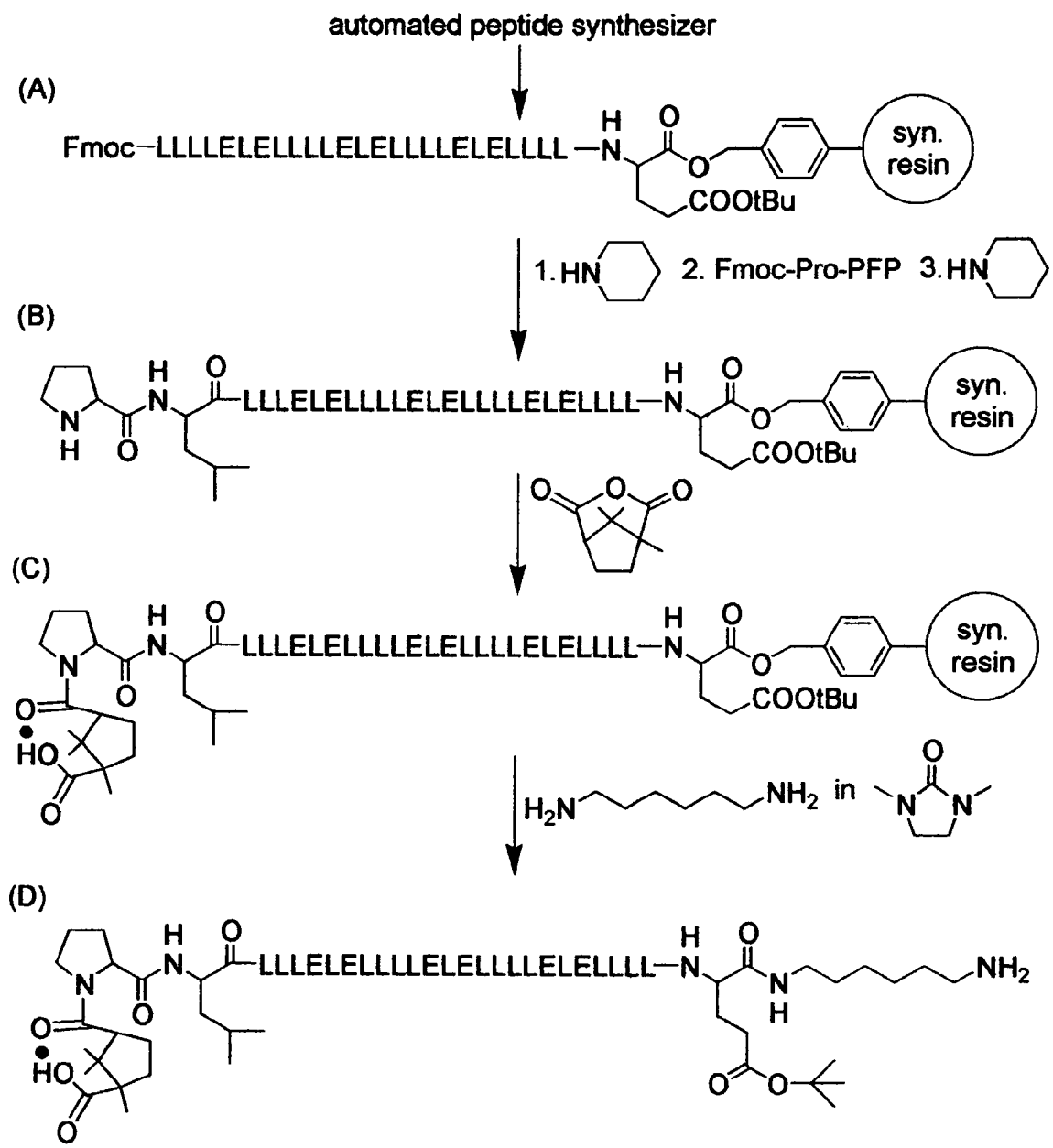

Figure 26. Synthetic Scheme for Conventional Cargo Component
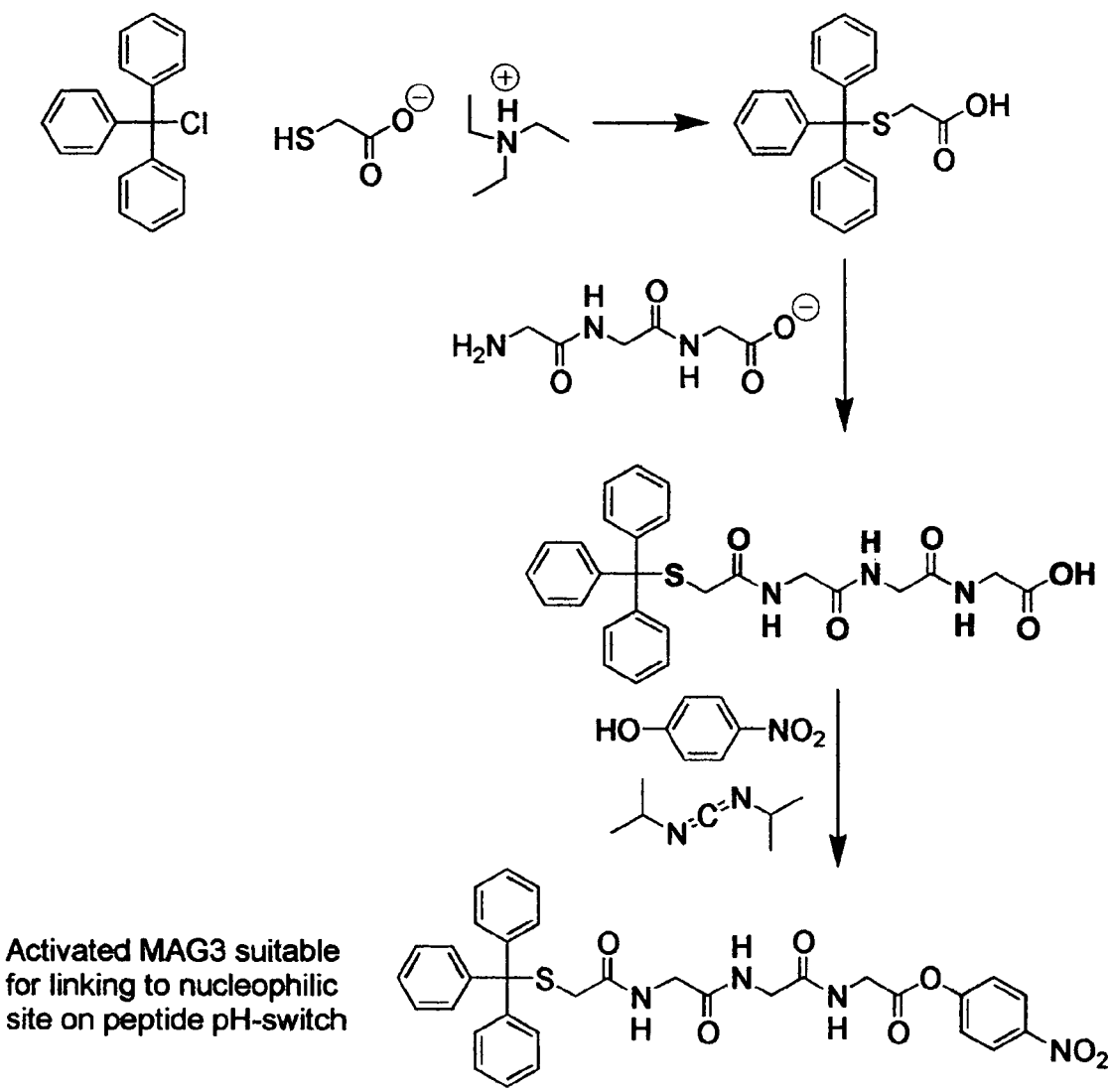
Activated MAG3 suitable for linking to nucleophilic site on peptide pH-switch

Figure 27. Synthetic Scheme for Advanced Cargo Component
a) Representative alkene-type advanced cargo component
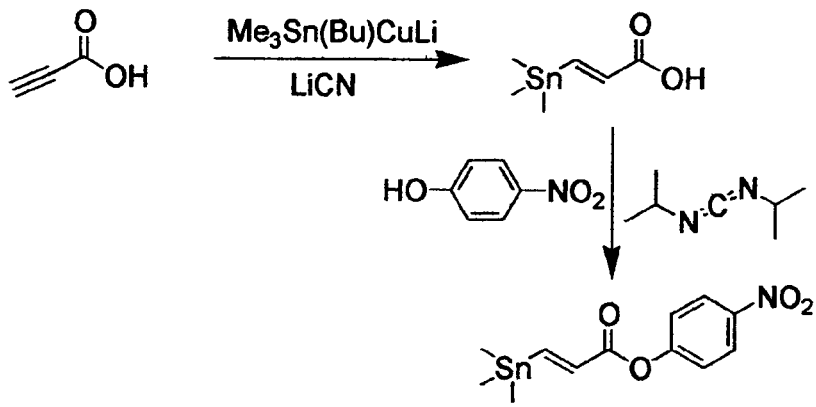
b) Representative 5-membered ring advanced cargo component
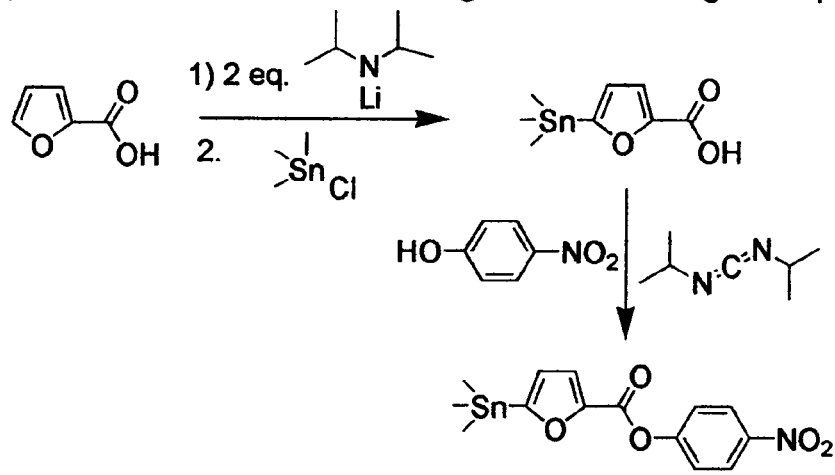
c) Representative 6-membered ring advanced cargo component
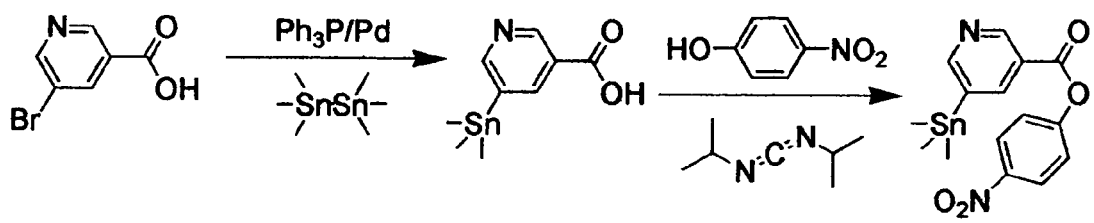

Figure 28. Preparation of Onco Tools Containing One Advanced pH-Switch
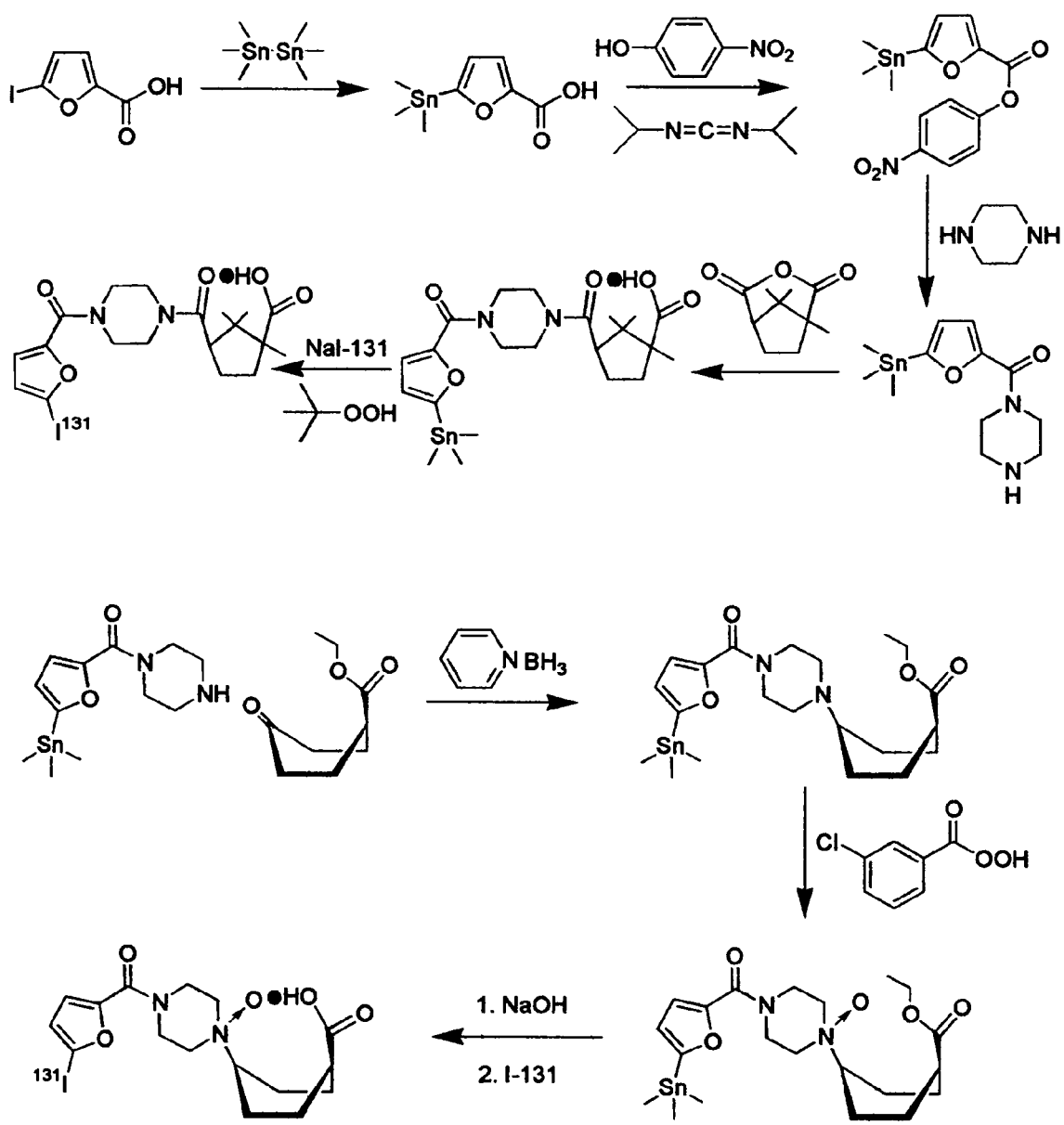

Figure 29. Preparation of an Onco Tool Containing Two Advanced pH-Switches
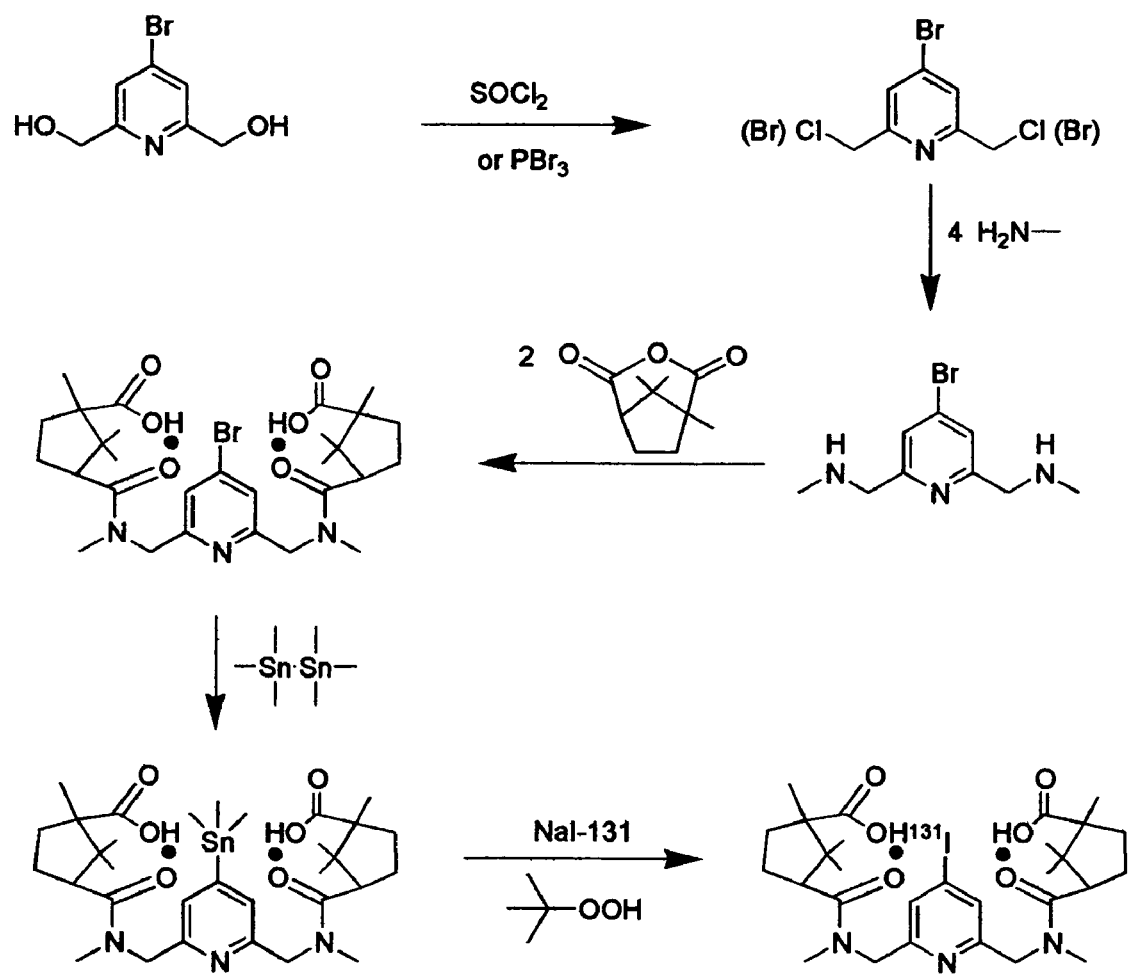

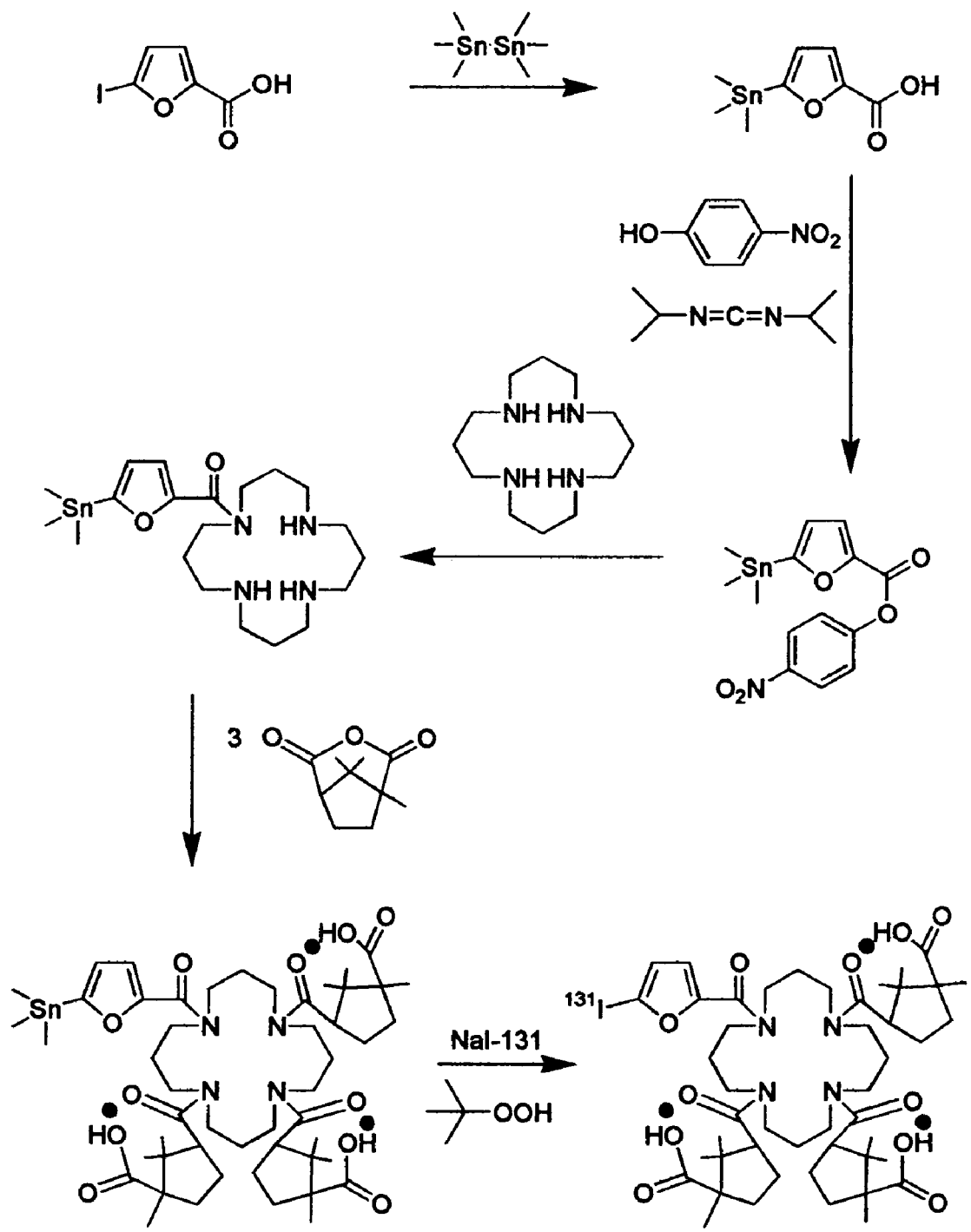
Figure 30. Preparation of an Onco-Tool Containing Three Advanced pH-Switches

COMPOSITIONS AND METHODS FOR DETECTING AND TREATING TUMORS CONTAINING ACIDIC AREAS

CROSS-REFERENCE TO RELATED APPLICATIONS

The present application discloses inventions comprising extensions and improvements to earlier inventions by the same inventor. Those earlier inventions are disclosed in pending applications (Ser. No. 11/069,849, pending; and, Ser. No. 11/069,387, allowed but not yet issued), neither of which has yet been published or otherwise disclosed to the public.

FIELD OF THE INVENTION

This invention relates to compositions which are selectively sequestered in acidic areas of tumors for the purposes of detecting and killing tumors.

BACKGROUND OF THE INVENTION

Brief overview of invention: In 1930 the famous physiologist Otto Warburg reported that one of the most universal characteristics of tumors is their acidity. Subsequent studies have confirmed that much of the interstitial space of tumors is acidic, ranging from about pH 6.0 to about pH 7.2. James Summerton, the present inventor, has devised novel compositions called "onco-tools" which are designed to exploit this acidity to afford early detection and safe and effective treatment of a broad range of tumors. Key to the mechanism of action of onco-tools are components called "pH-switches". At the pH of normal tissues (pH 7.4) a pH-switch exists in an anionic hydrophilic form which has a very low affinity for tissues, but when the pH-switch enters an acidic area in a tumor it undergoes a pH-mediated switch to a non-ionic lipophilic form that has a high affinity for tissues. As a consequence, an onco-tool does not bind to normal tissues, but it is sequestered in acidic areas of tumors. Onco-tools which are not sequestered in a tumor will be excreted by the kidneys. Onco-tools also contain a cargo component that serves to report the presence of the tumor (diagnostic use) or serves to kill the tumor (therapeutic use). Initial compositions and methods which exploit tumor acidity for detecting and treating tumors are described in two patent applications previously submitted by the present inventor (one of these applications is pending and one is allowed but not yet published or issued). The present patent application by the same inventor describes subsequent improvements and extensions in the design, preparation, properties, applications, and methods of use of these novel onco-tools.

Acidity in tumors: It has been known for many decades that most or all tumors larger than about 1 millimeter in diameter contain hypoxic/acidic areas. The likely cause of these hypoxic/acidic areas is that for tumors to grow larger than about 1 mm in diameter they must induce new blood vessels, and such tumor-induced blood vessels, particularly the capillaries, are abnormal, being too widely spaced, torturous in path, and their walls are excessively permeable. As a consequence, cells more than a few tens of microns from such tumor capillaries commonly are chronically hypoxic and the interstitial space surrounding them is acidic, ranging from as low as about pH 6.0 in areas most distant from capillaries, up to about pH 7.2 closer to capillaries, with pH values in the range of about 6.5 to 6.8 being most common. This acidity is probably due in substantial part to the hypoxia causing the tumor cells to shift to glycolytic metabolism, which leads to their producing and excreting lactic acid. While tumor cells at near-normal pH in close proximity to capillaries have high metabolic rates and fast cell division, those tumor cells in hypoxic/acidic areas a greater distance from capillaries have low metabolic rates and divide slowly or not at all. These slow and non-dividing tumor cells are called quiescent.

The quiescent tumor cells in hypoxic/acidic areas of tumors probably constitute the greatest impediment to long-term success with conventional cancer therapies. This is because while conventional cancer therapies (radiation and chemotherapeutics) are fairly effective in killing the more vulnerable fast-dividing cells, such as those tumor cells in close proximity to tumor capillaries, most such therapies have been explicitly selected for their ability to spare slow-dividing and non-dividing cells typical of most normal tissues. Therefore, not surprisingly, conventional cancer therapies are also rather ineffective against slow-dividing and non-dividing quiescent tumor cells. As a consequence, tumor treatments typically kill predominantly the fast-dividing cells of a tumor while sparing quiescent cells of that tumor. This initial killing of the more vulnerable fast-dividing tumor cells causes the tumor to go into remission, but after those killed cells have been disposed of by the body's normal cleanup processes, all too often the treatment-resistant quiescent cells in the hypoxic/acidic areas of the tumor slowly regain access to adequate oxygen, nutrients, and waste disposal—allowing them to revert to high metabolic rate and fast cell division. This rejuvenation of the previously quiescent tumor cells commonly leads to the dreaded relapse that kills so many patients.

Prior efforts to exploit acidity in tumors: The hypoxic/acidic properties of tumors have been known for over 75 years and it has long been speculated that such properties might be exploitable for therapy. However, to date it appears the most successful efforts to exploit these properties have focused on the hypoxia. Specifically, substances have been developed which exhibit minimal cytotoxicity in normoxic cells, while exhibiting considerable cytotoxicity in hypoxic cells. One such agent has progressed to the clinical trials stage.

Compared to exploiting the hypoxia in tumors, until quite recently there appears to have been much less success in exploiting the acidity of tumors. One unsuccessful approach was based on the observation that acid pH in tissues acts to sensitize those tissues to thermal damage. However, efforts to exploit this acid-mediated sensitivity of cells gave disappointing results.

Another approach relating to acidity in tumors is based on the fact that the low pH in tumors ionizes weak-base cytotoxic agents and thereby renders them membrane-impermeable, which in turn results in preferential reduction of entry of a number of such weak-base agents into cells in acidic areas of tumors relative to entry of such agents into cells in areas of more normal pH. In this regard, rather than attempting to exploit the low pH in the tumor, efforts were instead focused on raising the pH in the tumors as a means to partially de-ionize and thereby enhance the entry of such weak-base cytotoxic agents into cells of the tumor, and such efforts have met with some success.

Related art: Still another approach, and one which relates somewhat to the present invention, relies on the fact that the low pH in the interstitial space of tumors will effect partial de-ionization of weak-acid cytotoxic agents. As a consequence of this lesser degree of ionization of weak-acid agents in acidic areas of tumors, one would expect that such agents should show enhanced cell entry and hence greater cytotoxicity against cells in the acidic areas of tumors. This expectation has been tested by Kozin et al., wherein they took measures to make tumors in tumor-bearing mice more acidic by established methods (Cancer Research Vol. 61, pages 4740-4743(2001)). They reported that, as predicted, a reduction of about 0.3 pH units in the tumors coincided with a modest 1.7-fold improvement in tumor growth delay afforded by the weak-acid (pKa 5.8) cytotoxic agent, Chlorambucil (shown in FIG. 1). In the conclusion to their paper they wrote: "To our knowledge, CHL (Chlorambucil) is the only clinical therapeutic that is a weak-acid with the appropriate pKa≦6.5. This study thus provides a rationale for the design of novel, potent drugs exhibiting similar weak-acid properties and for which diffusion contributes to intracellular uptake. As also shown here, the combined use of such compounds with radiation and/or modulators of the pH gradient provide additional opportunities for maximizing the therapeutic response." In this paper, the authors state that their results with the off-the-shelf chemotherapeutic, Chlorambucil, provide a rationale for designing new weak-acid anti-cancer drugs which may show high efficacy—but no guidance is given for design criteria or prospective molecular structures for such drugs, nor is any guidance given on what specific properties are desirable, nor is any guidance given on how to go about designing and preparing such weak-acid drugs, nor is any guidance given concerning applications or methods of use of such drugs.

Other art which relates more closely to the current invention is the following. In 1993 James Summerton, the present inventor, began development of novel transporter peptides designed from first principles to exploit the pH differential between acidified endosomes (pH 5.0) and the cytosol of cells (pH 7.4) for the purpose of transporting non-ionic antisense oligos across the endosomal membrane into the cytosol of cells (Summerton & Weller, U.S. Pat. No. 6,030,941). Those transporter peptides were designed to convert to a non-ionic/ moderately-lipophilic form at the pH within late-stage endosomes (about pH 5.0), and then pass through the endosomal membrane. As they entered into the neutral pH of the cytosol, the transporter peptides were designed to revert to their anionic/hydrophilic form, with that re-ionization and solvation providing the motive force for pulling the attached antisense oligo across the endosomal membrane. While those early transporter peptides resemble in several aspects some of the onco-tools of the current invention, it should be noted that: a) those early transporter peptides are ineffective for discriminating between normal tissues and acidic areas of tumors; and, b) the claims in the 941 patent covering those early transporter peptides do not read on the onco-tools of the current invention; and, c) the claims in the current patent application do not read on those early transporter peptides disclosed in the 941 patent.

Additional art that is still more closely related to the present invention, which was also developed by the same inventor and which has not yet been disclosed to the public, is the following. Several years ago Summerton altered the transporter peptide design in order to produce specialized peptides explicitly designed to exploit the small pH differential between normal tissues and acidic regions of tumors. This was for the purpose of developing compositions which would be selectively sequestered in acidic areas of tumors. The resultant peptides were further adapted to both report the presence of tumors (for diagnostic use) and to kill the quiescent cells in acidic areas of tumors (for therapeutic use). These peptide compositions (now called "onco-tools") and their use for detecting and treating tumors are disclosed in two US patent applications submitted by the present inventor— one application is pending (Ser. No. 11/069,849) and one has been allowed but has not yet issued (Ser. No. 11/069,387). Neither has yet been published or otherwise disclosed to the public.

BRIEF SUMMARY OF THE INVENTION

The object of the present invention is to provide compositions and methods for detecting and treating tumors containing acidic areas.

In the present patent application the inventor discloses and claims extensions and improvements in the design, preparation, properties, applications, and methods of use of onco-tools, which comprise the inventor's own art which is described in two US patent applications previously submitted by the present inventor—one of which is pending (Ser. No. 11/069,849) and one of which has been allowed but has not yet issued (Ser. No. 11/069,387). Neither has yet been published or otherwise disclosed to the public.

The present patent application discloses major improvements and extensions in onco-tools, their component parts, and their methods of use. Notably, some of these improvements comprise a substantial evolution of the original onco-tool design such that now onco-tools also encompass novel non-peptide compositions. The improvements and extensions disclosed and claimed in the present patent application include:

1) additional peptide sequences and end structures which undergo the desired pH-mediated transition between an anionic hydrophilic form at pH 7.4 and a non-ionic lipophilic form in acidic areas of tumors;
2) advanced pH-switches, each of which exploits an internal H-bond that serves to raise the pH at which the structure switches between its high-pH hydrophilic form and its low-pH lipophilic form, and that also serves to increase the solubility differential between the two forms;
3) oligomers of advanced pH-switches which provide improved specificity by virtue of transitioning over a narrower pH range between the high-pH form which lacks affinity for tissues and the low-pH form which is sequestered in acidic areas of tumors;
4) advanced cargo components that have less impact on the solubility properties of the onco-tools, and which are more effective for binding the preferred radioisotopes;
5) a newly-selected radioisotope for much more effective killing of the treatment-resistant quiescent tumor cells;
6) an onco-tools-only method for killing the entire tumor, where an alpha-emitting radioisotope serves for effective killing of the treatment-resistant quiescent tumor cells in acidic areas of the tumor, and a beta-emitting radioisotope serves to kill the more vulnerable fast-dividing tumor cells in areas of tumors up to a few hundred microns from acidic areas; and,
7) an integrated method for detecting tumors and treating any tumors so detected.

BRIEF DESCRIPTION OF THE FIGURES:

FIG. 6 shows amino acid sequences and their axial distribution plots of peptide sequences unsuitable as pH-switches.

FIGS. 7a-7d illustrates lipophilic end groups used with earlier peptide pH-switches, and the pH at mid-point of membrane binding of each.

FIG. 8 Illustrates representative end structures for improved pH discrimination

FIG. 9 illustrates the pH-mediated transition between forms.

FIG. 10 shows calculated titration curves as a function of lipophilicities of the acid form.

FIG. 11a shows waters H-bonded to a conventional carboxylic acid in its salt and acid forms.

FIG. 11b shows waters H-bonded to an internal acid-specific H-bonding carboxylic acid in its salt and acid forms.

FIG. 12a illustrates a structure which forms an internal acid-specific H-bond.

FIG. 12b illustrates a structure which forms non-acid-specific H-bonds.

FIG. 13a shows representative ring structures suitable for advanced pH-switches.

FIG. 13b shows an unacceptable structure for advanced pH-switches.

FIG. 14 is a table demonstrating insulation of a carboxyl from inductive effects as a function of the number of carbons separating the carboxyl from the phenyl ring.

FIG. 15a illustrates an H-bond site which is open to solvent.

FIG. 15b illustrates an H-bond site which is partially shielded from solvent.

FIG. 16a is a table showing an H-bond donor and representative H-bond acceptors suitable for forming low-barrier H-bonds.

FIG. 16b illustrates representative advanced pH-switches with low-barrier H-bonds.

FIG. 17 shows representative core structures for advanced pH-switches.

FIGS. 18a and 18b illustrate structural variations in a structural optimization procedure.

FIG. 19a illustrates forms of an oligomeric onco tool with two advanced pH-switches.

FIG. 19b illustrates forms of an oligomeric onco tool with three advanced pH-switches.

FIG. 20a illustrates a dimeric advanced pH-switch structure.

FIG. 20b shows the n-octanol/buffer partitioning of a dimeric advanced pH-switch structure.

FIG. 21 illustrates onco tools with multiple advanced pH-switches.

FIG. 22 shows a conventional cargo component for large onco-tools.

FIG. 24 shows the steps in preparation of an onco-tool containing an improved peptide pH-switch component.

FIG. 26 illustrates a synthetic scheme for preparing a conventional cargo component.

FIG. 27 illustrates synthetic schemes for preparing several advanced cargo components.

FIG. 28 shows synthetic routes for preparing onco-tools containing a single advanced pH-switch component.

FIG. 29 shows a synthetic route for preparing an onco-tool containing two advanced pH-switch components.

FIG. 30 shows a synthetic route for preparing an onco-tool containing three advanced pH-switch components.

DETAILED DESCRIPTION OF THE INVENTION

Figure 1:
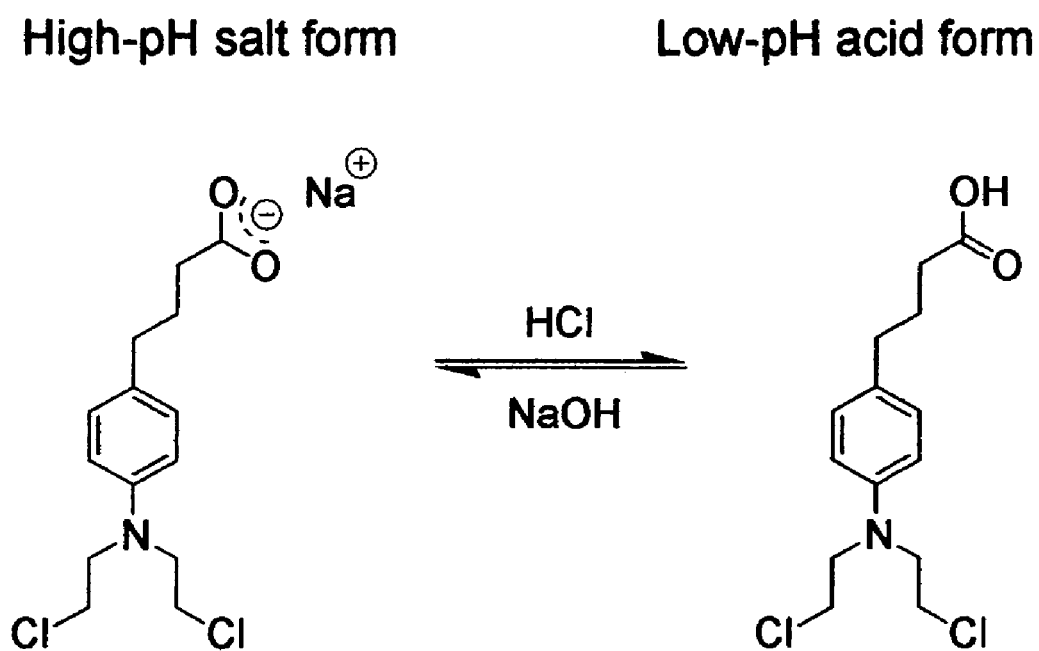
FIG. 1 shows the weak-acid chemotherapeutic, chlorambucil.

Overview of Onco-Tools for Detection and Treating Tumors

Three key terms used in describing these novel compositions and methods for detecting and treating tumors are defined as follows:

pH-Switch component means a component of an onco-tool wherein under physiological conditions at pH 7.4 substantially all of that component exists in an anionic hydrophilic form which has a very low affinity for tissues, but at the pH in an acidic area of a tumor a significant portion of that component switches to a non-ionic lipophilic acid form which is sequestered in the tumor by virtue of binding to extra-cellular elements and/or binding to cell surfaces and/or entering into cells.

Cargo component means a component of an onco-tool which serves to report the presence of the onco-tool and/or which serves to kill cells. The cargo component can exist in either of two forms. In the first form, referred to as the "effective-to-bind-a-radioisotope" form, the cargo component has a structure which is capable of readily binding to a selected radioisotope, but has not yet bound a radioisotope. An onco-tool with this effective-to-bind form of the cargo component is suitable for shipping and storage. In the second form a radioisotope is incorporated into the cargo component. An onco tool with this contains-a-radioisotope form of the cargo component is delivered into the patient for the purpose of detecting or killing tumors containing acidic areas.

Onco-Tool means a composition useful for detecting or treating tumors containing acidic areas, where that composition comprises at least one pH-switch component and at least one cargo component. A "diagnostic onco-tool" is an onco-tool that includes at least one cargo component effective to report the presence of the onco-tool to a detector outside the body. A "therapeutic onco-tool" is an onco-tool that includes at least one cargo component effective to kill cells.

A. Diagnostic Application of Onco-Tools

An ideal diagnostic for tumors should: a) be effective to detect a wide range of tumor types; b) be effective to detect even very small tumors; c) be effective to distinguish between tumor and all normal tissues; d) provide an adequate signal to noise ratio for decisive detection of tumors which are present; and, e) provide a suitable signal readily detected outside the body. Conventional tumor diagnostic reagents and methods typically can only detect tumors when the tumor is about 1 centimeter in diameter or larger, and such diagnostics are commonly not brought to bear until after the tumor has caused overt symptoms—by which time the tumor has often metastasized and/or caused irreversible organ damage. Further, because of the great variability between tumor types, and even between tumors similar in type, routine detection of tumors remains difficult and uncertain. In contrast to conventional tumor diagnostic reagents and methods, the inventor believes pH-switch-containing onco-tools, as described hereafter, can serve to effectively detect a wide range of tumor types at very early stages of tumor development, and can be effective for readily distinguishing even very small tumors from surrounding normal tissues.

a) Detect A Wide Range of Tumor Types

Much of the difficulty in routine early detection of tumors has been in identifying some property that is unique to tumors while also being common to a wide range of tumor types, and which can be readily exploited for routine, affordable, and non-invasive detection of tumors. With present tumor diagnostics a wide variety of tumor-associated properties are currently exploited, each for detecting one or a few of the many different types of tumors. In contrast, the acidity in the interstitial space of hypoxic areas of tumors appears to be virtually unique to tumors, as well as being common to a very wide range of tumor types. Therefore, a single composition designed to exploit such tumor acidity is expected to be effective for the detection of most, and possibly all tumor types.

b) Detect Even Very Small Tumors

Acidic regions in tumors typically begin to form when the tumors reach a size of about 1 millimeter in diameter. In this regard, it should be noted that a near-microscopic size tumor 1 millimeter in diameter has a volume about a thousand fold smaller than the volume of a tumor 1 centimeter in diameter, and a thousand-fold larger 1 centimeter tumor is about the current minimum detectable size for conventional tumor diagnostics. Thus, in contrast to current tumor diagnostics which can only detect tumors at a relatively late stage, a diagnostic which can successfully exploit the acidity of tumors for detection has the potential for detecting very small tumors well before they show overt symptoms, and probably well before they begin to metastasize or cause irreversible organ damage.

c) Distinguish Between Tumor and all Normal Tissues

In order for acidity in the interstitial space of hypoxic areas of tumors to serve as an adequate tumor-specific marker, the detected acidity needs to be essentially unique to tumors. However, there are several normal areas in the body which are at least as acidic as in tumors. Such low-pH areas in the normal body include the lumen of the stomach, often the urine, and muscles undergoing anaerobic metabolism during extreme exercise.

In regard to acidity in the stomach, a diagnostic onco-tool which has been seen to be sequestered in acidic areas of tumors in tumor-bearing mice, appears not to label stomach tissue in living mice to any significant extent (unpublished work). This suggests that such compositions, when distributed in the blood and the interstitial space of tissues, do not have significant access to the acidic lumen of the stomach.

In regard to acidic urine (which is in intimate contact with cells lining the proximal tubules of the kidney), there are safe and effective drugs available, such as Acetazolamide, which are known to render the urine basic (pH≧7.4). Thus, the urine of a person can easily and safely be maintained in a basic state for substantial periods of time—more than adequate for the few hours required for a tumor diagnostic procedure using a diagnostic onco-tool.

In regard to temporary acidity in muscles during anaerobic exercise, such acidity is easily avoided simply by not engaging in extreme exercise for several hours before and during the diagnostic procedure.

d) Achieve an Adequate Level of Sensitivity

In diagnostics utilizing radioisotopes, when one attempts to detect a very small tumor in a patient it is generally not too difficult to get enough radioisotope into the tumor to generate an adequate signal from that tumor. Instead, typically the greatest challenge is in avoiding excessive signal from the vastly more abundant normal tissues. While modern computer-aided scanning technologies afford greatly increased signal to noise ratios by allowing one to mathematically focus in on each of many small areas within the patient, nonetheless, even with the aid of such technologies it remains that in order to easily detect a small tumor in a reasonable period of time the diagnostic composition should be strongly sequestered in the tumor, and be largely absent from normal tissues.

To satisfy this selectivity requirement, onco-tools of the instant invention are designed such that at the pH present in normal tissues (pH 7.4) they exist predominantly in their anionic hydrophilic form which: a) has a very low affinity for tissues; and, b) favors rapid excretion from the body through the kidneys. Conversely, when the onco-tool enters an acidic area in a tumor it undergoes a pH-mediated transition to a non-ionic lipophilic form which is sequestered in the tumor. Design strategies for, structures of, and methods of use of compositions which provide such selectivity for acidic areas of tumors are described in two pending applications by the inventor, and improvements and extensions in such compositions and methods, developed by the same inventor, are detailed herein.

e) Provide Signal for Detection from Outside the Body

For diagnostic application, one has considerable latitude in selecting the one or more cargo components effective to generate a signal that can be detected from outside the body. Several radioisotopes with favorable properties for use in a cargo component include:

| Radioisotope | Half-life |
|---|---|
| technetium-99 | 6 hours |
| iodine-121 | 2 hours |
| iodine-123 | 13 hours |

B. Therapeutic Application of Onco-Tools

An ideal therapeutic for tumors should: a) be broadly effective against a wide range of tumor types; b) be effective against even very small tumors; c) be highly specific for tumors; and, c) be highly effective against all cells of the tumors, including both the relatively vulnerable fast-dividing cells and the treatment-resistant quiescent cells. While conventional therapies and combinations thereof, including radiation therapy, chemotherapy, and immunotherapy, fail by a large margin to satisfy these requirements, the inventor believes properly designed onco-tools, as described hereafter can effectively satisfy this challenging combination of stringent requirements.

a) Treat a Wide Range of Tumor Types

Similar to the case for tumor diagnostics, much of the difficulty in devising a treatment which is effective against a broad range of tumor types has been in identifying some property which is virtually unique to tumors while also being common to a wide range of tumor types, and which can be readily exploited for safe and effective treatment. In contrast to the wide diversity of tumor properties, each of which is which is exploited for treating one or a few of the many different tumor types, the inventor believes the acidity in the interstitial space of hypoxic areas of tumors, which appears to be common to most or all tumor types, can be exploited for the treatment of most, and possibly all tumor types.

b) Treat Tumors Having a Wide Range of Sizes

The same considerations which bear on the ability of diagnostic onco-tools to detect even very small tumors also apply to the ability of therapeutic onco-tools to treat tumors having a wide range of sizes—down to a near-microscopic 1 millimeter in diameter.

c) Avoid Significant Collateral Damage to Normal Tissues

As described in the earlier section on diagnostic application, there are several normal low-pH areas in the body where a therapeutic onco-tool might be sequestered, whereupon it could cause damage to surrounding normal tissues. As discussed earlier, it appears that the acidity in the lumen of the stomach is not a problem, and the possibility of low pH in muscles is easily avoided, and low pH of the urine is easily prevented by use of suitable safe and effective over-the-counter drugs.

d) Destroy the Entire Tumor

As noted earlier herein, conventional tumor therapies (radiation and chemotherapy) are reasonably effective in killing the relatively vulnerable fast-dividing cells near tumor capillaries, while those same conventional therapies are generally far less effective against the treatment-resistant quiescent cells in hypoxic/acidic areas more distant from tumor capillaries. Conversely, the onco-tools of the present invention are designed to be sequestered only in the acidic areas of tumors populated by treatment-resistant quiescent tumor cells. Thus, if the onco-tool is structured to be effective to kill the quiescent cells, then a combination of a conventional tumor therapy to kill the fast-dividing tumor cells, and a therapeutic onco-tool to kill the quiescent tumor cells should achieve complete killing of tumors—and probably with substantially less overall toxicity to the patient. This lesser toxicity is a consequence of being able to use a substantially lower dose of radiation or chemotherapeutic because one only needs it to kill the vulnerable population of fast-dividing tumor cells.

Figure 2:
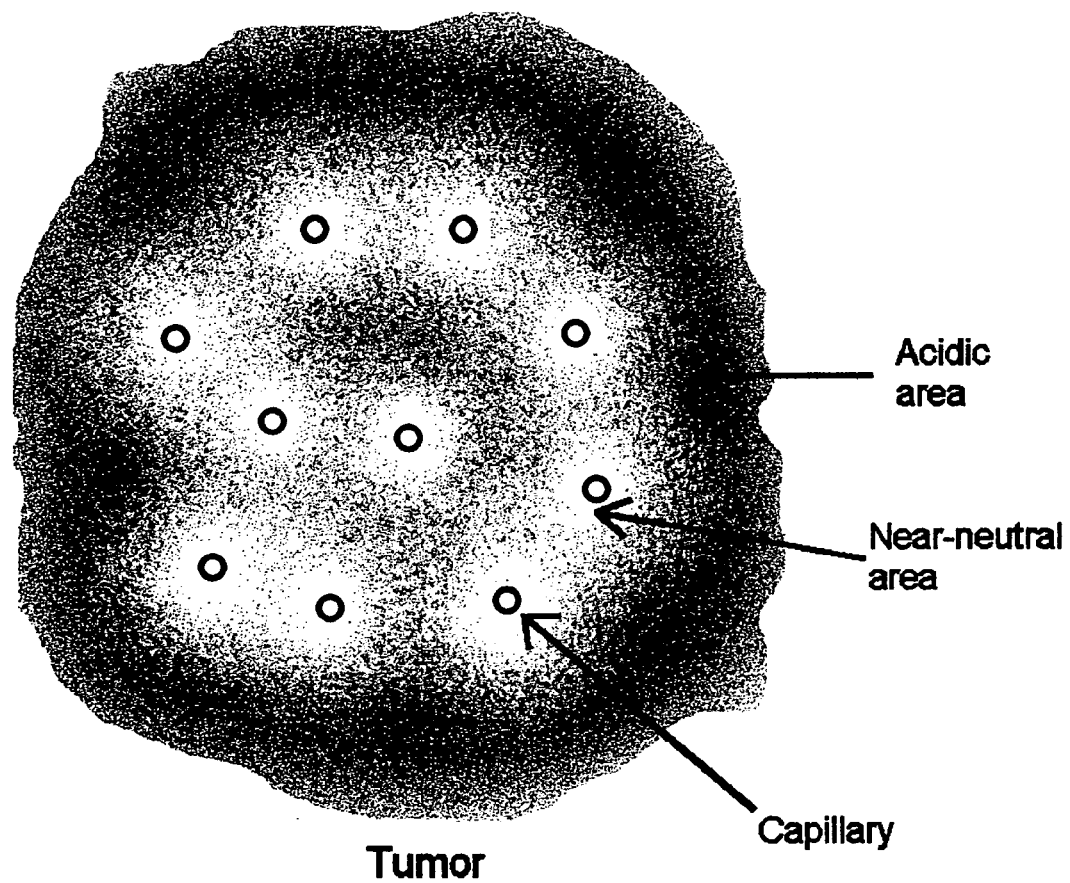
FIG. 2 illustrates the distribution of acidity in tumors.

While combining conventional tumor therapies with a therapeutic onco-tool offers the prospect of greater safety, higher efficacy, and fewer relapses than conventional therapies alone, the inventor has recently devised an improved therapeutic strategy which entails using only onco-tools. The key challenges in this improved onco-tools-only strategy are two fold. One challenge is to decisively and completely kill all the treatment-resistant quiescent tumor cells near or in which the onco-tool resides. The other challenge is to decisively and completely kill all the treatment-sensitive fast-dividing tumor cells, which may be positioned as far as about 50 to several hundred microns from tissue-associated onco-tool, as illustrated in FIG. 2.

The inventor believes these two challenges are best met by using onco-tools containing two or more different radioisotopes, where one of the radioisotopes serves to kill the radiation-resistant quiescent tumor cells and one or two of the radioisotopes serve to kill the radiation-sensitive fast-dividing tumor cells.

i) The radioisotope used to kill the radiation-resistant quiescent tumor cells should have an emission which releases a vast amount of energy over a very short distance (a few cell diameters), such that the released energy is highly effective to kill all of the radiation-resistant quiescent tumor cells near or in which radioisotope-carrying therapeutic onco-tool is positioned. Alpha-emitting radioisotopes appear to best satisfy this demanding requirement.

ii) The radioisotope used to kill the radiation-sensitive fast-dividing tumor cells does not need to have an emission which releases such a high density of energy along its path, but the radioisotope's emission does need to release its energy over a substantially longer path. This is because the emitting radioisotope will be positioned in the acidic area of the tumor while its emitted radiation needs to kill fast-dividing tumor cells close to tumor capillaries, and such fast-dividing cells can be as far as about 50 to several hundred microns from any acidic area of the tumor, and hence as far as about 50 to several hundred microns from any radioisotope-carrying therapeutic onco-tool. A beta-emitting radioisotope, or a combination of two or more different beta-emitting radioisotopes with differing path lengths, best satisfies this requirement.

DEFINITIONS OF TERMS USED IN THE SPECIFICATION AND CLAIMS

The terms used herein have the following specific meanings, unless otherwise noted.

pH-switch component: a structure for use in an onco-tool, which at the pH of normal tissues substantially all exists in an anionic hydrophilic form that has a very low affinity for tissues, but in acidic areas of tumors a significant portion of that structure switches to a non-ionic lipophilic form that has a high affinity for tissues.

Peptide pH-switch component: a pH-switch component which comprises
a peptide with the properties
i) a length from about 14 to about 50 amino acids;
ii) about 20% to about 38% of the amino acids are glutamic acids;
iii) the glutamic acid side chains are dispersed around the helical axis and along the length of the helical axis;
iv) at least 90% of the non-glutamic amino acids are lipophilic amino acids selected from the group consisting of leucine, isoleucine, norleucine, valine, methionine, and non-standard alpha amino acids of similar or greater side-chain lipophilicity;
v) at least one terminus of the peptide pH-switch is predominantly anionic and hydrophilic at pH 7.4, and predominantly non-ionic and lipophilic at pH 6.0;
vi) substantially all of the amino acids are of the same chirality.

Advanced DH-switch component: a pH-switch component which comprises
i) an aliphatic ring structure selected from the group consisting of a 4-membered ring, a 5-membered ring, and a 6-membered ring;
ii) a carboxylic acid moiety directly linked to the aliphatic ring structure;
iii) the carboxylic acid moiety is separated from any linked electron-withdrawing group by at least two carbons;
iv) an H-bond acceptor moiety selected from the group consisting of which is part of the aliphatic ring structure, which is directly linked to the aliphatic ring structure, and which is linked through one atom to the aliphatic ring structure;
v) the H-bond acceptor moiety in its non-ionic form has a structure which cannot serve as an H-bond donor moiety;
vi) the carboxylic acid moiety and the H-bond acceptor moiety are positioned and oriented so that they can form an internal acid-specific H-bond.

Cargo component: a structure for use in an onco-tool, where that structure has a form that is effective to bind a radioisotope, or a form that contains a radioisotope which is effective to report the presence of the onco-tool or is effective to kill cells.

Advanced cargo component: a cargo component which comprises:
(a) a structure selected from the group consisting of
i) an alkene,
ii) a 5-membered aromatic ring, and
iii) a 6-membered aromatic ring; and, (b) linked to that structure a moiety selected from the group consisting of
  i) effective to bind a halogen, and
  ii) consisting of a radiohalogen.

Onco-tool: A composition for detecting and/or treating tumors containing acidic areas, which comprises at least one pH-switch component and at least one cargo component.

Diagnostic onco-tool: An onco-tool for detecting tumors containing acidic areas, where said onco-tool contains a radioisotope effective to report the presence of the onco-tool.

Therapeutic onco-tool: An onco-tool for treating tumors containing acidic areas, where said onco-tool contains a radioisotope effective to kill cells.

Acidic areas of tumor: An area of a tumor where the interstitial space has a pH of less than 7.2.

Physiological conditions: An aqueous solution with a temperature in the range of 20 deg. C. to 40 deg. C. and having a sodium chloride concentration between about 0.13 M and 0.17 M.

Significant portion: Greater than about 2%.

Predominantly: Greater than about 75%.

Substantially all: Greater than about 95%.

Anionic/hydrophilic form: A form which carries a negative ionic charge and has an octanol/water partitioning coefficient of less than 0.3.

Non-ionic/lipophilic form: A form which does not carry an ionic charge and has an octanol/water partitioning coefficient of greater than 3.

Effective to bind a radioisotope: A form of a cargo component that has a structure which is capable of readily, efficiently, and stably binding a selected radioisotope, but which has not yet bound such a radioisotope.

Effective to report the presence: A radioisotope whose decay within a living subject, such as a human, generates an emission, such as a gamma ray, that can be readily detected from outside that subject.

Effective pKa: Defined herein as the pH value at the midpoint of the switch between the anionic hydrophilic form of a substance and the non-ionic lipophilic form of that substance, where that switch between the two forms is measured with the substance present at 20 milliMolar in aqueous physiological saline (or a close equivalent containing some buffer). While the effective pKa value closely resembles the pKa value for a substance, the effective pKa value is pertinent to substances whose acid form is strongly lipophilic and so can drop out of solution during titrations, and is a value measured in the presence of physiological saline—which has a significant impact when the acid form of the substance has limited aqueous solubility.

Present inventor: James E. Summerton, Ph.D.

DETAILED ASPECTS OF THE INVENTION

1. Peptide DH-Switches

Figure 3:
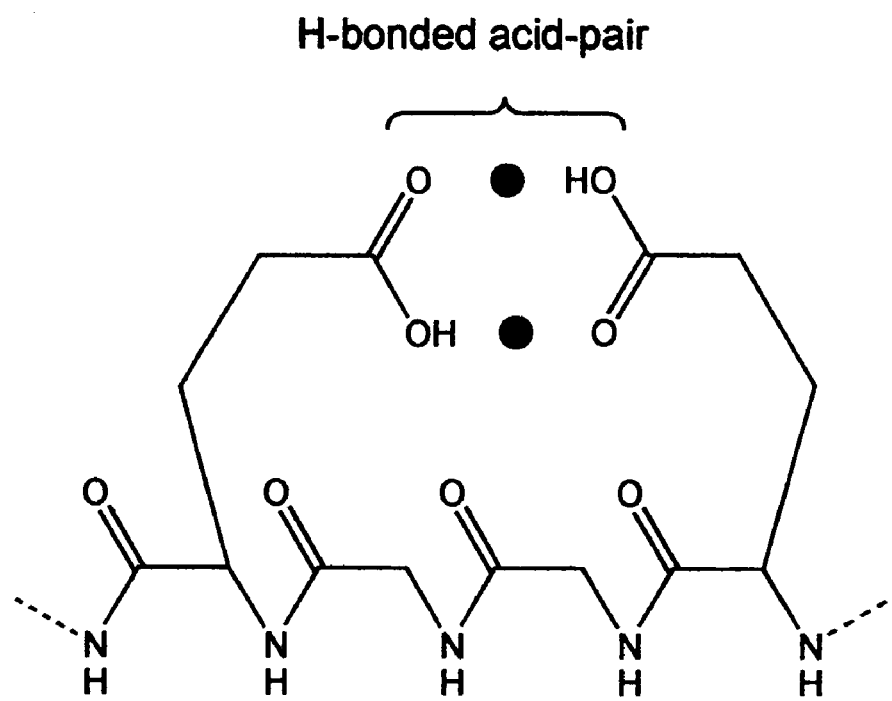
FIG. 3 illustrates the previously-postulated acid-pairs in peptides.

In the 1990s, the present inventor developed transporter peptides designed to convert to a non-ionic/moderately-lipophilic form at the pH within late-stage endosomes (about pH 5.0), and then pass through the endosomal membrane. As they enter the cytosol of cells they revert to their anionic/hydrophilic form at the neutral pH of the cytosol (Summerton & Weller, U.S. Pat. No. 6,030,941). In those high-acid-content transporter peptides the glutamic acid plus aspartic acid content ranged from 40% to about 100%. For all such transporter peptides it appeared that results from biophysical studies were compatible with the inventor's postulate that internal H-bonding was driving the acid-mediated transition to the low-pH form. Specifically, Summerton postulated that proximal carboxylic acid side chains were forming double-hydrogen-bonded acid-pairs when such peptides were in the low-pH form, and that it was this internal H-bonding, illustrated in FIG. 3, which was responsible for the unusually sharp pH-mediated transition between lipophilic and hydrophilic forms which occurred at a higher-than-expected pH in aqueous solution (typically between pH 5.0 and 6.0).

More recently the present inventor set out to develop related peptides which would be effective to meet the more demanding requirement of converting between an anionic/hydrophilic form at physiological pH (pH 7.4) and a non-ionic/lipophilic form at pH values present in acidic areas of tumors (pH 6.0 to 7.2, but predominantly between about pH 6.4 and pH 7.0). In that development effort the inventor found it necessary to restrict the acid side chains to only glutamic acids, and to reduce the glutamic acid content to less than 40% in the core repeating sequence (detailed in a pending patent application by the present inventor, U.S. patent application Ser. No. 11/069,387, allowed, but not yet published or issued). Still more recently, in the course of continuing investigations on these low-acid-content peptide pH-switches, the inventor prepared a peptide having a sequence that molecular modeling indicated could not form the postulated double-hydrogen-bonded acid-pairs illustrated in FIG. 3. The amino acid sequence and axial distribution plot of that non-acid-pairable sequence are shown in FIG. 4.

New Peptide pH-Switches

A. No Need of Positioning for Acid-Pair Formation

Figure 4:
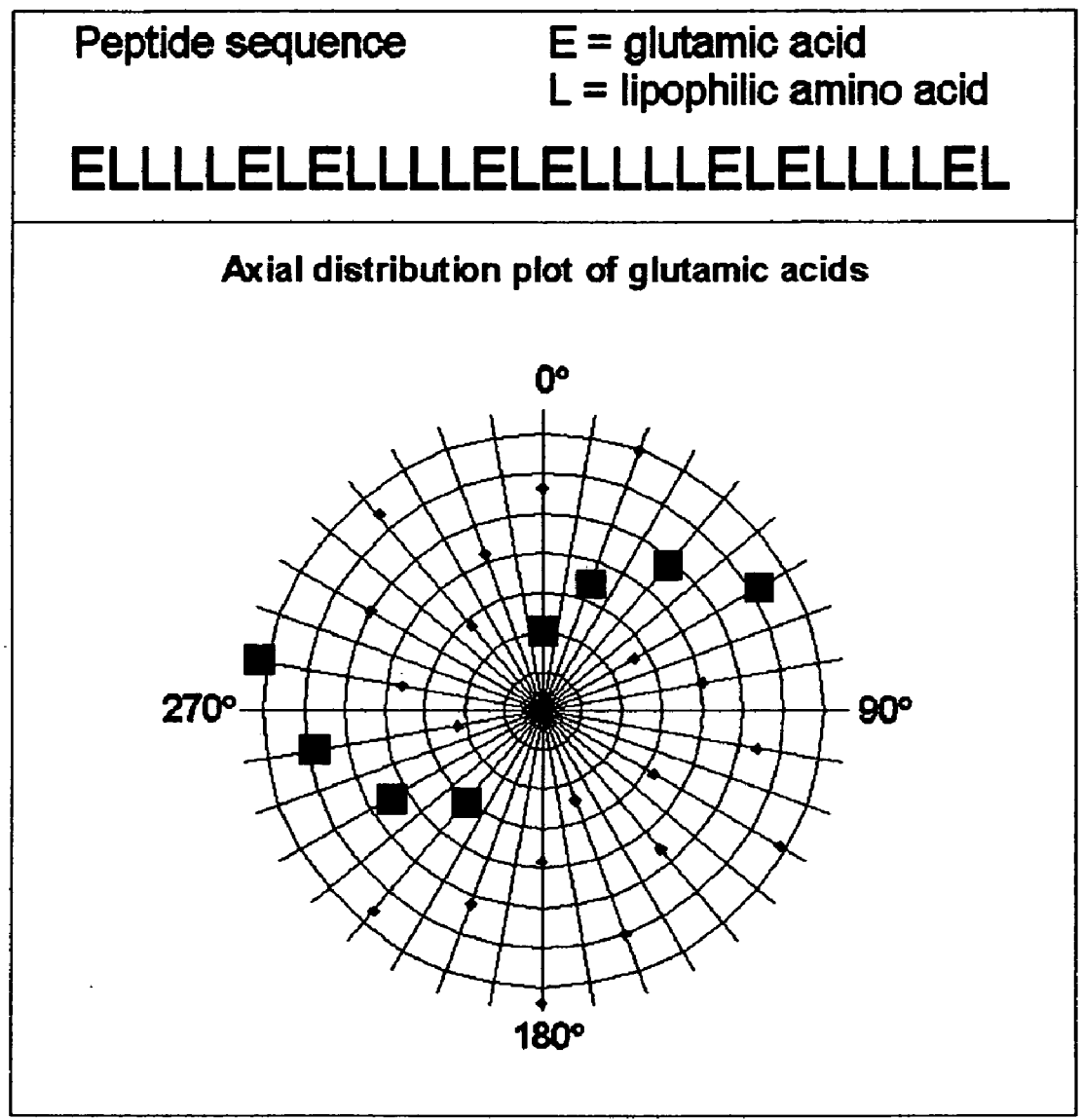
FIG. 4 shows a non-acid-pairable peptide sequence.
Figure 5:
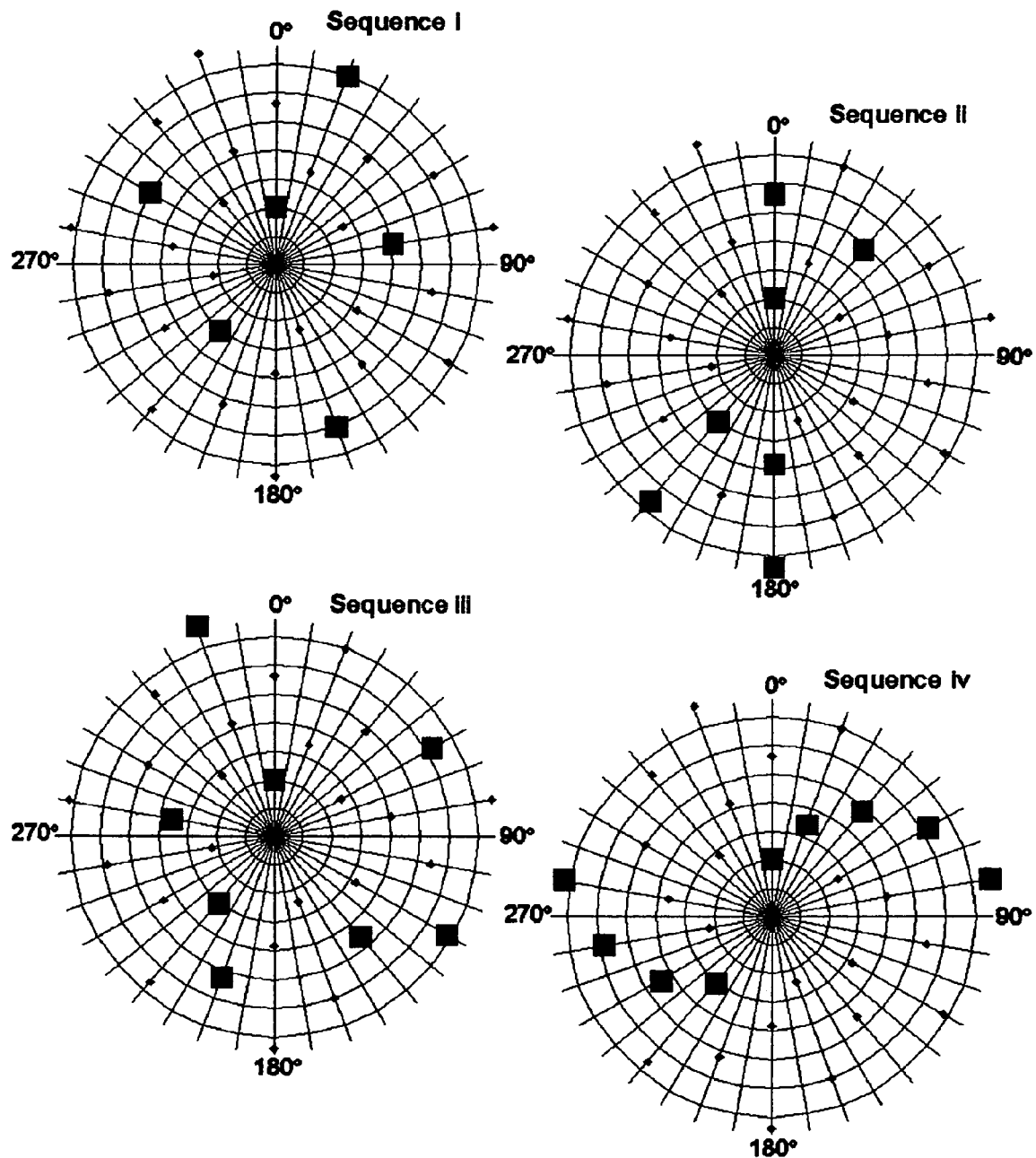
FIG. 5a shows preferred amino acid sequences for improved peptide pH-switches.
FIG. 5b shows axial distribution plots of glutamic acid side chains of the preferred amino acid sequences for improved peptide pH-switches.

Surprisingly, the peptide in FIG. 4, whose acid side chains cannot form the previously postulated double-hydrogen-bonded acid-pairs, was found to exhibit a transition which is as sharp and occurs at about as high of a pH as similar-composition sequences where the glutamic acid side chains were properly positioned to form the postulated double-hydrogen-bonded acid-pairs. This finding demonstrates that positioning of the acid side chains for hydrogen-bonded pairing of their carboxyl moieties is not necessary in order for a peptide pH-switch to undergo a relatively sharp pH-mediated transition at a pH greater than 6.0. In fact, experimental results have been published elsewhere which could lead one to conclude that those previously postulated double-H-bonded acid pairs probably never form in aqueous solution (Rebec et al., J. Amer. Chem. Soc. vol 108 pages 6068-6069 (1986)). Thus. the inventor now recognizes that the previously-postulated acid-pair formation is not necessary, and probably never occurs in peptide pH-switches in aqueous solutions. Peptide sequences i and iv of FIG. 5 illustrate sequence types which have only non-pairable carboxyls, and some of the peptide sequences of sequence types ii, iii, and v of FIG. 5 contain at least some non-pairable carboxyls.

B. Carboxyls Well Dispersed Around and Along Peptide Helical Axis

Figure 5B:
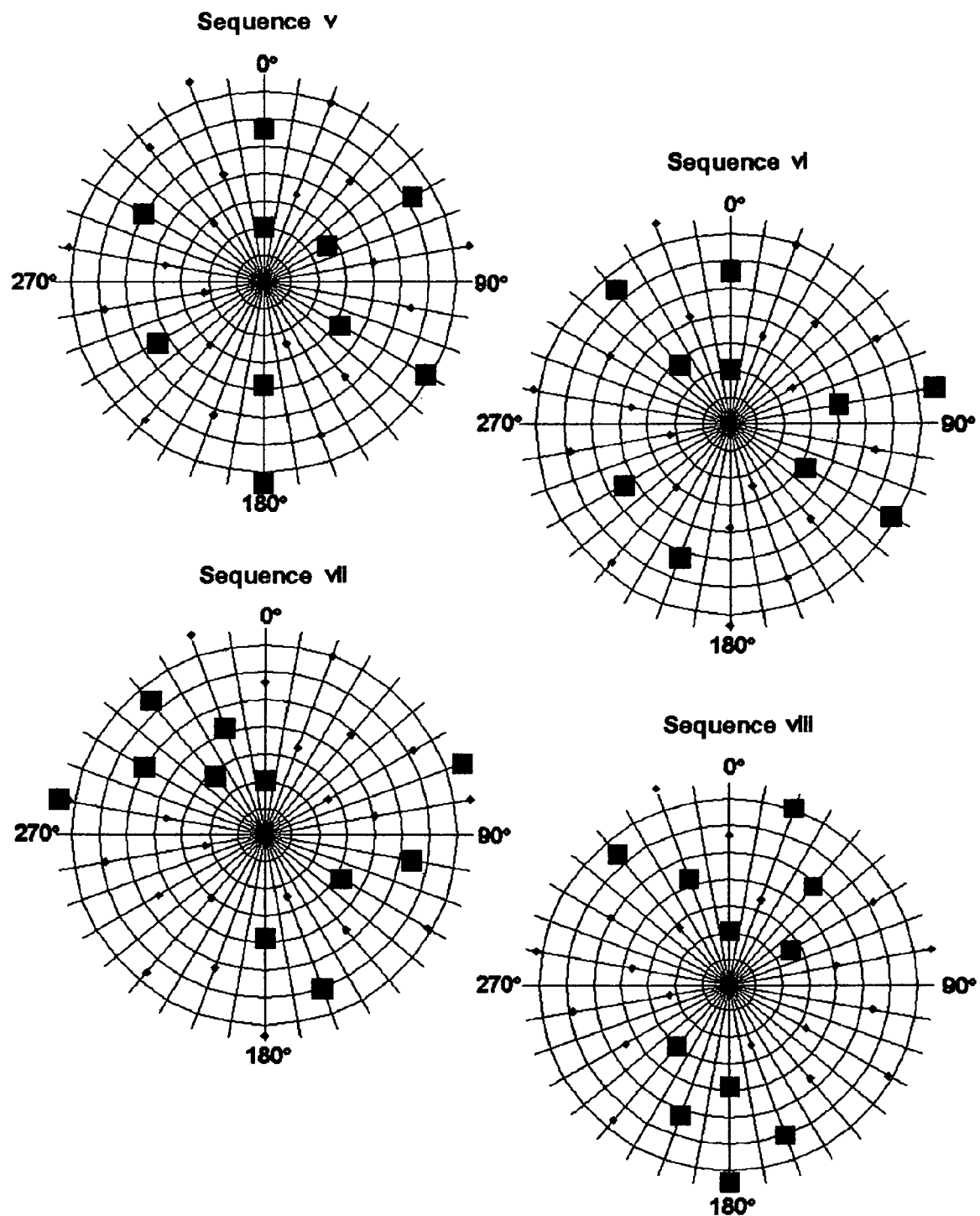

The previously determined requirement remains that the glutamic acid side chains not be congregated on one face or at one end of the peptide's alpha helix, but instead the carboxyl side chains should be well dispersed around the helical axis and along the helical axis. This is essential in order to avoid lipophilic patches of a size sufficient to cause aggregation of the peptide, or sufficient to cause tissue binding by the peptide when that peptide is in its anionic form at pH 7.4. FIG. 5a shows 8 core repeating sequence types which have been found to have adequate dispersion of carboxyls around and along their helical axis, and FIG. 5b shows the axial and longitudinal plots of the carboxyls for selected peptide lengths. Conversely, FIG. 6 shows the corresponding plots for two peptides which have poorly dispersed carboxyls. As expected, these latter two peptides also exhibit poor solubilities in aqueous solution at neutral pH.

It is noteworthy that in the absence of the earlier limitation of having to position glutamic acid side chains for acid-pair formation one gains significant latitude for selecting sequences wherein those glutamic acid side chains can have an improved distribution around and along the helical axis of the peptide. As noted above, peptide sequences i and iv of FIG. 5 constitute such sequences with carboxyl side chains which are both non-pairable and well dispersed around and along the helical axis. Notably, such peptides containing non-pairable carboxyls have been found to exhibit good aqueous solubilities at neutral pH and high lipophilicity at pH values found in acidic areas of tumors.

C. Avoid Terminus Which Remains Lipophilic at pH 7.4

Conventional peptides having core repeating amino acid sequences suitable for use as a pH-switch exhibit poor binding to tissues when such peptides are in their low-pH form. This is because in the critical pH range between 6.0 and 7.2 their ends remain ionic and hydrophilic. To remedy this, in earlier peptide pH-switches the inventor added a structure to at least one end of the peptide which rendered that end non-ionic and lipophilic. Such added end structures, which have been referred to as entry ends in pending patent applications, have been shown to be effective in raising the pH at which a peptide pH-switch binds to isolated cell membranes. FIG. 7 shows several representative end structures, all with the same core peptide sequence, along with the respective experimentally-determined mid-point pH values for their binding to isolated cell membranes. The progressive increase in the mid-point pH values seen with increasing lipophilicity of the end structure demonstrates that by using a relatively lipophilic end structure one can achieve a desirable increase in the pH at which the peptide binds to cell membranes.

While these added end structures were found to give a desirable increase in the pH at which the peptide pH-switches bind to isolated cell membranes, nonetheless, in more recent studies in tumor-bearing mice it was found that adding an excess of lipophilic groups at the end of the peptide, particularly as in structure (d) of FIG. 7, caused the peptide to bind to both tumors and normal tissues. This suggests that the lipophilic end structure is dominating the association of the pH-switch with tissues, and because that end structure is equally lipophilic at both the acidic pH in tumors and the neutral pH of normal tissues, peptides with such lipophilic end groups lack the crucial property of not binding to tissues at the pH of normal tissues.

Thus, in earlier work it was found that increasingly lipophilic end modifications appeared to be desirable in order to give a higher and more practical level of tissue binding in acidic areas of tumors However, more recent studies have shown that end structures which remain non-ionic and lipophilic at pH 7.4 also cause unacceptable binding to normal tissues in tumor-bearing mice.

D. Improved End Structures Giving Better Discrimination Between Tumor and Normal In view of the problem presented by the earlier peptide end structures that remain non-ionic and lipophilic at pH 7.4, and based on recent experimental work, the inventor has concluded that in order to avoid binding to normal tissues at pH 7.4 a carboxylic acid-containing group should be positioned at or within one amino acid from at least one of the peptide ends, and the carboxyl of that group should have a pKa value greater than about 4.5. While this terminal or near-terminal carboxyl helps avoid binding to tissues at neutral pH, steps must also be taken to assure that peptide end is largely non-ionic and lipophilic at the reduced pH found in acidic areas of tumors. This can be achieved by selecting the peptide sequence such that at least one, but preferably four, of the amino acids contiguous to that carboxylic acid-containing terminal group are lipophilic amino acids selected from the group consisting of leucine, isoleucine, norleucine, valine, methionine and non-standard alpha amino acids of similar or greater side-chain lipophilicity. It is also important to avoid a peptide terminus which remains largely ionized at the reduced pH found in acidic areas of tumors. Typically this can be achieved by capping the peptide end with a moderately lipophilic moiety, such as a pivalate on the N-terminus, or a butyl amine on the C-terminus. FIG. 8 shows several representative peptide end structures which satisfy these new guidelines for the end structure of peptide pH-switches.

E. Preferred Peptide pH-switch Sequences

The inventor recently prepared and tested a variety of new peptide sequences, now without the sequence constraints imposed by the previously postulated need to position glutamic acid side chains for acid-pair formation. Results from these tests show that peptides with non-pairable carboxyls can serve as effective pH-switches. Results also indicate that to avoid unwanted binding to tissues at pH 7.4 at least one peptide terminus should have a carboxylic acid moiety positioned at or within one amino acid of the end, where that end carboxylic acid has a pKa value of 4.5 or greater. From such test results with the new peptides the inventor has developed more comprehensive guidelines for effective peptide pH-switches, as follows:

i) a length from about 14 to about 50 amino acids;

ii) about 20% to about 38% of the amino acids are glutamic acids;

iii) the glutamic acid side chains are not congregated on a face or an end of the alpha helix, but instead are dispersed around the helical axis and along the length of the helical axis;

iv) at least 90% of the non-glutamic amino acids are lipophilic amino acids selected from the group consisting of leucine, isoleucine, norleucine, valine, methionine, and non-standard alpha amino acids of similar or greater side-chain lipophilicity;

v) at least one terminus of the peptide pH-switch is largely anionic and hydrophilic at pH 7.4, and predominantly non-ionic and lipophilic at pH 6.0 by virtue of having a carboxylic acid-containing group positioned at or within one amino acid from the end of the peptide, with that end carboxyl having a pKa value greater than about 4.5, and by virtue of having at least one, but preferably four, lipophilic amino acids between that end carboxyl and the next glutamic acid in the peptide sequence;

vi) substantially all of the amino acids are of the same chirality.

Based on these design guidelines for improved peptide pH-switches, eight preferred core repeating amino acid sequences have been identified. FIG. 5a shows these preferred core repeating amino acid sequences, and FIG. 5b shows respective axial distribution plots for such peptides having selected lengths.

These core repeating sequences are all lower in glutamic acid content than the related prior art peptide sequences disclosed in U.S. Pat. No. 6,030,941, and this lower glutamic acid content serves to significantly raise the pH at which these peptides switch between their anionic and non-ionic forms. The corresponding higher content of lipophilic amino acids in the sequences of FIG. 5 also serves to increase the lipophilicity of the peptides' non-ionic forms. These eight core repeating sequences shown in FIG. 5 provide good dispersion of the glutamic acid side chains around and along the peptide's helical axis, and this in turn affords good aqueous solubility and little or no binding to biological structures at pH 7.4.

Note that core peptide sequences i and iv in FIG. 5 have acid side chain distributions which are incompatible with forming any of the previously-postulated doubly-hydrogen-bonded acid pairs. It is also noteworthy that many of the core repeating peptide sequences in FIG. 5 are incompatible with forming at least some of the postulated doubly-hydrogen-bonded acid pairs previously believed to be essential for effective pH-switch activity. As a consequence, many of the sequences in FIG. 5 differ in one or more particulars from peptide sequences previously disclosed and claimed in the inventor's pending patent applications, Ser. No. 11/069,387 and Ser. No. 11/069,849. This divergence from the previously claimed sequences in the pending applications arises because the new sequences in FIG. 5 of the present patent application were not designed within the constraints for being able to form the previously-postulated acid pairs, and so many of the new sequences in this current application fail to satisfy those earlier limitations on allowable sequences. Nonetheless, peptides with these new sequences shown in FIG. 5 have been found to exhibit a suitable pH-mediated transition between anionic and non-ionic forms.

It should be noted that some of the previous peptide pH-switch sequences disclosed and claimed in the inventor's pending patent applications, Ser. No. 11/069,387 and Ser. No. 11/069,849, are a subset of the new peptide pH-switch sequences in FIG. 5 of the present patent application. This is because the old sequences were selected with the limitation of pairable carboxyls, but because of insight gained from recent experimental work, the new sequences of FIG. 5 were designed without this limitation of pairable carboxyls.

2. Advanced DH-Switches

In an effort to further increase sequestering of peptide onco-tools in acidic areas of tumors while avoiding sequestering in normal tissues, the inventor recently began efforts to devise even more advanced structures which could be added to the end of a peptide onco-tool to increase its effectiveness. It was hoped that such structures could be designed to undergo the desired pH-dependant shift between anionic and non-ionic forms at a substantially higher pH than is typical of carboxylic acids. It was also hoped that such structures might also be designed so as to provide a particularly large shift in the hydrophilicity/lipophilicity properties between the two forms—which was expected to increase the onco-tools' discrimination between normal tissues and acidic areas of tumors. It was also envisioned that such structures might serve on their own as advanced pH-switches which could be combined with a suitable cargo component to serve as improved onco-tools for detection and treatment of tumors—with no need for a peptide component.

As with the peptide pH-switches, the key challenge in developing such an advanced pH-switch is to devise a structure which at pH 7.4 is anionic and hydrophilic, but then a significant portion switches to a form which is non-ionic and lipophilic at a pH present in acidic areas of tumors, and preferably at a pH as high as about 6.4 to 6.8. To obtain a quantitative measure of how lipophilic the non-ionic form of the pH-switch should be, mathematical modeling was carried out to calculate the pH-dependent transition between forms for a weak-acid substance which exists at high pH in an anionic water-soluble form, [A-], and which converts at a lower pH to a non-ionic lipophilic form which has some aqueous solubility, [HA sol], and which can also become water-insoluble by virtue of precipitating or oiling out, or binding to tissue components, or partitioning into a lipophilic phase such as octanol or a cell membrane. This insoluble fraction is denoted [HA insol]. The inter-conversions of these three forms, along with the key equations used in the mathematical modeling, are shown in FIG. 9.

The results from that modeling, shown in FIG. 10, suggest that the pH of the transition between the salt and acid forms is effectively raised by about 1 pH unit for each 10-fold increase in the octanol/water partitioning coefficient of the non-ionic lipophilic acid form. However, such an increase only applies after the non-ionic form reaches the lipophilicity threshold effective to initiate precipitation or tissue binding or partitioning into a non-polar phase. Example 1 describes titration assays which demonstrate this mathematically-predicted impact of the lipophilicity of the non-ionic form on the pH-dependent transition between the anionic form and the non-ionic form.

In light of the impact increased lipophilicity of the non-ionic form can have on the pH of the transition between the anionic and non-ionic forms of a substance, it appeared that it should be possible to devise a structure which would show an increased ability to discriminate between tumors and normal tissues by designing it in such a manner that the structure's non-ionic form is more lipophilic than is the case for conventional carboxylic acids. Accordingly, the inventor recently began a quest to devise structures explicitly designed to undergo a greater pH-dependant shift in their hydrophilicity/lipophilicity ratio than is the case for conventional carboxylic acids.

A. Internal H-Bond for Increased pH of Transition and Greater Solubility Differential With the objective of increasing the sequestering of onco-tools in tumors and improving their discrimination between tumor and normal tissues, the inventor postulated that an exceptionally large shift in the hydrophilicity/lipophilicity ratio between the anionic and non-ionic forms might be achieved with a structure which can form an internal hydrogen bond. In regard to this predicted enhanced shift in the hydrophilicity/lipophilicity ratio between the anionic and non-ionic forms for such an internally-H-bonding structure, FIG. 11a illustrates the expected waters of hydration directly H-bonded to a conventional carboxyl in its anionic form and in its non-ionic form, and FIG. 11b illustrates corresponding expected waters of hydration directly H-bonded to the anionic and non-ionic forms of a postulated structure effective to form the desired internal H-bond.

Clearly, both the conventional carboxyl and the carboxyl effective to form an internal H-bond lose their counter-ion in going from the anionic form to the non-ionic form. However, while the conventional carboxyl is expected to have the same number of waters directly H-bonded in both the anionic form and the non-ionic form, the inventor believes that for a carboxyl able to form an internal H-bond there will be a net loss of several (probably two) directly-H-bonded waters when going from the anionic form to the non-ionic form. The inventor postulated that this loss of about two waters of hydration should afford an enhanced shift in the hydrophilicity/lipophilicity ratios for the anionic and non-ionic forms, relative to this ratio for a similar structure which does not form such an internal H-bond. The inventor also postulated that such an internal hydrogen bond should favor the transition to the non-ionic form, resulting in an increase in the pKa value for the carboxylic acid moiety of the structure. These factors were predicted to cause a significant increase in the effective pKa value for advanced pH-switches capable of forming an internal H-bond in aqueous solution.

Conventional wisdom among experts in hydrogen bonding typically holds that a lone hydrogen bond will not be stable in an aqueous environment because of competition with water's vast concentration of H-bond acceptor sites (110 Molar) and H-bond donor sites (110 Molar). Instead, it is generally believed that a stable non-covalent interaction in aqueous solution requires a multiplicity of interactions, selected from H-bonds, hydrophobic interactions, and electrostatic interactions. The difficulty of forming H-bonds in an aqueous environment is further evidenced by the inventor's previously discussed apparent failure to achieve H-bonded acid-pairs of the type shown in FIG. 3.

Nevertheless, the inventor suspected that, contrary to the conventional wisdom, it might be possible to devise compact structures which will form a single relatively stable pH-dependent intramolecular H-bond in aqueous solution, where that H-bond serves to favor the non-ionic form over the anionic form, and serves to increase the lipophilicity of the non-ionic form. The inventor predicted that the combination of these two factors should result in a significant increase in the effective pKa of the carboxylic acid moiety. The crucial question then was: could practical structures be devised which would form such a postulated internal H-bond in aqueous solution?

After considerable experimentation, novel structures have been devised which appear to form the desired single pH-dependent intramolecular H-bond in aqueous solutions. As predicted, relative to the case for a conventional carboxylic acid, a pH-switch which can form this internal H-bond appears to undergo a significantly increased shift in hydrophilicity/lipophilicity in going from the anionic form to the non-ionic form. Such an H-bonding pH-switch also exhibits an increase in the pH at which the structure switches between its anionic/hydrophilic non-tissue-binding form and its non-ionic/lipophilic tissue-binding form. In light of this success, which is detailed later herein, the inventor uses the term "advanced pH-switch" to mean a pH-switch which is effective to form a pH-dependent internal H-bond in aqueous solution, where that internal H-bond raises the pH at which the structure switches between its anionic and non-ionic forms, and also enhances the hydrophilicity/lipophilicity differential between the two forms of the advanced pH-switch.

Results from molecular modeling and from experimental work detailed in the examples provided later herein suggest that the following three properties are essential in order for an advanced pH-switch to form a suitable and adequate internal H-bond in aqueous solution.

a) Acid-specific H-bond

The structure must contain a carboxyl moiety which is positioned in suitable proximity to an H-bond acceptor moiety for formation of an H-bond. When that carboxyl moiety is in its acid form it must serve as the H-bond donor, and the proximal H-bond acceptor moiety must be such that in its non-ionic form it can only serve as an H-bond acceptor, and cannot serve as an H-bond donor. The inventor refers to an H-bond formed by such a structure as an "internal acid-specific H-bond." FIG. 12a shows a structure which can form only an internal acid-specific H-bond. Conversely, FIG. 12b illustrates a similar, but unacceptable structure which can form both an internal H-bond when the carboxyl is in its acid form and an internal H-bond when the carboxyl is in its salt form. The inventor calls this dual H-bonding capability "internal non-acid-specific H-bonding," and his experimental results indicate that such non-acid-specific H-bonding is unacceptable because it fails to provide a significant increase in the effective pKa value, and it fails to afford the desired increase in the lipophilicity of the acid form. Example 2 describes experimental evidence that in acidic conditions the structure in FIG. 12a forms an internal acid-specific H-bond in aqueous solution, as well as evidence that said internal acid-specific H-bond causes a desired increase in the pH of the transition between salt and acid forms. This same example also shows that the very similar structure in FIG. 12b, designed to form non-acid-specific H-bonds, fails to provide a desired increase in the effective pKa value, nor does its acid form show the dramatic aqueous insolubility (lipophilicity) seen with the acid-specific internal H-bonding structure in FIG. 12a.

b) Minimal Conformational Freedom Between H-bonding Moieties

The H-bond acceptor moiety and the carboxyl serving as the H-bond donor moiety should be held in close proximity by a structure which has minimal conformational freedom. This limited conformational freedom can be achieved by using a suitable ring structure. Molecular modeling and experimental work suggests that 4-membered, 5-membered, and 6-membered aliphatic rings are preferred for this purpose. FIG. 13a shows representative 4-membered, 5-membered and 6-membered aliphatic ring structures which allow only very limited conformational freedom between the H-bond donor (OH of the carboxylic acid) and suitably-positioned H-bond acceptor moieties. Conversely, FIG. 13b shows a somewhat similar structure which is unacceptable because its acyclic structure allows excessive conformational freedom between the H-bond donor and H-bond acceptor moieties. Example 3 describes experimental evidence showing that a structure with minimal conformational freedom between H-bonding moieties can afford the desired increase in the effective pKa value, while a similar structure with substantially greater rotational freedom between H-bonding moieties fails to provide that desired increase in the effective pKa value—and so is presumably failing to form an adequately stable internal acid-specific H-bond.

c) Carboxyl Insulated from Inductive Effects of Electron-withdrawing Group

The carboxylic acid which is to serve as the H-bond donor moiety should be separated from any linked electron-withdrawing group by at least two, and preferably three or more carbons. This avoids any substantial reduction in the pKa value of that carboxyl due to inductive effects from electron-withdrawing groups. The molecular structures and their corresponding pKa values shown in FIG. 14a illustrate how an increasing number of aliphatic carbons can progressively insulate a carboxyl from the pKa-reducing effects of a phenyl group. FIG. 14b shows a structure wherein inductive effects from the proximal amide moiety causes an undue reduction in the pKa of the carboxylic acid moiety. Example 4 describes experimental evidence indicating that even with minimal conformational freedom between H-bond donor and acceptor moieties, if there is inadequate insulation of the carboxyl from inductive effects the pH of the transition between salt and acid forms will be too low to be useful in a pH-switch.

In addition to the above 3 essential properties, it appears that at least one additional property, selected from the following two properties, is desirable to assure formation of an adequate internal H-bond in aqueous solution.

d) Lipophilic Groups Partially Shielding H-bonding Site

A principal challenge in forming a lone H-bond in an aqueous environment is to preferentially form that H-bond in the presence of the vast concentration of competing H-bond donors and H-bond acceptors of the surrounding water. Based both on biochemical studies of enzyme catalytic sites and on the inventor's molecular modeling, the inventor postulated that the desired intramolecular H-bond might be more favored if the H-bonding site were partially shielded from the bulk water by the presence of lipophilic groups. FIG. 15 shows two structures, one where the H-bonding site is more open to the solvent, and the other where that H-bonding site is partially shielded from the solvent by an adjacent methyl group. Subsequent syntheses and titration studies, detailed in Example 5, provide evidence for the value of such partial shielding from the solvent as a means for favoring the desired intramolecular H-bond.

e) Low-barrier H-bond

The term "low-barrier H-bond" is used herein to mean a non-covalent bond formed between an H-bond donor moiety and an H-bond acceptor moiety, where the pKa values of the two isolated moieties are within about 2 pH units of each other. It should be noted that this definition includes what may also be construed as an internal salt where the hydrogen is closer to the acceptor moiety than to the donor moiety. Such low-barrier H-bonds are generally found to be exceptionally strong and so can appreciably favor the desired intramolecular H-bond in pH-switches. FIG. 16 shows several H-bonding moieties which are appropriate for forming low-barrier H-bonds in advanced pH-switches, and also illustrates several representative pH-switch structures containing appropriate H-bonds of the low-barrier type. Example 6 describes the synthesis and testing of a representative pH-switch (the N-oxide of N-propylisonipocotic acid), along with experimental evidence for formation of the desired low-barrier H-bond in aqueous solution.

B. Structural Optimization

As noted previously, the crucial requirements for both a peptide pH-switch and an advanced pH-switch are that the structure's anionic form be sufficiently hydrophilic that it has very little affinity for tissues, while its non-ionic form be sufficiently lipophilic that it is effectively sequestered in tissues. While the internal acid-specific H-bond of an advanced pH-switch, detailed above, makes a substantial contribution to meeting these two requirements, it is also generally necessary to further optimize the structure of a prospective advanced pH-switch to optimally meet these requirements.

The essential challenge in optimizing an advanced pH-switch is to incorporate into the structure sufficient lipophilic groups (generally alkyl groups) to give an adequately high effective pKa value, without introducing so many lipophilic groups that one gets undue tissue binding at pH 7.4. While molecular modeling on a computer with commercially-available modeling programs can provide some guidance toward such optimization, efforts along this line to date suggest that most computer-generated predictions relating to pH-dependent properties in aqueous solutions are of limited accuracy. It is particularly difficult to model the solubility properties of a weak-acid substance whose acid form is quite lipophilic, and wherein there is a substantial concentration of salt in the aqueous solution. Thus, it is generally necessary to design and synthesize a series of closely related structures and then empirically assess their properties in appropriate test systems.

One simple design approach that has provided useful guidance in such optimizations entails first drawing a prospective advanced pH-switch structure designed to form an internal acid-specific H-bond. FIG. 17 shows a number of representative core structures which properly position H-bond donor and acceptor moieties. Next, one counts the number of non-polar hydrogens exposed to the solvent, and counts the number of expected H-bonding sites in the acid form of that structure. The inventor's past experience suggests that the ratio of non-polar hydrogens to H-bonding sites should range from a minimum of about 3.0 to a maximum of about 7.0, and preferably be in the range of about 4.0 to about 6.0. Generally, it is desirable to design a series of related structures with various non-polar alkyl groups added so as to give multiple structures having ratios of non-polar hydrogens to H-bonding sites within the preferred range. It is also desirable that the added alkyl groups be selected and positioned so that subsequent syntheses will not require excessive effort. This approach is illustrated in FIG. 18 for two core pH-switch structures.

In regard to initial testing of prospective advanced pH-switch structures, a simple pH titration in physiological saline is fast and easy and provides useful information about the key properties one is attempting to achieve. A recommended initial test method is described later herein in Section 8 titled: Testing pH-switches and onco-tools, Part A, Titration assays. It is also desirable to carry out a study of the pH-dependent partitioning between n-octanol and aqueous buffers ranging from pH 5 to pH 8, as described in Section 8, Part B.

As noted previously, the internal acid-specific H-bond in an advanced pH-switch structure is predicted to contribute to an increase in the effective pKa value by two mechanisms: 1) formation of the acid-specific H-bond which directly favors formation of the acid form; and, 2) loss of two waters of hydration during formation of said H-bond causing a substantial increase in the lipophilicity of the H-bonded acid form, which then precipitates or oils out or partitions into a lipophilic environment such as cell membranes. It is of interest to be able to estimate the relative contributions of each of these two mechanisms for a given advanced pH-switch structure. In this regard, it has been found that when one slowly titrates the salt form of a substance whose acid form precipitates or oils out of aqueous solution then one obtains a skewed titration curve with an apparent pKa value appreciably higher than would be expected for such a structure, relative to the titration curve for a similar substance where both the salt and acid forms are fully water soluble. This lipophilicity/insolubility effect is best seen when one plots the first derivative of the titration curve, wherein one commonly sees substantial asymmetry and a shift to higher pH values in the titration plot in a case where the acid form is aqueous insoluble. In contrast, one sees a fully symmetrical titration plot at normal pH values for the case where both salt and acid forms are fully water soluble, such as for propionic acid. This lipophilicity/insolubility effect on the titration plot is seen both for substances which cannot form an internal acid-specific H-bond, such as octanoic acid, and for substances which can form an internal acid-specific H-bond, such as the advanced pH-switch structure shown in FIG. 12*a*.

Luckily, this lipophilicity/solubility effect can be avoided by titrating in a mixed solvent where both the salt and acid forms are fully soluble. A 1:1 mix of methanol and water generally serves for this purpose. In this solvent the first derivative titration curves again become symmetric. In the case of a substance which cannot form a stable internal H-bond, such as octanoic acid, the titration plot now shows a classical pKa value very similar to that seen for a fully water soluble acid, such as propionic acid. However, in the case of a substance believed to form a stable internal acid-specific H-bond, such as the advanced pH-switch structure in FIG. 12*a*, while the titration plot does become symmetric in methanol/water, nonetheless, the titration plot of such an internal acid-specific H-bonding substance still shows a substantially increased pKa value relative to a very similar structure, such as the structure in FIG. 12*b*, which cannot form an internal acid-specific H-bond.

The above suggests that in titrations in physiological saline the total increase in the apparent pKa value, accompanied by asymmetry in the titration curve, is due to a combination of the H-bond effect plus the lipophilicity/solubility effect described earlier and detailed in FIGS. 9 and 10. Conversely, in titrations in methanol/water a substantial rise in the pKa value for a substance designed to form an internal acid-specific H-bond, relative to the pKa for a very similar substance which cannot form such an H-bond, is principally attributable just to the internal H-bond, and not to any lipophilicity increase in the acid moiety which might be a consequence of that internal H-bond.

To reiterate, the essential property of an advanced pH-switch component is that it have a structure which is effective to form an internal acid-specific H-bond in aqueous solution, where that H-bond serves to raise the effective pKa of the carboxyl moiety and give a greater hydrophilicity/lipophilicity differential in switching between the anionic form and the non-ionic form, compared to a similar substance which cannot form such an internal acid-specific H-bond in aqueous solution.

3. Oligomeric Structures with Improved Specificity

A. Key Factors Affecting Efficacy and Specificity

The interstitial space in normal tissues is generally at or very near pH 7.4, and in acidic areas of tumors a pH of around 6.4 is fairly typical or readily achieved by known methods. If one knows the pKa value of an acid substance (pKa is the pH at which the acid moiety is half ionized in aqueous solution) one can use the Henderson-Hasselbalch equation (pH=pKa+log [A-]/[HA]) to calculate what fraction of that substance will be in the acid form at any selected pH. Table 1 shows the calculated percent of acid substances which will be in the acid form at pH 6.4 (present or achievable in acidic areas of tumors) and at pH 7.4 (in normal tissues), as well as the ratio of the percent in acid form at pH 6.4 divided by the percent in acid form at pH 7.4. These values are given for a representative aliphatic carboxylic acid (propionic acid, pKa 4.87), and for an acid with a moderately high pKa (chlorambucil, pKa 5.80), as well as for two hypothetical advanced pH-switches with pKa values of 6.1 and 6.4.

TABLE 1

| Acid | pKa | Percent in Acid Format | | Ratio of Percent in Acid Form at pH 6.4/ at pH 7.4 |
|---|---|---|---|---|
| | | at pH 6.4 | at pH 7.4 | |
| Propionic Acid | 4.87 | 2.9% | 0.3% | 9.7 |
| Chlorambucil | 5.80 | 20.1% | 2.4% | 8.2 |
| Advanced pH-switch 1 | 6.10 | 33.4% | 4.8% | 7.0 |
| Advanced pH-switch 2 | 6.40 | 50.0% | 9.1% | 5.5 |
| | | (relates to efficacy) | | (relates to therapeutic index) |

From Table 1 it can be seen that for such substances a higher pKa value correlates with a higher fraction of that substance existing in the acid form in acidic areas of a tumor (pH 6.4). For the case of an onco-tool, this greater percent in the acid form is expected to correlate with greater retention in acidic areas of a tumor, which translates to a stronger diagnostic signal or greater therapeutic efficacy.

However, it is also clear from that table that a higher pKa gives a corresponding increase in the amount of substance existing in the acid form at pH 7.4, which will cause increased retention in normal tissues. In the diagnostic application this would be expected to generate a greater background signal from normal tissues surrounding a tumor, perhaps so much so that it could swamp out the signal from the tumor. In the therapeutic application the increased retention in normal tissues would be expected to reduce the therapeutic index (i.e., activity against tumor/activity again normal tissues) to such a low level that the therapy causes great harm to or death of the patient.

The problem one faces then is that if the pKa of the carboxylic acid moiety of the pH-switch of an onco-tool is fairly low, such as with a conventional carboxylic acid, then the diagnostic signal or therapeutic efficacy for that onco-tool is expected to be unduly low. Conversely, if the pKa is substantially higher, as can be achieved with advanced pH-switches, then the background to the diagnostic signal could easily become so high as to swamp out the signal from the tumor, or the therapeutic index could become impractically low, resulting in great harm to the patient.

This efficacy/specificity challenge is particularly forbidding with respect to attempts to exploit the acidity in tumors because one only has about a 1.0 pH unit differential between normal tissues and most acidic areas of tumors. In this regard, a simple application of the Henderson-Hasselbalch equation appears to suggest that there is an upper limit of only about 10 for the maximum therapeutic index one can possibly achieve with cancer therapeutics designed to exploit the pH differential between normal tissues and acidic areas of tumors. This appearance of a rather low limit on the maximum achievable therapeutic index may help explain the dearth of attempts by cancer researchers to exploit the characteristic acidity of tumors for diagnosis and therapy.

B. Physical and Mathematical Basis for Improved Specificity

Contrary to the apparent low limit on the maximum achievable therapeutic index for tumor therapeutics designed to exploit the acidity of tumors, the present inventor recently devised a structural design strategy for substantially increasing the specificity of onco-tools for acidic areas of tumors. In essence, the strategy is to design onco-tools which contain two or more pH-switches, where the carboxyl of each pH-switch is sufficiently distant (greater than about 5 angstroms) from the carboxyl of its neighboring pH-switch that ionization of one does not significantly suppress the ionization of its neighbor. Conversely, the neighboring pH-switches of such oligomeric onco-tools must be in sufficiently close proximity that all (or for higher oligomers, at least most) of the component pH-switches must be in the non-ionic form in order for that onco-tool to be sequestered in acidic areas of tumors. This is illustrated in FIG. 19a for an onco-tool containing a cargo component and two pH-switch components, and in FIG. 19b for an onco-tool containing a cargo component and three pH-switch components.

The key to this design strategy is that the all-acid fraction of the oligomeric pH-switch undergoes a much sharper pH-mediated transition than the acid portion of a monomeric pH-switch, and this can afford a dramatic increase in the effective therapeutic index for an onco-tool containing such an oligomeric pH-switch.

To illustrate the basis for this specificity improvement with oligomeric pH-switches, Table 2 shows calculated values as in Table 1, but now includes onco-tools containing one, two, and three advanced pH-switches, and the calculated values are for that fraction of an onco-tool wherein all of its pH-switches are in the acid form at the selected pH. In these calculations the Henderson-Hasselbalch equation was used to calculate the relative concentration of salt and acid forms at a given pH for a substance having acid moieties with the specified pKa values. Then a binomial expansion was used to calculate the relative concentration of the all-acid form for an onco-tool containing 2 or 3 pH-switch components, as illustrated in FIG. 19.

TABLE 2

| Acid | pKa | Percent in All-Acid Form at pH 6.4 | Percent in All-Acid Form at pH 7.4 | Ratio of Percent in All-Acid Form at pH 6.4/ at pH 7.4 |
|---|---|---|---|---|
| Propionic Acid | 4.87 | 2.9% | 0.3% | 9.7 |
| Chlorambucil | 5.80 | 20.1% | 2.4% | 8.2 |
| Onco Tool 1 | 6.10 | | | |
| One pH-switch | | 33.4% | 4.8% | 7.0 |
| Two pH-switches | | 11.2% | 0.2% | 49.0 |
| Three pH-switches | | 3.7% | 0.01% | 342.3 |
| Onco Tool 2 | 6.40 | | | |
| One pH-switch | | 50.0% | 9.1% | 5.5 |
| Two pH-switches | | 25.0% | 0.8% | 30.3 |
| Three pH-switches | | 12.5% | 0.08% | 166.4 |
| | | (relates to efficacy) | | (relates to therapeutic index) |

These calculated values suggest that onco-tools containing two or more advanced pH-switch components can provide greatly improved specificities for tumors, relative to onco-tools containing just a single pH-switch component. The results also suggest that at pH 6.4 enough of the oligomeric onco-tools should be in their all-acid form to achieve reasonably efficient sequestering in acidic areas of tumors.

In this context, it should be noted that the peptide pH-switches, such as shown in FIGS. 4 and 5, can be envisioned as a linear chain of multiple individual pH-switches, where each such pH-switch component comprises one glutamic acid plus its neighboring lipophilic amino acids. To a large extent it appears to be the ratio of the glutamic acids to the lipophilic amino acids in such peptides which determines their respective pKa values. It is noteworthy that these pKa values are substantially higher than one would expect for peptides containing multiple glutamic acids. Most probably this substantial increase in these pKa values over the expected is a consequence of the hydrophilicity/lipophilicity effect detailed in FIGS. 9 and 10 and Example 1. In this regard, when the peptides in FIG. 5 are in their alpha-helical configuration, the ratio of non-polar hydrogens to H-bonding sites exposed to the solvent ranges from a low of 3.3 for core repeating sequences vii and viii, to a high of 5.0 for core repeating sequence i. It is noteworthy that these ratio values are in about the same range as the ratios which have been found to be desirable for advanced pH-switches, such as illustrated in FIG. 18.

C. Structural Designs for Improved Specificity

FIG. 20a shows a representative composition containing two advanced pH-switch components. After synthesis, this composition was partitioned between n-octanol and aqueous buffer, and the results are plotted in FIG. 20b. These results indicate that at pH 6.4 about half of this composition partitioned into the octanol phase, while at pH 7.0 only about 2% partitioned into the octanol, and at pH 7.2 none of the composition was detected in the octanol phase.

As suggested by the data in Table 2 regarding onco-tools with multiple pH-switches, these partitioning results demonstrate that the majority of a composition containing two advanced pH-switch components can exist in its all-acid form (i.e., octanol-soluble form) at a pH which is present or attainable in acidic areas of tumors, and then that composition can switch virtually completely to its salt form (i.e., buffer-soluble) at the pH present in normal tissues. This provides experimental evidence for the value of incorporating multiple pH-switch components into an onco-tool as a means for greatly increasing the onco-tool's specificity for acidic areas of tumors.

FIG. 21 further illustrates a variety of ways two or more advanced pH-switch components plus a suitable cargo component can be joined to form a high-specificity onco-tool.

4. Cargo Components

A. Design considerations for Cargo Component

The cargo component of an onco-tool must carry out its function (report its presence to a detector outside the body, or kill cells in the tumor) without unduly interfering with the function of the pH-switch component(s). When the onco-tool is fairly large by virtue of containing a peptide pH-switch (typically about 2,000 to 4,000 daltons) the cargo component can be moderately large and/or polar and still not unduly interfere with the function of the pH-switch component(s). Conversely, when the onco-tool is relatively small by virtue of containing one or a few advanced pH-switches (typically less than 1,000 daltons) then it is desirable that the cargo component be fairly small and that it be neither strongly hydrophilic nor strongly lipophilic. This is so that the pH-independent properties of the cargo component do not dominate over the pH-dependent properties of the pH-switch component(s).

B. Two Forms of Cargo Component

In principle, the cargo component can carry out its cell killing function utilizing a toxin or other substance, as described in the inventor's pending patent applications. However, the inventor now believes that both the reporting and the cell killing functions are best carried out by utilizing appropriate radioisotopes, and preferably radioisotopes having half-lives of only a few hours to a few days. Therefore, for practical reasons it is envisioned that onco-tools will generally be manufactured, stored, shipped to the user, and stored by the used until needed while the cargo component of the onco-tool is in a form which is effective to bind a radioisotope—but which does not yet contain that radioisotope. This "effective to bind a radioisotope" form of the cargo component should have a structure such that when it is contacted with the selected radioisotope that radioisotope is easily and efficiently bound to the cargo component with a minimum of manipulation. It should be noted that methods for binding radioisotopes to such suitable structures are well known and routinely used in the nuclear medicine field. It is also essential that the radioisotope thereafter remain stably bound to the cargo component throughout the course of the diagnostic or therapeutic process. FIGS. 22a and 23a illustrate representative cargo components in their "effective to bind a radioisotope" form, and FIGS. 22b and 23b illustrate representative cargo components in their "contains a radioisotope" form.

Thus, it is envisioned that onco-tools will generally be synthesized, stored, shipped to the used, and stored by the used until needed while the cargo component of the onco-tool is in its "effective to bind a radioisotope" form. Then when needed, that onco-tool will be contacted with the selected radioisotope (generally prepared in a nuclear reactor or a cyclotron) to generate the final form of the onco-tool which contains that selected radioisotope. It is this final "contains a radioisotope" form which is delivered into the patient, and which will be sequestered in acidic areas of tumors if such tumors are present.

C. Onco-tool Function Determined by Radioisotope

It should be noted that in many cases a given onco-tool containing a cargo component in its "effective to bind a radioisotope" form, such as shown in FIGS. 22a and 23a, can be used either for detection of tumors, or for treating tumors. This dual potential is because it is the specific radioisotope which determines the function which the onco tool will perform. For example, if the "effective to bind a radioisotope" form is contacted with a gamma-emitting, positron-emitting, x-ray-emitting, or electron-capture type radioisotope then the resulting onco-tool will be suitable for diagnostic use; and if the "effective to bind a radioisotope" form is contacted with an alpha-emitting or beta-emitting radioisotope then the resulting onco-tool will be suitable or therapeutic use. It should also be appreciated that if the "effective to bind a radioisotope" form is contacted with a radioisotope which both generates a signal detectable outside the body and emits an alpha or beta particle, such as iodine-131, then the resulting onco-tool can be used for both diagnostic and therapeutic use.

D. Conventional Cargo Components for Large Onco-tools

For onco-tools containing a relatively large peptide pH-switch component (typically about 2,000 to 4,000 daltons) one can use a relatively polar cargo component suitable for rapidly and efficiently chelating a metal oxide-type radioisotope, such as technetium-99 or rhenium-186. A representative cargo component of this type known as MAG3, which is well known in the nuclear medicine field, is shown in FIG. 22. FIG. 22a shows that cargo component in its form which is effective to bind a metal oxide-type radioisotope. FIG. 22b shows that cargo component with a bound radioisotope. Generally just before introduction of the onco-tool into the patient the radioisotope will be added to the onco-tool form shown in FIG. 22a, by established methods known in the nuclear medicine field, and this will generate the onco-tool form wherein the cargo component now includes the bound radioisotope, as shown in FIG. 22b. A number of alternative structures suitable for use as cargo components for binding metallic radioisotopes are detailed in Chapter 3 of the book: Radioimmunotherapy of Cancer, by P. Abrams and A. Fritzberg (2000), Published by Marcel Dekker, Inc., New York.

E. Advanced Cargo Components for Small and Large Onco-tools

In contrast to the case for relatively large peptide-containing onco-tools, for relatively small onco-tools containing no peptide component and only one or a few advanced pH-switch components (typically less than 1,000 daltons) it is desirable to use a relatively small cargo component which is neither strongly lipophilic nor strongly hydrophilic. This is because a strongly lipophilic cargo component can cause undue binding of the small onco-tool to normal tissues (pH 7.4), while a strongly hydrophilic cargo component can disfavor tissue binding of the small-onco tool in acidic areas of tumors. As noted earlier, it is also essential that said cargo component be effective to readily and efficiently bind a selected radioisotope with minimal manipulation, and that the bound radioisotope not be readily cleaved off the cargo component during the diagnosis or treatment process.

New cargo components have recently been devised to satisfy the more demanding requirements of small onco-tools containing one or more pH-switches of the advanced pH-switch type. These new "advanced cargo components" contain an alkene or a 5-membered or 6-membered aromatic ring, such as a furan, thiophene, pyrrole, imidazole, pyridine, pyrimidine, or triazole, which: i) contains a moiety, such as a trialkyl tin, that is readily displaced by a radiohalogen; or, ii) contains a radiohalogen. The radiohalogen for such advanced cargo components is selected from fluorine, bromine, iodine, and astatine. FIG. 23a shows four representative advanced cargo components in a form effective to bind a radiohalogen, and FIG. 23b shows those cargo components in a form which contains a radiohalogen. In regard to a moiety which can be readily and efficiently displaced by a radiohalogen, a tributyl tin moiety is readily displaced by bromine and iodine, while a trimethyl tin moiety is readily displaced by bromine, iodine, and astatine (Zalutsky et al., Proc. Natl. Acad. Sci. USA. vol 86 pages 7149-7153 (1989)).

Figure 23:
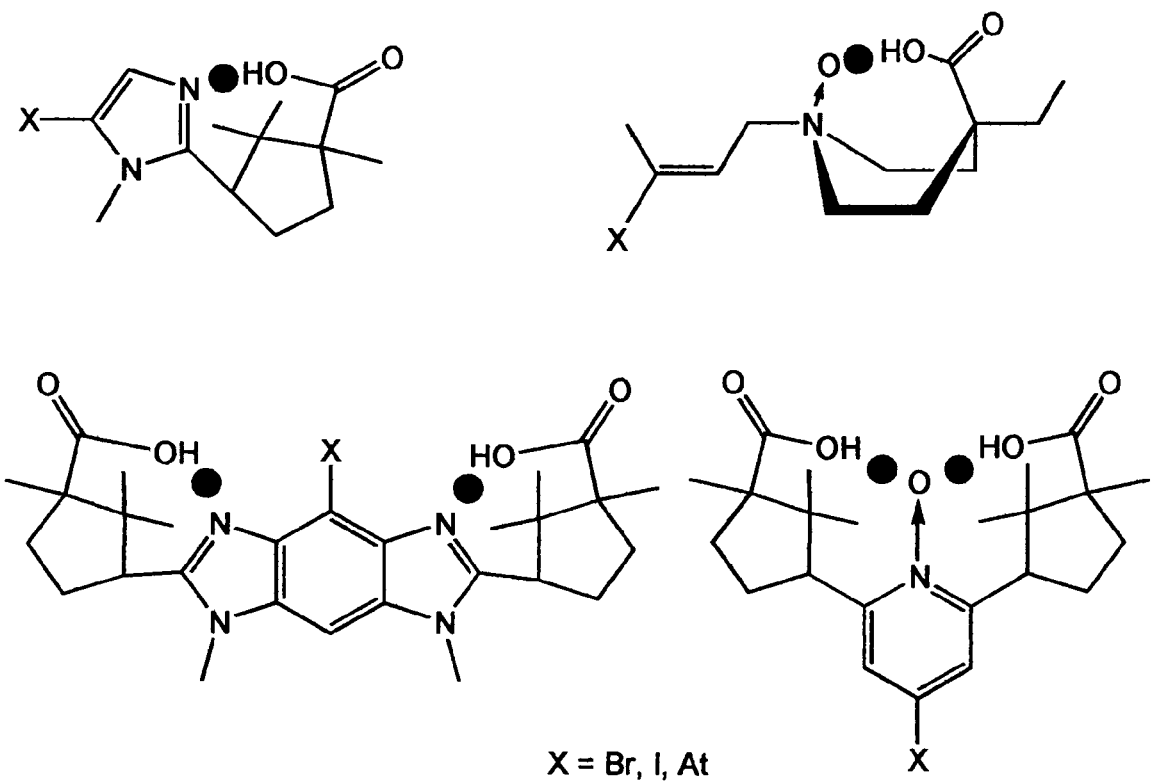
FIG. 23 shows improved cargo components for small onco-tools.

It should be noted that these advanced cargo components, such as shown in FIG. 23, are also entirely suitable for use with the relatively large onco-tools, such as those containing a peptide pH-switch component.

F. Cargo Components Indistinct from pH-switch Components

The role of the cargo component is to bind a functional group, preferably a radioisotope, which is effective to report the presence of the onco-tool and/or effective to kill cells. A cargo component effective to carry out this role can be quite small and does not need to be clearly distinct from the pH-switch component. FIG. 23c illustrates several prospective advanced cargo components which are not clearly distinct from their advanced pH-switch components.

5. Improved Cargo for Killing Quiescent Tumor Cells

A. Selection of Much More Effective Radioisotope

Because the quiescent cells in acidic areas of tumors are dividing only slowly or not at all they are quite resistant to both chemotherapeutics and radiation damage. In the inventor's previously-submitted/now-pending patent applications (Ser. No. 11/069,387 and Ser. No. 11/069,849) conventional beta-emitting radioisotopes commonly used in therapy with radioisotopes were selected for killing these quiescent tumor cells. However, the inventor has recently come to the realization that such radioisotopes are less than ideal for this particular application. With further investigation the inventor has now concluded that in order to provide a high expectation of completely killing such treatment-resistant quiescent tumor cells, a radioisotope should be used whose emission releases a vast amount of energy (millions of electron volts) over a very short distance (a few cell diameters), such that the released energy will be highly effective to kill all of the radiation-resistant quiescent tumor cells near or in which radioisotope-carrying therapeutic onco-tool is positioned. The inventor has recently concluded that alpha-emitting radioisotopes best satisfy this particular very demanding requirement.

The inventor has further concluded that the best radioisotopic element for onco-tools explicitly designed to kill quiescent tumor cells is astatine, with astatine-211 being particularly preferred. This radioisotope, which has been used in radioimmunotherapy applications by Michael Zalutsky, can be generated from natural bismuth 209 in a medium-energy cyclotron equipped with an alpha particle beam. Astatine-211 has a half-life of 7.2 hours and emits two alpha particles with energies of 5.87 and 7.45 million electron volts, which devastate cells within the approximately 50 to 80 micron paths of the emitted alpha particles (a few cell diameters). Just 1 or 2 such alpha emissions can kill even the most radiation-resistant tumor cell. Actinium-225 is an alternate alpha-emitter which might also be acceptable for this particular application.

B. Cargo Components with Improved Binding of Preferred Radioisotopes

Astatine is a halogen with chemical properties similar to iodine. As a consequence, a convenient "effective to bind a radioisotope" form for the cargo component is one with a trimethyl tin moiety, such as any of the representative advanced cargo component structures shown in FIG. 23a. That trimethyl tin moiety is then readily displaced by astatine by known methods (Zalutsky et al., Proc. Natl. Acad. Sci. USA. vol 86 pages 7149-7153 (1989)) to give the "contains a radioisotope" form of the cargo component of the onco-tool. That final form of the onco-tool is next processed and then delivered into the patient.

6. Onco-Tools-Only Method for Killing Entire Tumor

A. The Therapeutic Challenge

Therapeutic onco-tools were initially devised solely as a means for killing treatment-resistant cells in acidic areas of tumors and initially it was envisioned that the cell killing moiety would be a toxin or a beta-emitting radioisotope (see pending patent applications by applicant: Ser. No. 11/069,849, pending; and Ser. No. 11/069,387, allowed but not yet published or issued). Because onco-tools are designed to be sequestered only in acidic areas of tumors, it was initially expected that such onco-tools would have to be used in conjunction with more conventional cancer therapies, such as radiation therapy or chemotherapy, in order to also kill the treatment-sensitive fast-dividing tumor cells in areas of tumors lacking adequate onco-tool because of higher pH. However, the inventor judged this "onco-tool plus conventional cancer therapy" approach was less than ideal because the conventional cancer therapies are inherently quite toxic to patients.

B. Method for Killing Entire Tumor with Onco-tools

With the objective of avoiding the high toxicity associated with conventional cancer therapies, the inventor recently devised an improved therapeutic strategy wherein onco-tools alone can be used to destroy the entire tumor, thereby obviating the need for co-treatment with more toxic conventional cancer therapies. This "onco-tools-only" therapeutic strategy entails using at least two onco-tools effective to kill cells. One of the onco-tools contains an alpha-emitting radioisotope which serves to kill treatment-resistant quiescent cells containing or in very close proximity to onco-tool sequestered in acidic areas of the tumor. Another onco-tool contains a beta-emitting radioisotope, which serves to kill from a distance the more treatment-sensitive fast-dividing tumor cells in less-acidic areas of the tumor. These more vulnerable fast-dividing cells in areas of the tumor having a more normal pH may be as much as about 50 to several hundred micrometers from onco-tool sequestered in acidic areas of the tumor.

The preferred alpha-emitting radioisotopes for this combination onco-tools-only therapy are the astatine radioisotopes 209, 210, and 211, with astatine-211 being most preferred. Actinium-225 may also be suitable for this particular application.

While there are a number of beta-emitting radioisotopes which can be used in such a combination onco-tools-only therapy, bromine-76, bromine-82, iodine-130, iodine-131, iodine-133, and iodine-135 are particularly preferred. Other beta-emitting radioisotopes with favorable properties include rhenium-186 and yttrium-90. It may be desirable to use two or more different beta-emitting radioisotopes. Specifically, it may be desirable to use two with significantly different mean path lengths in order to assure good cell killing both proximal and distal to the onco-tool sequestered in the acidic areas of the tumor. It may also be desirable to use two beta-emitting radioisotopes with substantially different half lives, in order to effect relatively intense cell killing effects early in the treatment plus continued cell killing over a longer time period.

Compared to treatment where onco tools are used only to kill the quiescent cells in acidic areas of tumors, combined with conventional cancer therapies for killing the fast-dividing tumor cells in other areas of tumors having a less acidic pH, this new combination onco-tools-only therapeutic strategy for killing the entire tumor should afford a simpler, less costly, far less toxic, and far more effective treatment.

One has considerable latitude in selecting the beta-emitting radioisotope or combination of beta-emitting radioisotopes which are to serve for killing the fast-dividing tumor cells. A few of the promising radioisotopes for this purpose include:

| Radioisotope | Half-life | Approximate Mean Path Length |
|---|---|---|
| bromine-76 | 16 hours | |
| bromine-82 | 35 hours | |
| iodine-130 | 12 hours | |
| iodine-131 | 8 days | 910 microns |
| iodine-133 | 21 hours | |
| iodine-135 | 6.6 hours | |
| rhenium-186 | 3.8 days | 1,800 microns |
| yttrium-90 | 2.7 days | 3,900 microns |

It should be noted that because of the complex effects cell killing may have on tumor acidity, it may be desirable to deliver the onco-tool containing the alpha-emitting radioisotope either well before or well after the time the onco-tool containing the beta-emitting radioisotope, or the set of onco-tools containing the set of beta-emitting radioisotopes, is delivered.

7. Design, Optimization, and Preparation of pH-Switches and Onco-Tools

A. Preparation and Optimization of Onco-Tools Containing a Peptide pH-Switch Peptide pH-switches of the present invention, such as the peptides containing the core repeating sequences shown in FIG. 5a, can be synthesized on 1% cross-linked polystyrene resin of the Wang type or the hydroxymethyl type using an automated peptide synthesizer supplied with fluorenyl-methoxycarbonyl-protected/pentafluourophenyl ester-activated amino acids. Typically, all the amino acids are of the unnatural D chirality, in order to give peptides resistant to peptidases and proteases present in biological systems, and in order to minimize peptide reuptake by proximal tubules in the kidneys. The C-terminal amino acid of the peptide is typically linked to the synthesis resin via an ester link cleavable with a primary amine. In many cases the C-terminal amino acid is a glycine, alanine or leucine, which is then followed by a core sequence comprising multiple repeats of a selected short sequence suitable for the pH-switch. Preferred sequences suitable for peptide pH-switches are shown in FIG. 5a. Reagents and methods for preparing such peptides are well known in the peptide synthesis art and are available from and detailed in the NovaBiochem Handbook and Catalog, 2000.

After the core peptide sequence has been prepared on a peptide synthesizer, a number of additional steps are needed to process that peptide pH-switch and convert it to an effective onco-tool. FIG. 24 shows the steps in preparing a representative onco tool containing a peptide pH-switch component of the invention. The peptide contains the amino acid sequence shown in FIG. 4 and in FIG. 5a(iv) where n=4. Structure D in FIG. 24 is the form of the onco tool which is effective to bind a radiohalogen. It is this form which is suitable for storage and shipment to the end user, who will generally also store it until needed. When desired the end user will then contact the structure D onco tool with a suitable radioisotope, such as an Iodine-131 (or other radiohalogen of choice), to generate the final form shown in Structure E containing a radioisotope. It is this final form which is delivered into the subject for detection or treatment of tumors. Procedures for displacing the trimethyl tin moiety with Iodine (or other radiohalogen) are detailed in Zalutsky et al, referenced in the earlier section describing the design of the cargo component.

In regard to optimization, the principal properties which can be easily be varied in onco-tools containing peptide pH-switches are: a) the amino acid sequence of the core peptide; b) length of the core peptide; c) one or both of the end structures which is(are) to be largely anionic at pH 7.4 and largely non-ionic and lipophilic at pH 6.0; and, d) the cargo component in its "contains-a-radioisotope" form. In regard to amino acid sequence, while a variety of sequences can be effective as peptide pH-switches, the repeating sequences shown in FIG. 5 are particularly preferred. In regard to the length of the peptide, it should be appreciated that when peptides of the type suitable as pH-switches are less than about 13 or 14 amino acids in length the helical conformation of their alpha helical backbone is rather unstable, presumably due to end effects, and this helical instability can substantially reduce the achievable lipophilicity of the peptide in its acid form. As the number of amino acids in the pH-switch peptide is increased the inventor has found that there is generally a progressive (roughly asymptotic) increase in the achievable lipophilicity of the peptide in its acid form, and such an increase generally gives a desirable increase in the pH at which the peptide switches between its salt and acid forms. However, there is a tradeoff for increased length because the cost of synthesis goes up appreciably as the length increases. In regard to the end structure on one or both of the termini, the inventor has recently come to fully appreciate that such end structures must undergo a pH-dependent shift, where the terminus is largely anionic and hydrophilic at pH 7.4, and largely non-ionic and lipophilic in acidic areas of tumors. Representative end structures which provide a reasonably acceptable pH-dependent shift are illustrated in FIG. 8. Finally in regard to suitable cargo components for onco-tools containing a peptide pH-switch, one has substantial latitude as long as the cargo component in its "contains-a-radioisotope" form does not cause significant tissue binding at pH 7.4. FIGS. 22*b* and 23*b* show a variety of representative cargo components which are generally acceptable.

B. Preparation of Combination Peptide pH-switch/Advanced pH-switch Onco Tools

Figure 25:
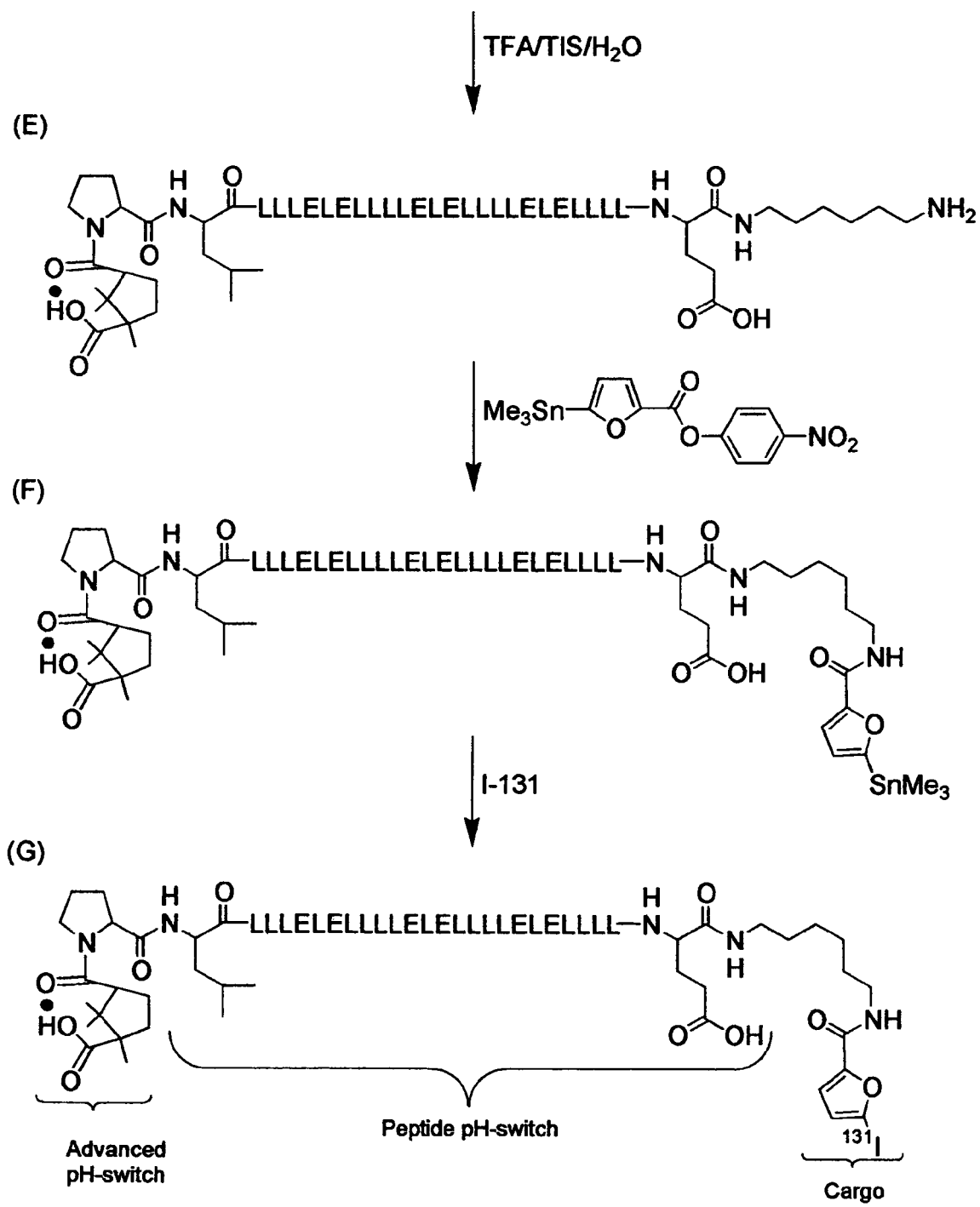
FIG. 25 shows the steps in preparation of an onco-tool containing an improved peptide pH-switch component, plus an advanced pH-switch component.

The specificity and efficacy of an onco-tool containing a peptide pH-switch can typically be improved simply by adding an advanced pH-switch to one or both termini. FIG. 25 shows the steps in a synthetic route for preparation of a representative onco-tool comprising a peptide pH-switch (sequence from FIG. 5*a*(iv)) containing an advanced pH-switch (a camphoric acid/amide moiety such as shown in FIGS. 12*a* and 15*b*) on the N-terminus and a cargo component (from FIG. 23) on the C-terminus. Structure F in this synthetic scheme shows the "effective-to-bind-a-radioisotope" form and Structure G shows the "contains-a-radioisotope" form.

C. Design and Optimization of Advanced pH-switches

A useful approach to designing an advanced pH-switch is to start with a molecular model of a 4-membered, 5-membered, or 6-membered aliphatic ring, such as illustrated in FIG. 13*a*. The ring, particularly if it is a six-membered ring, may also have one or more additional groups which serve to further limit the conformational freedom of the ring or H-bonding elements attached to the ring, or to favor the ring conformation which positions the H-bonding elements optimally for formation of the desired internal H-bond. For example, a 6-membered ring with a carboxyl at the 1 position and an H-bond acceptor moiety at or linked to the 4 position, may have an additional 2-carbon bridge between the 2 and 5 carbons of the ring in order to lock the ring into the twisted-boat conformation—which is the optimal conformation for forming the desired internal H-bond between the H-bond donor and acceptor moieties. One next adds to the selected ring a carboxylic acid moiety which will serve as the H-bond donor, and then adds a suitably-positioned H-bond acceptor moiety, generally a nitrogen or oxygen, which must have a structure such that in its non-ionic form it cannot also serve as an H-bond donor. These design steps give core structures, such as shown in FIG. 17, suitable for subsequent development into advanced pH-switches. While computer-based modeling is suitable for this initial design process, the inventor has found that plastic CPK molecular models are fast, easy, and provide a particularly good appreciation of the stereochemistry of such structures in all three dimensions.

While there are a number of possibilities for the H-bond acceptor moiety, the carbonyl oxygen of an amide, such as illustrated in FIG. 12*a*, has been found to be effective and readily accessible synthetically. Alternatively, H-bond acceptor moieties which are suitable for forming a low-barrier H-bond with the carboxylic acid donor, such as illustrated in FIG. 16*a*, are particularly desirable. FIG. 17 illustrates a variety of representative core structures suitable as starting points for advanced pH-switches.

Once a core structure has been selected, one generally needs to further optimize the structure so that its anionic salt form is sufficiently hydrophilic that is has little or no affinity for tissues, while its non-ionic acid form is sufficiently lipophilic that it is effectively sequestered in tissues. A method for such structural optimization has been described earlier herein and is illustrated in FIG. 18, and entails adding various alkyl groups to suitable sites on the core structure, and then carrying out initial testing in a simple titration assay in aqueous 0.15 M NaCl, followed by more advanced testing, such as partitioning and membrane binding, on the more promising structures.

After promising structures have been identified, one must also incorporate into such structures a means for linking them into an onco tool; either via linkage to a pH-switch peptide component or another advanced pH-switch component, or via linkage to a cargo component. Ultimately, the most promising of these onco tools should be tested in tumor-bearing animals.

D. Preparation of Cargo Components a) Conventional Cargo Component for Large Onco-Tools FIG. 26 shows a synthetic route for a representative conventional cargo component suitable for large onco-tools, such as those which contain a peptide pH-switch. The final active ester form from this synthesis scheme is readily linked to the N-terminus of a peptide pH-switch to give an onco-tool which is in its effective-to-bind-a-radioisotope form, such as illustrated in FIG. 22*a*. Addition of a suitable radioisotope then gives the final contains-a-radioisotope form of the onco-tool, such as illustrated in FIG. 22*b*, suitable for use in a living subject.

b) Advanced Cargo Components for Small or Large Onco-tools

FIG. 27 shows synthetic schemes for several representative advanced cargo components suitable for small onco-tools containing one or a few advanced pH-switches, as well as being suitable for use in large onco-tools containing a peptide pH-switch. The products from these syntheses can be incorporated into onco-tools to give their effective-to-bind a radioisotope form, such as illustrated in FIG. 23*a*. Addition of a suitable radiohalogen then gives the final contains-a-radioisotope form, such as illustrated in FIG. 23*b*, suitable for use in a living subject.

E. Preparation of Onco-tools Containing One Advanced pH-switch

FIG. 28 shows several synthetic routes for preparing representative onco tools, each containing a single advanced pH-switch component. In each case, the next to the last structure in each synthetic scheme is the effective-to-bind-a-radioisotope form of the onco-tool, and the last structure in each synthetic scheme is the contains-a-radioisotope form of the onco-tool suitable for use in a living subject.

F. Preparation of High-specificity Onco-tools Containing Multiple Advanced pH-switches a) An Onco-tool Containing Two Advanced pH-switches FIG. 29 illustrates a synthetic route for preparing a representative onco tool containing two advanced pH-switch components. The next to the last structure in this synthetic scheme is the effective-to-bind-a-radioisotope form of the onco-tool, and the last structure in this synthetic scheme is the contains-a-radioisotope form of the onco-tool suitable for use in a living subject.

b) An Onco-tool Containing Three Advanced pH-switches

FIG. 30 illustrates a synthetic route for preparing a representative onco tool containing three advanced pH-switch components. The next to the last structure in this synthetic scheme is the effective-to-bind-a-radioisotope form of the onco-tool, and the last structure in this synthetic scheme is the contains-a-radioisotope form of the onco-tool suitable for use in a living subject.

G. Addition of Radioisotope to the Effective-to-bind Form, and Purification of Final Form a) Onco-tools Containing Conventional Cargo Component Commercial kits are available in the nuclear medicine field which are routinely used to prepare metal oxide-type radioisotopes, such as technetium-99, rhenium-186, and yttrium-90, for, complexing to conventional cargo components, such as the MAG3 cargo component shown in FIG. 22. Such kits provide an optimized reagent mixture which serves to generate the chemical form of the radioactive element that is suitable for complexing with the cargo component.

Once the selected radioisotope has been complexed with the cargo component of the onco-tool using such a kit, it is generally desirable to purify the onco-tool product away from any radioisotope not bound to the onco-tool, and any other undesirable contaminants.

One method for purifying the onco-tool is to adjust the reaction mixture to about pH 5 in water and add to a small fritted column containing reverse phase chromatography medium. At pH 5 the onco-tool will generally be retained on such a column. After washing with pH 5 buffer, elute the onco-tool with a small volume of pH 7.5 buffer. The eluant containing the onco-tool is then heat sterilized or filter sterilized, after which it is suitable for injection into a living subject.

Another method for purifying the final form of the onco-tool is to partition it between aqueous pH 5 buffer and an organic phase, such as octanol. At pH 5 the onco-tool partitions into the organic phase. After removing the aqueous phase, the octanol phase is contacted with an aqueous pH 7.5 buffer, whereupon the onco-tool partitions into the aqueous phase. The aqueous phase containing the onco-tool is then heat sterilized or filter sterilized, after which it is suitable for injection into a living subject.

b) Onco-tools Containing Advanced Cargo Component

For the case of radiohalogens for use with advanced cargo components, if the radiohalogen is provided in the salt form, such as NaI-131, the iodine should be oxidized to the free iodine form. This is typically carried out with t-butylhydrogen peroxide, or other suitable oxidizing agent. The free iodine (or other radiohalogen) is then contacted with the onco-tool in its effective-to-bind-a-radioisotope form, such as shown in FIG. 23a, whereupon the halogen displaces the trialkyl tin moiety to form the contains-a-radioisotope form of the onco-tool, plus a trialkyl tin halide product.

Once the radiohalogen has been so linked to the onco-tool, the onco-tool is purified away from any radioisotope not bound to the onco-tool, and away from other undesirable contaminants by the methods described in section (a) above.

8. Testing pH-switches and Onco-Tools

A. Titration Assay

Typically new structures that may be suitable as advanced pH-switch components are first assessed for their pKa value in normal saline. This entails preparing the sodium salt form of the structure and dissolving it at a concentration of 20 milliMolar in 15 ml of 0.15 Molar NaCl (deareated to remove $CO_2$). A small magnetic stir bar is added and the pH of the solution adjusted to about 9 with a small amount of 5 M NaOH. While stirring, 5 microLiter portions of 5 M HCl are added and the pH is recorded at 1 minute after addition of each portion. A plot of pH versus volume of added HCl affords the effective pKa value. It is also desirable to carry out this same titration in methanol/water (1:1 by vol) in order to get an estimate of the pKa value independent of insolubility effects.

B. Precipitation Assay

A precipitation assay is a useful alternative to the titration assay and requires far less material. The precipitation assay is appropriate when the pH-switch or onco tool contains a moiety readily detectable in the UV absorbance range, such as is the case for structures containing aromatic cargo components. In this assay one first prepares a series of buffers having pH values ranging from 5.0 to 8.0 in 0.2 pH increments. Each buffer is 0.14 M in NaCl and 0.015 M in buffer. Preferred buffers are:

a) 2-(Morpholino)ethanesulfonic acid (MES, pKa 6.1);
b) N-(2-Acetamido)-2-aminoethanesulfonic acid (ACES, pKa 6.8); and,
c) 4-(2-Hydroxyethyl)piperazine-1-ethanesulfonic acid (HEPES, pKa 7.5).

A 1 ml portion of each buffer prep is placed in a 1.5 ml centrifuge tube and 10 microliters of sample solution is added. Typically the stock sample solution is the sodium salt form of the test compound in water at a concentration sufficient go give an absorbance value of about 100, so that when 10 microliters of this stock solution is diluted into the 1 ml of buffer the absorbance will be about 1.0-minus any quantity which has precipitated (which generally occurs in the lower-pH buffer solutions). Each vial is then capped, shaken well, allowed to sit at room temperature for 30 minutes, and then centrifuged in a microcentrifuge at 10,000 rpm for 10 minutes. Supernatants are then assessed in a UV/Vis spectrophotometer and the absorbance values plotted as a function of pH.

Onco-tools, particularly ones containing a peptide pH-switch with an advanced pH-switch on one terminus, can show a quite sharp pH-dependent switch between soluble (salt) and insoluble (acid) forms, with about 90% of the transition occurring within a range of about 0.5 pH unit for preferred structures, such as ones closely related to structure G of FIG. 25.

C. Octano/Buffer Partitioning Assay

Like the precipitation assay above, a partitioning assay is most practical when the substance to be tested contains a moiety readily detectable in the UV absorbance range. In this assay a 0.5 ml portion of each buffer preparation, as described in the previous section, is placed in a 1.5 ml centrifuge tube and 10 microliter of the stock sample solution, as described in the previous section, is added to the buffer solution. Next, 0.5 ml of n-octanol is added to each vial, the vials capped and shaken vigorously for 2 minutes, and then centrifuged to separate the phases.

A 0.3 ml portion of each octanol top phase is added to 0.5 ml of isopropanol and the absorbance measured. These absorbance values for all samples are plotted as a function of the pH of the buffer phase. Likewise, a 0.3 ml portion of each lower buffer phase is added to 0.5 ml of water and the absorbance measured, and the absorbance values for all samples plotted as a function of the pH of the buffer phase.

D. Binding to Isolated Cell Membranes

Red cell ghosts are prepared from fresh blood by osmotic lysis and repeated centrifugal washes in normal saline. About 0.5 ml of packed red cell ghosts are resuspended in 1.5 ml of 0.15 M NaCl/0.01 M sodium azide to give a stock solution of isolated cell membranes. Each time before using this stock membrane suspension swirl it briefly for a few seconds. This stock membrane suspension can be used and stored at 4 deg. C. for several days.

As with the precipitation and partitioning assays, membrane binding assays are most suitable when the substance to be assayed has a substantial absorbance in the visable or UV range.

A typical membrane binding assay is carried out much like the precipitation assay. Specifically, a 1.0 ml portion of each buffer preparation, prepared as for the precipitation assay above, is placed in a 1.5 ml centrifuge tube and 10 microliters of sample solution is added. Typically the stock sample solution is the sodium salt form of the test compound in water at a concentration sufficient to give an absorbance value of about 100, so that when 10 microliters of this stock solution is diluted into the 1 ml of buffer the absorbance will be about 1.0. Next, 75 microliters of the stock membrane suspension described above, is added, the tube is capped and swirled briefly, and then all the tubes incubated at 37 deg. C. for 30 minutes. It should be noted that these incubations are carried out at 37 deg. C. because the inventor has found that membrane binding is somewhat temperature dependent, giving significantly different results between room temp. (typically 22 deg. C.) and 37 deg. C. The vials are centrifuged in a microcentrifuge at 10,000 rpm for 10 minutes to pellet the red cell ghosts, and the supernatants then assessed in a UV/Vis spectrophotometer. Finally, the absorbance values are plotted as a function of pH.

While in principle it is difficult to distinguish between simple precipitation and membrane binding in the above assay, in practice some pH-switches show a substantial pH-dependent affinity for membranes, while other pH-switches exhibit appreciably less pH-dependent affinity for membranes.

E. Assessment of Onco-tool Distribution in Tumor-bearing Animals a) Preliminary Assessment in Mice The decisive test for an onco-tool is to react it with a suitable radioisotope which generates a readily quantifiable signal, such as I-131, and then inject that onco-tool into tumor-bearing mice. Tumor-bearing mice are readily obtained by methods well known in the cancer research art. After allowing adequate time for excretion of un-sequestered onco-tool (on the order of about 4 to 24 hours), one can then scan the mouse with a gamma camera (or other suitable detection equipment—depending on the emission type of the selected radioisotope) to identify where and roughly how much onco-tool is retained in the tumor and in the various major organs. Alternatively, more precise results can be obtained by excising and counting the emitted radiation from each major organ and any obvious tumors. A promising onco-tool is one which gives significant label in the tumor, but little or none in normal tissues and organs, excepting perhaps the kidneys (as will be discussed below). Procedures for such testing in live animals are well known in the nuclear medicine field, and particularly in the sub-field of radioimmunotherapy.

b) Advanced Assessment in Mice

Because metastasis of the parent tumor can lead to small progeny tumors throughout the animal and sequestering of the radioactive onco-tool in such metastases could be misinterpreted as lack of specificity for tumors, it is also prudent to test promising onco-tools in tumor-free mice—where a desirable onco-tool should exhibit little or no retention in the tissues and organs of the mice, excepting perhaps the kidneys (as will be discussed below).

As will be discussed in greater detail in the following section, the urine of an animal can be acidic and this has the potential to cause re-uptake of the onco-tool by cells lining the proximal tubules of the kidneys. Luckily, safe and effective drugs, such as Acetazolamide, are available which raise the pH of the urine to levels which should prevent such acid-mediated re-uptake by the kidneys. Therefore, if sequestering of onco-tool in the kidneys is seen to be a problem, then pre-treating the test animal with Acetazolamide, or other substance effective to raise the pH of the urine, should prevent such a problem.

Also as will be discussed in greater detail in the following section, if a given onco-tool is sequestered in tumors of the mouse to a lesser extent than desired, it may be possible to significantly increase the amount of that onco-tool which is sequestered in the tumor by pre-treating the mouse with a substance which is effective to selectively reduce the pH in tumors without concomitant reduction of the pH in normal tissues. Substances effective for this purpose are discussed in the following section.

9. Methods for Detecting and Treating Tumors

A. Challenges a) Acidic Urine

One of the functions of the kidneys is to maintain the pH in the body at very close to 7.4. To carry out this function the kidneys can excrete urine ranging from moderately basic to fairly acidic. In this process a substance is filtered from the blood in the glomerulus of the kidney, after which that substance (dissolved in urine) passes through the proximal tubule where critical components excreted in the glomerulus are reabsorbed by cells lining the proximal tubule. If the urine is acidic, then an onco-tool in this acidic environment has the potential of binding and entering the cells lining the proximal tubules, much as the onco-tools enter tumor cells from an acidic extracellular environment. Stated differently, if the excreted urine is sufficiently acidic the onco-tool will switch to its non-ionic lipophilic form. If that switch to a lipophilic form occurs in a region where the urine is in direct contact with cell membranes, such as is the case of cells lining the proximal tubules of the kidneys, then the onco-tool can bind and enter such cells. In the case of a diagnostic onco-tool this can lead to excessive signal emanating from the kidneys, which could obscure a tumor near or in the kidneys. In the case of a therapeutic onco-tool this could lead to killing of the cells lining the proximal tubules, and ultimately destruction of the kidneys.

Luckily, there are methods well known in the medical arts for raising the pH of a subject's urine for sufficient time to carry out onco-tool treatment (a few hours for diagnostic onco-tools, many hours to a few days for therapeutic onco-tools). When such treatments assure that the urine is maintained at a slightly basic pH, the onco-tool will remain in its anionic hydrophilic form and be safely passed from the body by urination. One safe and effective substance for rendering the urine basic is the carbonic anhydrase inhibitor drug, Acetazolamide. Thus, a prudent course is to first treat the subject with this drug, or other substance effective to raise and maintain the pH of the urine at a pH above about 7.4, for a suitable period of time before injecting the onco-tool. Because of the potential harm to the kidneys by therapeutic onco-tools if the kidneys are excreting acidic urine, it may also be desirable to continually monitor the pH of the urine entering the bladder (such as by using a micro pH-probe at the end of a catheter) for the period of time from just before injection of the onco-tool, until such time as most of the onco-tool has been excreted by the kidneys. Such monitoring will allow emergency intervention (such as injecting more Acetazolamide) in the event the pH of the newly excreted urine begins to drop below about pH 7.4.

b) Inadequate Sequestering in Tumors

While proper design of onco-tools can give quite high pKa values and exceptionally sharp pH-mediated transitions between their ionic and non-ionic forms, nevertheless, it remains that the specificity of an onco-tool for acidic areas of tumors is a strong function of the pH differential between the acidic areas of tumors and normal tissues. Thus, if one selectively reduces the pH in acidic areas of tumors even further than is found in the natural condition, this should afford greater sensitivity for diagnostic onco-tools and greater safety and efficacy for therapeutic onco-tools.

Over the past half century a number of treatments have been reported to after the pH in tumors—some causing the pH to increase and some causing the pH to decrease. In the context of diagnostic and therapeutic onco-tools, it is the treatments that selectively decrease the pH in tumors, without a concomitant reduction in the pH in normal tissues, which are of interest. Following are three such treatments that have been reported to selectively reduce the pH in tumors.

It has long been known that introduction of glucose into tumor-bearing animals acts to reduce the pH in the interstitial space in hypoxic areas of the tumors, typically for a period of about 2 hours, while having little or no effect on the pH of the interstitial space in normal tissues (Naeslund & Swenson (1953) Acta Obstet. Gyneocol. Scand. 32, 359-367). Additional intake of glucose by mouth can significantly extend the length of time during which the pH in tumors remains so reduced.

The pH in acidic areas of tumors can also be further reduced by treating with such agents as the mitochondrial inhibitor, meta-iodobenzylguanidine, again without undue effect on the pH in normal tissues (Jahde et. al., (1992) Cancer Research 52, 6209-6215).

It has also been reported that the pH in acidic areas of tumors can be further reduced by as much as 0.7 pH unit by use of a combination of glucose and meta-iodobenzylguanidine (Kuin et al., (1994) Cancer Research 54, 3785-3792).

In addition, the pH in acidic areas of tumors can be further reduced by vasodilator drugs which are routinely used to treat persons with hypertension (Adachi and Tannock (1999) Oncology Research 11, 179-185). Such drugs are probably effective because the abnormal vasculature of tumors generally lacks vasoconstrictor nerve fibers. Therefore, when a subject is given a vasodilator drug, resistance to blood flow is unchanged in tumors but decreases in normal tissues. These differential effects of the vasodilator result in a significantly greater blood flow through normal tissues and a concomitant reduction in blood flow through the tumor. In turn, this reduced blood flow through the tumor reduces the washout of the lactic acid produced by tumor cells in hypoxic areas of the tumor—resulting in a further drop in the pH in acidic areas of the tumor.

Such treatments, or a combination of such treatments, to further reduce the pH in acidic areas of tumors should lead to sequestering of more onco-tool in the now more acidic areas of the tumor, as well as lead to an increase in the fraction of the area of the tumor which is sufficiently acidic to sequester onco-tool. Both of these effects should increase the efficacy of the onco-tool.

Making the tumor more acidic also allows one to use an onco-tool with a lower pKa—which can result in a desirable increase in the onco-tool's therapeutic index.

c) Excessive Exposure of Bladder to Alpha and Beta Emissions

Over the course of a few hours much of the injected dose of an onco-tool will be excreted by the kidneys and is stored in the bladder until voided by urination. In the case of therapeutic onco-tools the buildup of radioactive onco-tool in the bladder has the potential of damaging the bladder. If damage to the bladder should prove to be a significant problem, it can be substantially reduced by irrigating the bladder during the period of time from when the onco-tool is injected until such time as most of the injected dose has been cleared from the patient's body.

d) Broad Range of pH Values in Tumor

For tumors having a broad range of pH values there is the potential that therapeutic onco-tools with too high of a pKa may aggregate or be largely bound to proteins or be bound to or enter cells close to tumor capillaries to such an extent that inadequate onco-tool remains to reach the lowest pH areas of the tumor most distant from the capillaries. Alternatively, therapeutic onco-tools with too low of a pKa may be too poorly sequestered in areas of higher pH closer to capillaries in the tumor, thereby leading to inadequate treatment of such areas. One strategy for dealing with a wide pH range within a tumor is to use a combination of at least two onco-tools, where one onco-tool with a higher pKa is maximally effective in higher-pH regions of the tumor closer to capillaries, and where another onco-tool with a lower pKa is maximally effective in lower-pH regions of the tumor which are further from capillaries. The rationale for such a combination of onco-tools is that the onco-tool with the higher pKa may be largely sequestered in areas close to capillaries and so little may remain available for reaching areas of lower pH further from capillaries—leaving those more acidic regions inadequately treated by the high-pka onco-tools. Conversely, the onco-tools with the lower pKa should be poorly sequestered in areas of higher pH near capillaries and so remain available to diffuse into areas of lower pH further from capillaries where they can then be effectively sequestered. Thus, together such a combination of low-pka and high-pKa onco-tools should have a better chance of achieving complete destruction of the tumor.

B. Onco-tool Function Determined by Radioisotope

It should be noted that any given onco-tool containing a cargo component in its effective-to-bind-a-radioisotope form, such as shown in FIGS. 22a and 23a, can generally be used either for detection of tumors, or for treating tumors. This dual potential is because it is the specific radioisotope which determines the function the onco-tool will carry out. For example, if the cargo component of the onco-tool constitutes the MAG3 group shown in FIG. 22a, and that onco-tool is reacted with the gamma-emitting radioisotope, technetium-99. then the resultant radioisotope-containing onco-tool will function for the detection of tumors. Conversely, if that onco-tool is instead reacted with the beta-emitting radioisotope, rhenium-186, then the resultant radioisotope-containing onco-tool will function for killing cells. As another example, if the cargo component of the onco-tool contains the trimethyl tin moiety shown in FIG. 23a, and that onco-tool is reacted with the gamma-emitting radioisotope, iodine-123, then the resultant radioisotope-containing onco-tool will function for the detection of tumors. Conversely, if that oncotool is instead reacted with the beta-emitting radioisotope, iodine-131, or the alpha-emitting radioisotope, astatine-211, then the resultant radioisotope-containing onco-tool can function for killing cells. However, because both of these particular radioisotopes also have emissions detectable at a distance, they can also function for detection of tumors. Thus, in general onco-tools in their stable effective-to-bind-a-radio-isotope form suitable for shipping and storage can be converted by the end used, by virtue of that user's choice of radioisotope which is reacted with that onco-tool, to a final form suitable for detection of tumors, or to a final form suitable for treatment of tumors, or to a final form which is suitable for detection and treatment of tumors.

C. Detecting Tumors

Because onco-tools exploit the acidity of tumors, one of the most universal of tumor characteristics, onco-tools should afford detection of tumors of most or all types, and sizes ranging from near-microscopic to very large. The method of using onco-tools for detecting tumors is suitable for many research applications, as well as for both veterinary medicine and human medicine. The diagnostic method generally includes the principal steps.

Step 1 The first step it to provide a diagnostic onco-tool. This entails contacting an onco-tool in its effective-to-bind form with a suitable radioisotope which is effective to report its presence. If a radiohalogen is to be used for this reporting function then the effective-to-bind form of the onco-tool should contain a moiety which affords rapid binding of the radiohalogen. Preferred moieties for this purpose are trialkyl tin moieties. For the case where an iodine radioisotope is to be used, both a tributyl tin and a trimethyl tin are suitable. In regard to the radioisotope, iodine-123 is particularly preferred for diagnostic use. It has a half-life of 13 hours and emits in 83% yield a 159 Kev gamma ray, which is readily detected by equipment routinely used in most nuclear medicine departments.

Step 2 After adding the radioisotope to the onco-tool, the resultant contains-a-radioisotope form of the onco-tool is delivered into the subject—generally by intravenous injection.

Step 3 The third step entails waiting a suitable period of time for excretion through the kidneys of most of the onco-tool dose—that portion which has not been sequestered in acidic areas of tumors. Specifically, over the course of a few hours most of the injected dose will be excreted by the kidneys, with significant retention of onco-tool only occurring if one or more tumors are present. While the rate of onco-tool excretion by the kidneys may vary somewhat with the structure of the selected onco-tool, that rate of excretion can generally be increased by increasing the subject's fluid intake, particularly if that fluid contains a diuretic. It is expected that typically in subjects who do not have tumors most of the onco-tool will be excreted in less than 24 hours.

Step 4 The last step in the diagnostic method is to scan the subject to determine if significant onco-tool has been sequestered in one or more tumors. With modern imaging equipment each tumor will show up as an obvious redioisotopic hot spot at the site of the tumor.

D. Treating Tumors a) Onco-tool in Combination with Conventional Cancer Therapies If a patient has been found to have one or more tumors, those tumors can be treated with an onco-tool to kill the treatment-resistant quiescent tumor cells in acidic areas of the tumors, as follows. First, provide a therapeutic onco-tool to treat the quiescent cells in acidic areas of those detected tumors. This entails contacting a selected onco-tool, in its effective-to-bind form, with an alpha-emitting radioisotope, which is particularly effective to kill quiescent tumor cells in acidic areas of tumors. The preferred radioisotope for this purpose is astatine-211, in which case the moiety on the effective-to-bind form of the onco-tool, which is to be displaced by the radioisotope, is preferably a trimethyl tin. After adding the radioisotope to the onco-tool, the resultant contains-a-radioisotope form of the onco-tool is delivered into the subject—generally by intravenous injection.

The patient should also be treated with a conventional cancer therapy, such as radiation therapy or chemotherapy, in order to also kill the more vulnerable fast-dividing tumor cells in less acidic areas of the tumor. Methods for such conventional tumor therapies are well known in the cancer treatment art.

b) Onco-tools-only Method

If a patient has been found to have one or more tumors, those tumors can be treated as follows. First, provide a combination of therapeutic onco-tools to treat those detected tumors. This entails contacting a portion of the selected onco-tool, in its effective-to-bind form, with an alpha-emitting radioisotope, which is particularly effective to kill quiescent tumor cells in acidic areas of tumors. The preferred radioisotope for this purpose is astatine-211, in which case the moiety on the effective-to-bind form of the onco-tool, which is to be displaced by the radioisotope, is preferably a trimethyl tin. In addition, another portion of the selected onco-tool, in its effective-to-bind form, is contacted with one or more beta-emitting radioisotopes having beta energies sufficient to kill the more vulnerable fast-dividing tumor cells in less acidic areas within a few hundred micrometers from the sequestered onco-tool. Typically, beta energies greater than about 0.2 Mev are suitable for this purpose. Preferred radioisotopes for this purpose are radiohalogens selected from Br-76, Br-82, I-130, I-131, I-133, and I-135. If a bromine and/or iodine radiohalogen is to be used, then the moiety on the effective-to-bind form of the onco-tool, which is to be displaced by that radioisotope, is preferably a tributyl tin or a trimethyl tin.

After adding the radioisotopes to the onco-tool portions, the resultant contains-a-radioisotope forms of the onco-tools are delivered into the subject—generally by intravenous injection. As noted earlier, because of the complex effects of alpha and beta particles on tumor cells, it may be desirable to deliver the onco-tool containing the alpha-emitting radioisotope at a different time than the one or more onco-tools containing the beta-emitting radioisotopes.

c) Ancillary Methods for Improved Results

In regard to using an onco-tool in veterinary or human medicine, be it for detection or for treatment of tumors, there are a number of points which should be considered.

First, if the treated subject has urine which is acidic (commonly the case) then most or all onco tools are expected to become sequestered in cells lining the proximal tubules of the kidneys. In a diagnostic mode this could obscure a signal from a tumor located in or near the kidney. In a therapeutic mode this could destroy the kidneys. Luckily, there are a number of safe over-the-counter drugs, such as Acetazolamide, which can be used to raise and maintain the urine at a pH greater than 7.4.

While this precaution is probably adequate for the case of onco-tools which contain only the advanced pH-switch components, for the case of onco-tools which contain a peptide pH-switch there is greater concern because the kidney has an aggressive reuptake mechansim for peptides. However, in light of their lack of basic amino acids, and particularly for peptide pH-switches prepared from D-amino acids (the unnatural chirality), it is unlikely reuptake will be a problem as long as the urine is kept at a pH above about 7.4, but reuptake needs to be carefully checked for during initial testing in animals. While a re-uptake problem is far less likely for onco-tools containing only advanced pH-switch components, they must also be checked carefully during initial testing in animals.

There are measures which can be taken to block reuptake of peptides, if it turns out to be a problem for a given onco-tool, but probably the safer approach is to identify a different onco-tool which does not suffer from reuptake. This is particularly the case for therapeutic applications where significant re-uptake by the kidneys could destroy them. As noted above, onco-tools lacking a peptide pH-switch component, but containing one or a few advanced pH-switch components are most likely to be free of re-uptake problems—as long as the urine is maintained at a pH above about 7.4 through the use of a suitable drug for this purpose.

Second, it is likely that the lower the pH is in acidic areas of tumors the more efficiently onco-tools will be sequestered in such areas. In this regard, there are several established methods that can be employed to further reduce the pH in tumors, without a corresponding reduction of the pH in normal tissues. One method is to introduce a substantial concentration of glucose into the subject. This has been shown to lead to a reduction of about 0.3 pH in the acidic areas of tumors (Kozin et al., Cancer Research Vol. 61, pages 4740-4743 (2001)). Alternatively, vasodilators, which are very safe and widely used drugs for reducing blood pressure, have also been shown to be effective for selectively reducing the pH in acidic areas of tumors—again by about 0.3 pH unit. Other drugs for further selectively reducing the pH in tumors are mitochondrial inhibitors. Combinations of such methods can achieve even greater reductions in tumor pH.

E. Integrated Method for Detecting Tumors and Treating Detected Tumors

Onco-tools offer the highly desirable properties of being able to both detect and treat tumors of most or all types, and sizes ranging from near-microscopic to very large. Because the diagnostic and the therapeutic onco-tools can be virtually identical—differing only in the contained radioisotope—in general if a given onco-tool structure is effective to detect a tumor, then that same onco-tool structure, but with a different radioisotope, should also be effective to treat that tumor.

These special properties of onco-tools make possible an integrated method for detecting tumors in living subjects, followed by treatment of tumors so detected in that subject. This integrated method is suitable for both veterinary medicine and human medicine. The integrated method comprises the following steps.

a) Detecting Tumors

Step 1 The first step it to provide a diagnostic onco-tool. This entails contacting an onco-tool in its effective-to-bind form with a suitable radioisotope which is effective to report its presence. If a radiohalogen is to be used for this reporting function then the effective-to-bind form of the onco-tool should contain a moiety which affords rapid binding of the radiohalogen. Preferred moieties for this purpose are trialkyl tin moieties. For the case where an iodine radioisotope is to be used, both a tributyl tin and a trimethyl tin are suitable. In regard to the radioisotope, iodine-123 is particularly preferred for diagnostic use. It has a half-life of 13 hours and emits in 83% yield a 159 Kev gamma ray, which is readily detected by equipment routinely used in most nuclear medicine departments.

Step 2 After adding the radioisotope to the onco-tool, the resultant contains-a-radioisotope form of the onco-tool is delivered into the subject—generally by intravenous injection.

Step 3 The third step entails waiting a suitable period of time for excretion through the kidneys of most of the onco-tool dose—that portion which has not been sequestered in acidic areas of tumors. Specifically, over the course of a few hours most of the injected dose will be excreted by the kidneys, with significant retention of onco-tool only occurring if one or more tumors are present. While the rate of onco-tool excretion by the kidneys may vary somewhat with the structure of the selected onco-tool, that rate of excretion can generally be increased by increasing the subject's fluid intake, particularly if that fluid contains a diuretic. It is expected that typically in subjects who do not have tumors most of the onco-tool will be excreted in less than 24 hours.

Step 4 The last step in the diagnostic portion of the integrated method is to scan the subject to determine if significant onco-tool has been sequestered in one or more tumors. With modern imaging equipment each tumor will show up as an obvious redioisotopic hot spot at the site of the tumor.

b) Treating Detected Tumors

Step 5 In the event one or more tumors are detected in step 4, the next step is to provide a combination of therapeutic onco-tools to treat those detected tumors. This entails contacting a portion of the selected onco-tool, in its effective-to-bind form, with an alpha-emitting radioisotope, which is particularly effective to kill quiescent tumor cells in acidic areas of tumors. The preferred radioisotope for this purpose is astatine-211, in which case the moiety on the effective-to-bind form of the onco-tool, which is to be displaced by the radioisotope, is preferably a trimethyl tin.

In addition, another portion of the selected onco-tool, in its effective-to-bind form, is contacted with one or more beta-emitting radioisotopes having beta energies sufficient to kill the more vulnerable fast-dividing tumor cells in less acidic areas up to a few hundred micrometers from the sequestered onco-tool. Typically, beta energies greater than about 0.2 Mev are suitable for this purpose. Preferred radioisotopes for this purpose are radiohalogens selected from Br-76, Br-82, I-130, I-131, I-133, and I-135. If a bromine and/or iodine radiohalogen is to be used, then the moiety on the effective-to-bind form of the onco-tool which is to be displaced by that radioisotope is preferably a tributyl tin or a trimethyl tin.

Step 6 After adding the radioisotopes to the onco-tool portions, the resultant contains-a-radioisotope forms of the onco-tools are delivered into the subject—generally by intravenous injection. As noted earlier, because of the complex effects of alpha and beta particles on tumor cells, it may be desirable to deliver the onco-tool containing the alpha-emitting radioisotope at a different time than the one or more onco-tools containing the beta-emitting radioisotopes.

c) Dealing with Micro-metastases

When a tumor reaches a substantial size (such as on the order of about 1 centimeter or larger) it commonly begins to metastasize, wherein single tumor cells or very small aggregates of tumor cells are released from the parent tumor, and those released cells can colonize at distant sites in the body. These colonies of cells, called micro-metastases, can then grow into new progeny tumors. The difficulty this presents for the onco-tools-only treatment method is that in the period of time between formation of the micro-metastases and the time it takes such micro-metastases to grow to a size sufficient to generate their own acidic areas (probably when they are about 1 millimeter in diameter) those sub-millimeter progeny tumors typically cannot be detected or killed by onco-tools.

Thus, while the parent tumor containing acidic areas can be detected and destroyed by onco-tools, any progeny micro-metastases smaller than about 1 millimeter in diameter are expected to survive the onco-tools treatment and ultimately lead to a relapse—though such a relapse may not occur for several years after the initial onco-tool treatment.

A strategy for solving this micro-metastases problem is to wait a period of time after the initial onco-tool therapy (steps 5 and 6 above) sufficient for any micro-metastases, that might be present and survived the initial treatment, to grow to a size where they develop acidic areas (typically about 1 millimeter in diameter). Conversely, those progeny micro-metastases should not be allowed to grow to the much larger size (probably on the order of 1 centimeter in diameter) where they too begin to metastasize. Once micro-metastases that might have escaped the first onco-tool treatment are in this proper size range (large enough to contain acidic areas, but not so large as to have begun metastasizing) one again carries out the onco-tool therapy process (repeat of steps 5 and 6 above).

A complication in the above strategy is that tumors exhibit a wide range of growth rates, and so it is difficult to predict how long it will take for any micro-metastases which might have escaped the first treatment to reach a size where they contain acidic regions. Therefore, the prudent course is to repeat diagnostic steps 1 through 4 above at appropriate intervals (perhaps once a year) continuing for a sufficient length of time (perhaps 5 to 10 years) to virtually assure that if any micro-metastases did escape destruction in the initial onco-tool therapy then such micro-metastases would have grown to a size sufficient to generate acidic regions and so be detected in one of the subsequent repeat diagnostic procedures (repeats of steps 1 through 4 above). If and when one of the repeat diagnostic procedures does detect one or more tumors, then the patient would be again treated as per steps 5 and 6 above. It seems likely that such a second treatment has a high probability of completely destroying any progeny tumors which might have escaped in the form of micro-metastases during the course of the initial onco-tool treatment—thereby completely clearing the patient of the original tumor and all its progeny.

d) Ancillary Methods for Improving Safety and Efficacy in the Integrated Method

In this integrated method for detection of tumors and treatment of detected tumors it is prudent to take measures to prevent re-uptake of onco-tool by the proximal tubules of the kidneys due to acidity in the subjects urine. This re-uptake problem can be prevented by pre-treating the subject with a suitable drug effective to raise the pH in the urine (described earlier in this Section 9). It is also desirable to increase the signal from or increase the damage to any tumors by further reducing the pH in the tumors. This is effected by pre-treating the subject with a suitable substance effective to further lower the pH in tumors (also described earlier in this Section 9). Finally, beginning shortly after the treatment step (step 6 above) it may be desirable to irrigate the patient's bladder for at least one hour, and preferably several hours, in order to more rapidly remove excreted radioactive onco-tool from the patient's body. This serves to minimize possible damage to the lining of the bladder. Lastly, In the interest of getting a cleaner signal in the onco-tool diagnostic method, and in the interest of minimizing exposure of the patient to radiation in the onco-tool treatment method, it may also be desirable to have the subject take in substantial fluid volume beginning shortly after the onco-tool is injected in order to increase removal of unsequestered onco-tool through urination. Adding a diuretic to this fluid is particularly effective for increasing the rate of excretion of the radioactive onco-tool by the kidneys.

EXAMPLES

Example 1

The sodium salts of propionic acid and octanoic acid in water were titrated with 5 M HCl.

The mid-point of the transition between salt and acid (pKa value) was found to be an expected 4.83 for propionic acid, but a surprisingly-high 5.5 for octanoic acid. The first derivative of the titration curve was symmetrical for the propionic acid, but highly unsymmetrical for the octanoic acid. In addition, droplets of octanoic acid came out of solution during the course of the octanoic titration.

In contrast, when the salts of these same two acids were titrated in methanol/water, 1:1 by vol., their mid-points of transition were virtually identical and the first derivative of their titration curves were now both symmetrical. Finally, in the titration in methanol/water no octanoic acid came out of solution.

These results suggest that the surprisingly high mid-point in the titration seen for octanoic acid in aqueous solution was due simply to the insolubility effects illustrated in FIGS. 9 and 10. The results further suggest that carrying out the titrations in methanol/water avoids these solubility effects on the titration curves.

Example 2

The compound in FIG. 12a was prepared by reacting camphoric anhydride with dimethylamine. The compound in FIG. 12b was prepared by reacting camphoric anhydride with ethylamine. The sodium salts of compounds shown in FIG. 12a (designed to form an internal acid-specific H-bond) and 12b (designed to form non-acid-specific H-bonds) were titrated in aqueous solution. The first derivative of the titration curve for the compound in FIG. 12b was symmetrical and showed an expected pKa value of 4.82, and there was no apparent insoluble material generated during the titration. In sharp contrast, the first derivative of the titration curve for the compound in FIG. 12a was highly skewed and showed a minimum at the surprisingly high value of 5.8, with the approximate mid-point of the titration at pH 5.6. Further, there was massive precipitate formed with each addition of HCl, starting when the pH reached 5.8.

These dramatic differences for nearly identical compounds suggest that the structure in FIG. 12a is forming the predicted internal acid-specific H-bond, and the structure in FIG. 12b is not forming such an H-bond.

Example 3

Titration of the 5-membered ring structure of FIG. 13a (prepared as in Example 2) and the acyclic structure of FIG. 13b (prepared by reacting the anhydride with dimethylamine) showed an expected pKa value of 4.95 for the acyclic structure, but an unexpectedly-high value of 5.6 for the 5-membered ring structure in FIG. 12a—accompanied by massive precipitation when the pH got below about 5.8, as well as skewing of the shape of the titration curve.

When these two compounds were titrated in methanol/water, 1:1 by vol, there was no sign of insolubility and the first derivative plots of the titration curves were now symmetrical. For the acyclic compound shown in FIG. 13b the pH at the mid-point of the titration was 5.8, while the pH at the mid-point of the titration was a substantially higher 6.45 for the structure in FIG. 13a.

Thus, even in the absence of skewing of the titration curve due to precipitation of the lipophilic acid form, one sees a substantial 0.65 pH unit increase in the mid-point of the titration curve for the compound in FIG. 13a. The most reasonable explanation for this seems to be that an internal acid-specific H-bond is forming and that that H-bond drives the equilibrium toward the acid form.

Example 4

A molecular model of structure 14b indicated that an internal H-bond should be strongly favored by the near-perfect geometry of said H-bond and the very limited conformational freedom between the H-bond donor and the H-bond acceptor moieties. In spite of these factors, when the salt of the structure in FIG. 14b (prepared by reacting maleic anhydride with dimethylamine) was prepared and titrated with HCl in aqueous solution, the titration curve indicates a pKa value below 3.0. This result suggests that the inductive effect from the amide, where said effect should be readily propagated through the intervening double bond, causes a large reduction in the pKa of the carboxyl, with that effect far surpassing any effect an internal H-bond might have on raising the pKa of the carboxyl.

Example 5

The two compounds in FIG. 15 were prepared by reacting the respective anhydrides with dimethylamine, and then the sodium salts titrated in methanol/water, 1:1 by volume—in order to preclude insolubility effects impacting the titration curve. In these experiments the first derivative of the titration plots were symmetrical and there was no visible sign of precipitation. Thus, the objective of avoiding insolubility effects was met What was found is that the structure of FIG. 15a showed a mid-point for the titration curve at a pH of 5.6, while the structure of FIG. 15b showed a significantly higher mid-point (at pH 6.14) for the titration.

Again, a reasonable explanation for the significantly higher value for the structure in FIG. 15b is that it is forming an internal acid-specific H-bond that is acting to shift the equilibrium in favor of the acid form, while the very similar structure in FIG. 15a fails to form a sufficiently stable H-bond and so the pKa is not significantly shifted.

Example 6

The methyl ester of isonipocotic acid was alkylated with bromopropane and then the resultant tertiary amine oxidized to the N-oxide with meta-Chlorobenzoylperoxide. Finally, the ester was cleaved with aqueous sodium hydroxide to give structure iii in FIG. 16b. This product in its sodium salt form was titrated in water. The first derivative of its titration plot shows two minimums, one at about pH 4.0 (which is reasonably close to that expected for the N-oxide moiety), and the other minimum at about pH 5.6, which is substantially higher than would be expected for either the N-oxide moiety or the carboxylic acid moiety. However, in light of the results in the earlier examples herein, it seems likely that this 5.6 value is due to an internal low-barrier H-bond forming between the carboxyl H-bond donor and the N-oxide H-bond acceptor, where that internal H-bond acts to drive the equilibrium toward the acid form.

I claim:
1. A compound structured to be selectively sequestered in acidic areas of a tissue, comprising:
(a) at least one advanced pH-switch which includes
i) a non-aromatic ring selected from the group consisting of:
a 4-membered ring,
a 5-membered ring, and
a 6-membered ring;
ii) a single carboxylic acid linked directly to said non-aromatic ring;
iii) said carboxylic acid is separated from any linked electron-withdrawing group by at least two carbons;
iv) an H-bond acceptor having a pKa of less than 7, wherein said H-bond acceptor meets one of the following criteria:
said H-bond acceptor is part of said non-aromatic ring,
said H-bond acceptor is linked directly to said non-aromatic ring, or
said H-bond acceptor is linked through a one-atom spacer to said non-aromatic ring;
v) said H-bond acceptor in its non-ionic form cannot serve as an H-bond donor;
vi) said carboxylic acid and said H-bond acceptor are positioned and oriented so that they can form an internal acid-specific H-bond; and,
(b) at least one advanced cargo which includes
i) a structure selected from the group consisting of:
an alkene,
a 5-membered aromatic ring,
a 6-membered aromatic ring; and,
ii) linked directly to said structure is a radiohalogen having a chemical form selected from:
a vinyl halide; and,
an aryl halide.
2. The compound of claim 1, comprising at least two advanced pH-switches.
3. The compound of claim 2, comprising two advanced pH-switches, and one advanced cargo wherein the radiohalogen is an iodine-131 radioisotope, having the structure:

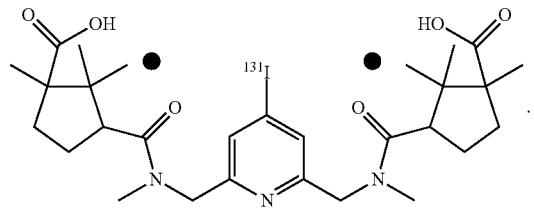

4. A precursor compound structured to be selectively sequestered in acidic areas of a tissue, comprising:
(a) at least one advanced pH-switch which includes
i) a non-aromatic ring selected from the group consisting of:
a 4-membered ring,
a 5-membered ring, and
a 6-membered ring;
ii) a single carboxylic acid linked directly to said non-aromatic ring;
iii) said carboxylic acid is separated from any linked electron-withdrawing group by at least two carbons;
iv) an H-bond acceptor having a pKa of less than 7, wherein said H-bond acceptor meets one of the following criteria:

said H-bond acceptor is part of said non-aromatic ring, said H-bond acceptor is linked directly to said non-aromatic ring, or said H-bond acceptor is linked through a one-atom spacer to said non-aromatic ring;

v) said H-bond acceptor in its non-ionic form cannot serve as an H-bond donor;

vi) said carboxylic acid and said H-bond acceptor are positioned and oriented so that they can form an internal acid-specific H-bond; and, (b) at least one advanced cargo which includes i) a structure selected from the group consisting of:
an alkene,
a 5-membered aromatic ring, and
a 6-membered aromatic ring; and, ii) linked directly to said structure is a moiety that can be readily displaced by a radiohalogen.

5. The precursor compound of claim 4, comprising at least two advanced pH-switches.

6. The precursor compound of claim 5, comprising two advanced pH-switches, and one advanced cargo, having the structure:

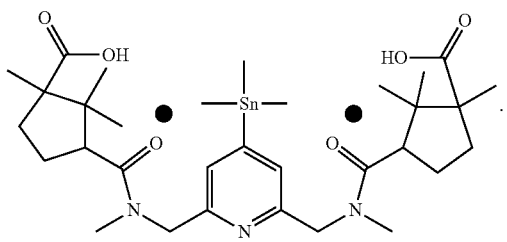

* * * * *